US006046186A

United States Patent [19]
Tanabe et al.

[11] Patent Number: 6,046,186
[45] Date of Patent: Apr. 4, 2000

[54] ESTRONE SULFAMATE INHIBITORS OF ESTRONE SULFATASE, AND ASSOCIATED PHARMACEUTICAL COMPOSITIONS AND METHODS OF USE

[75] Inventors: Masato Tanabe, Palo Alto; Richard H. Peters, San Jose; Wan-Ru Chao, Sunnyvale; Kazuhiko Shigeno, Saitama, all of Calif.

[73] Assignee: SRI International, Menlo Park, Calif.

[21] Appl. No.: 08/997,416

[22] Filed: Dec. 24, 1997

[51] Int. Cl.$^7$ .......................... A61K 31/56; A61K 31/58; C07J 43/00; C07J 9/00
[52] U.S. Cl. .......................... 514/178; 514/176; 514/179; 514/182; 540/113; 552/502; 552/515; 552/531; 552/540; 552/543; 552/544; 552/548; 552/552; 552/553; 552/555; 552/556; 552/558; 552/618; 552/626; 552/650; 552/652
[58] Field of Search ............................ 540/113; 514/176, 514/178, 179, 182; 552/515, 531, 540, 543, 544, 548, 502, 552, 553, 555, 556, 558, 618, 626, 650, 652

[56] References Cited

U.S. PATENT DOCUMENTS

| | | | |
|---|---|---|---|
| 5,556,847 | 9/1996 | Johnson et al. | 514/178 |
| 5,616,574 | 4/1997 | Reed et al. | 514/178 |

FOREIGN PATENT DOCUMENTS

| | | |
|---|---|---|
| WO 93/05064 | 3/1993 | WIPO . |
| WO 95/26717 | 10/1995 | WIPO . |
| WO 98/24802 | 6/1998 | WIPO . |

OTHER PUBLICATIONS

Adams et al. (1979), "A Correlation between Estrogen Sulfotransferase Levels and Estrogen Receptor Status in Human Primary Breast Carcinoma," *Cancer Res.* 39:5124–5126.
Bradlow et al. (1982), "A Reassessment of the Role of Breast Tumor Aromatization," *Cancer Res.* (Suppl.) 42:3382s–3386s.
Dibbelt et al. (1994), "Inhibition of Human Placental Sterylsulfatase by Synthetic Analogs of Estrone Sulfate," *J. Steroid Biochem. & Molec. Biol.*50(5/6):261–266.
Duncan et al. (1993), "Inhibition of Estrone Sulfatase Activity by Estrone–3–methylthiophosphonate: A Potential Therapeutic Agent in Breast Cancer," *Cancer Research* 53:298–303.
Evans et al. (1991), "Inhibition of Estrone Sulfatase Enzyme in Human Placenta and Human Breast Carcinoma" *J. Steroid Biochem. Mol. Biol.* 39(4A):493–499.
Howarth et al. (1994), "Estrone Sulfamates: Potent Inhibitors of Estrone Sulfatase with Therapeutic Potential," *J. Med. Chem.* 37:219–221.
Li et al. (1993), "Synthesis and Biochemical Studies of Estrone Sulfatase Inhibitors," *Steroids* 58:106–111.
Li et al. (1995), "Estrone Sulfate Analogs as Estrone Sulfatase Inhibitors," *Steroids* 60:299–306.

Pasqualini et al. (1989), "Importance of Estrogen Sulfates in Breast Cancer," *J. Steroid Biochem.* 34(1–6):155–163.
Pasqualini et al. (1992), "Recent Data on Estrogen Sulfatases and Sulfotransferases Activities in Human Breast Cancer," *J. Steroid Biochem. Mol. Biol.* 41(308):323–329.
Prost et al. (1984), "Estrone and Dehydroepiandrosterone Sulfatase Activities and Plasma Estrone Sulfate Levels in Human Breast Carcinoma,", *Cancer Res.* 44:661–664.
Purohit et al. (1992), "Oestrogen Sulphatase Activity in Hormone–Dependent and Hormone–Independent Breast–Cancer Cells: Modulation by Steroidal and Non–steroidal Therapeutic Agents" *Int. J. Cancer* 50:901–905.
Purohit et al. (1995), "Inactivation of Steroid Sulfatase by an Active Site–Directed Inhiobitor, Estrone–3–O–Sulfamate," *Biochemistry* 34:11508–11514.
Santner et al. (1984), "In Situ Estrogen Production via the Estrone Sulfatase Pathway in Breast Tumors: Relative Importance versus the Aromatase Pathway," *J. Clin. Endocrinol. Metabol.* 59(1):29–33.
Santner et al. (1993), "Estrone Sulfate Promotes Human Breast Cancer Cell Replication and Nuclear Uptake of Estradiol in MCF–7 Cell Cultures," *Int. J. Cancer*54:119–124.
Thijssen et al. (1986), "Uptake and Concentration of Steroid Hormones in Mammary Tissues," *Acad. Sci.* 464:106–116.
Vignon et al. (1980), "Effects of Plasma Estrogen Sulfates in Mammary Cancer Cells," *Endocrinology* 106(4):1079–1086.

(List continued on next page.)

*Primary Examiner*—Richard L. Raymond
*Assistant Examiner*—Brenda Coleman
*Attorney, Agent, or Firm*—Dianne E. Reed; Reed & Associates

[57] ABSTRACT

Novel compounds useful as inhibitors of estrone sulfatase are provided. The compounds have the structural formula (I)

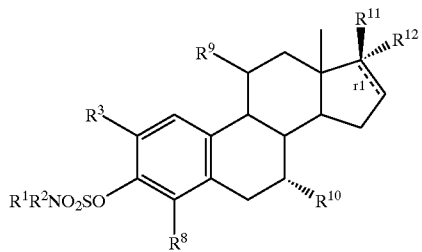

wherein r1 is an optional double bond, $R^1$ and $R^2$ are selected from the group consisting of hydrogen and lower alky, or together form a cyclic substituent (II)

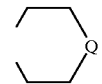

wherein Q is NH, O or $CH_2$, and the other various substituents are as defined herein. Pharmaceutical compositions and methods for using the compounds of formula (I) to treat estrogen-dependent disorders are provided as well.

65 Claims, No Drawings

OTHER PUBLICATIONS

Woo et al., Oestrone 3–O–(N–Acetyl)Sulphamate, A Potential Molecular Probe of the Active Site of Oestrone Sulphatase, Bioorganic & Medicinal Chemistry Letters, vol. 7, No. 24, pp. 3075–3080, Dec. 1997.

Howarth et al. (1997), "Estrone Sulfonates as Inhibitors of Estrone Sulfatase," *Steroids* 62:346–350.

Schwarz et al. (1996), "Synthesis of Estrogen Sulfamates: Compounds with a Novel Endocrinological Profile," *Steroids* 61:710–717.

Schwarz et al. (1975), "Steroide Sulfonyloxyderivate von Ostrogenen," *Pharmazie* 30(1): 17–21.

Woo et al. (1996), "Active Site Directed Inhibition of Estrone Sulfatase by Nonsteroidal Coumarin Sulfamates," *J. Med. Chem.* 39:1349–1351.

ESTRONE SULFAMATE INHIBITORS OF ESTRONE SULFATASE, AND ASSOCIATED PHARMACEUTICAL COMPOSITIONS AND METHODS OF USE

TECHNICAL FIELD

The present invention relates generally to steroid hormones, and more specifically relates to novel steroids which are inhibitors of the enzyme estrone sulfatase. The invention additionally relates to methods for inhibiting estrone sulfatase activity, to treatment of disorders that are estrogen-dependent, i.e., are estrogen-induced or estrogen-stimulated, and to pharmaceutical compositions containing one or more of the novel compounds.

BACKGROUND

Breast cancer is one of the most prevalent types of cancer, and epidemiological and clinical studies have shown that approximately one-third of breast tumors are estrogen-dependent. This means that estrogens are required for the growth of such breast tumors in both premenopausal and postmenopausal patients. In postmenopausal women, in whom breast cancer most commonly occurs, breast tumor concentrations of estrone and estradiol are considerably higher than blood estrogen levels. Although retention of estrogens in breast tumors by high-affinity binding proteins contributes to the level of estrogens in tumors, estrogen concentrations in the breast are higher than plasma levels in breast cancer patients regardless of whether their tumors are estrogen receptor-positive (ER+) or receptor-negative (ER−). In situ formation of estrogen from estrogen biosynthetic precursors within tumors is now known to make a major contribution to the estrogen content of breast tumors.

The principal naturally occuring estrogens are 17β-estradiol, estrone, and estriol. The enzymes required for estradiol biosynthesis (i.e., aromatase, 17β-hydroxy-steroid dehydrogenase, and estrone sulfatase) are present in normal and malignant breast tissues. Blood concentrations of estrone sulfate are 8- to 10-fold greater than those of unconjugated free estrone, and breast tissue concentrations of estrone sulfatase activity, the enzyme responsible for the conversion of estrone sulfate to estrone, are a thousand-fold higher than those of aromatase activity. Together, these findings suggest that estrone sulfatase plays a key role in regulating the formation of estrogens within breast tumors, particularly in postmenopausal women. See, e.g.: Pasqualini et al., *Ann. N.Y. Acad. Sci.* 464:106–116 (1986); Santner et al., *J. Clin. Endocrinol. Metabol.* 59(1): 29–33 (1984); Evans et al., *J. Steroid Biochem. Mol. Biol.* 39:493–499 (1991); Pasqualini et al., *J. Steroid Biochem. Mol. Biol.* 41(308):323–329 (1992); Vignon et al., *Endocrinology* 106(4):1079–1086 (1980); and Santner et al., *Int. J. Cancer* 54: 119–124 (1993).

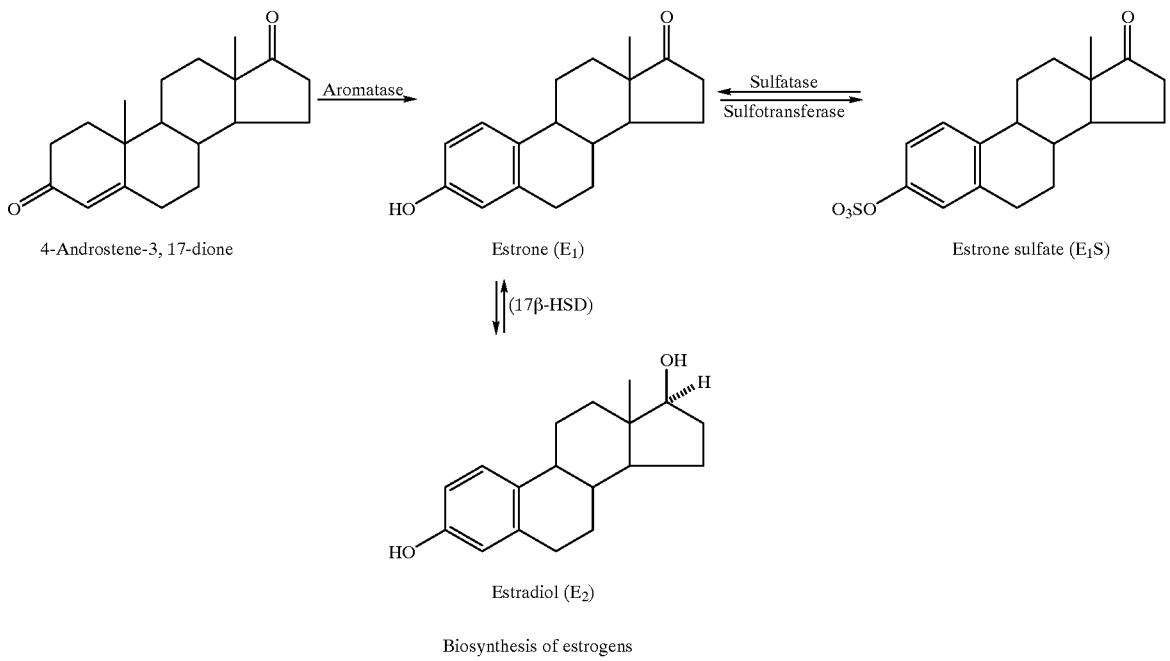

Biosynthesis of estrogens

There is additional evidence of the relative significance of the aromatase and estrone sulfatase pathways in providing sufficient estrogen to sustain tumor growth. In postmenopausal women, the levels of estradiol in breast tumor tissues are 10 to 40 times higher than in plasma and are similar to those in premenopausal women, even though plasma estrogen levels are much lower after the menopause. This concentration gradient is not entirely due to estradiol uptake and binding to estrogen receptors, since tissue estradiol levels correlate poorly with estrogen receptor levels.

In situ production of estradiol, through either the aromatase or the estrone sulfatase pathway, could affect this gradient. The level of estrone sulfate present in the serum of postmenopausal women is 10 times higher than the level of free estrogens (Prost et al., *Cancer Res.* 44:661–664 (1984)). Serum estrone sulfate levels are also higher in postmenopausal women with breast cancer than in normal postmenopausal women (Purohit et al., *Int. J. Cancer* 50:901–905 (1992)). Also, sulfatase levels in tumors are much higher than aromatase levels (Pasqualini et al., *J. Steroid Biochem.* 34(1–6):155–163 (1989); Adams et al., *Cancer Res.* 39:5124–5126 (1979)). The absolute levels of aromatase activity in tumors are relatively low, ranging from 5 to 80 pmol/g protein/h. Bradlow (Bradlow et al., *Cancer Res.* (Suppl.) 42:3382s-3386s (1982)) and others consider this degree of tumor aromatase activity too low for a biologically meaningful level of estradiol to be synthesized locally within the tumor.

Quantitative information on the local production of estrogen shows that the sulfatase activity in breast tumors is more than 10 times the aromatase activity. When sulfatase and aromatase activity in human tumors were compared at physiological levels of substrate, sulfatase produced 2.8 pmol estrone/g protein/h while aromatase produced only 0.27 pmol/g protein/h. Consequently, estrone sulfate represents one of the most important precursors for tissue production of estradiol, and estrone sulfatase is a quantitatively more important local route for estrogen production than aromatase.

To date, little work has been done in the development of estrone sulfatase inhibitors. Li et al., *Steroids* 60:299–306 (1995), evaluate several compounds as potential inhibitors of human placental sterylsulfatase, but do not identify any highly potent estrone sulfatase inhibitors. Similarly, Duncan et al., *Cancer Research* 53: 298–303 (1993), evaluate a potential estrone sulfatase inhibitor, estrone-3-methylthiophosphonate, but conclude that the experimental work done with that compound would hopefully lead to development of "more efficient" inhibitors of the enzyme.

Accordingly, the present invention is directed to novel compounds that are extremely effective estrone sulfatase inhibitors. The invention thus represents a significant advance in the art, particularly in the treatment of breast cancer and other diseases and conditions that are potentiated by the presence of estrogens.

In addition to the references cited above, the following pertain to one or more aspects of the invention and as much may be of background interest to those skilled in the art: Howarth et al., *J. Med. Chem.* 37:219–221 (1994) and PCT Publication No. WO93/05064 relate to certain estrone sulfamates as inhibitors of steroid sulfatases, with Howarth et al. specifically focused on inhibition of estrone sulfatase. In addition, Dibbelt et al., *J. Steroid Biochem. & Molec. Biol.* 50(5/6):261–266 (1994) evaluates estrone sulfamate as a potential inhibitor of human placental sterylsulfatase, while Li et al., *Steroids* 58:106–111 (1993), and Purohit et al., *Biochemistry* 34:11508–11514 (1995) also, discuss estrone sulfamate as a potential enzyme inhibitor. However, the compounds described in these and other references are believed to give rise to estrogenic products upon hydrolysis, unlike the novel compounds provided herein.

SUMMARY OF THE INVENTION

Accordingly, it is a primary object of the invention to address the above-mentioned need in the art by providing novel compounds useful as inhibitors of estrone sulfatase.

It is another object of the invention to provide novel estrone sulfatase inhibitors which are non-estrogenic.

It is still another object of the invention to provide such compounds which do not give rise to estrogenic products when hydrolyzed.

It is yet another object of the invention to provide novel estrone sulfatase inhibitors which are anti-estrogenic.

It is an additional object of the invention to provide such compounds which give rise to anti-estrogenic products upon hydrolysis.

It is another object of the invention to provide a method for inhibiting estrone sulfatase activity using the novel compounds.

It is a further object of the invention to provide a method for treating an individual with a disorder that is estrogen-dependent, i.e., an estrogen-induced or estrogen-stimulated condition or disease, by administering to the individual an effective estrone sulfatase inhibiting amount of a novel compound as provided herein, or a pharmaceutically acceptable salt thereof.

It is yet a further object of the invention to provide a pharmaceutical composition for treating an individual with a disorder that is estrogen-dependent, the composition comprising a pharmaceutically acceptable carrier and an effective estrone sulfatase inhibiting amount of a novel compound as provided herein or a pharmaceutically acceptable salt thereof.

Additional objects, advantages and novel features of the invention will be set forth in part in the description which follows, and in part will become apparent to those skilled in the art upon examination of the following, or may be learned by practice of the invention.

In one embodiment, the invention relates to novel compounds having the structure of Formula (I)

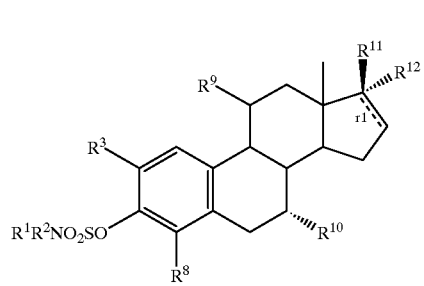

(I)

wherein:
r1 is an optional double bond;
$R^1$ and $R^2$ are selected from the group consisting of hydrogen and lower alkyl, or together form a cyclic substituent (II)

(II)

wherein Q is NH, O or $CH_2$;
$R^3$ is selected from the group consisting of hydrogen, —CN, —$NO_2$, —$COOR^4$ wherein $R^4$ is hydrogen or lower alkyl, —$(CH_2)_nOR^5$ and —$(CH_2)_nNR^6R^7$ wherein n is an integer in the range of 0 to 6, $R^5$ is hydrogen or lower alkyl, and $R^6$ and $R^7$ are selected from the group consisting of hydrogen, lower alkyl and lower acyl, or together form the cyclic substituent (II);
$R^8$ is selected from the group consisting of hydrogen, —$NO_2$, and $NR^6R^7$;
$R^9$ and $R^{10}$ are independently selected from the group consisting of hydrogen and lower alkyl; and
one of $R^{11}$ and $R^{12}$ is hydrogen and the other is lower alky, lower alkenyl, lower alkynyl, lower alkoxy, lower acyl, lower acyloxy, or —$(CH_2)_m$—O—$(CH_2)_q$—$NR^6R^7$ wherein m and q are integers in the range of 0 to 6 and 1 to 6, respectively, or $R^{11}$ and $R^{12}$ together form =O or =$CR^{13}R^{14}$ in which $R^{13}$ and $R^{14}$ are independently selected from the group consisting of hydrogen, lower alkyl, —CN, —$(CH_2)_m$—O—$(CH_2)_q$—$NR^6R^7$ and —$COOR^4$.

The invention also relates to pharmaceutical compositions containing one or more compounds of structural formula (I), and further relates to methods of using the compounds to inhibit estrone sulfatase activity and to treat individuals with disorders that are estrogen-dependent.

DETAILED DESCRIPTION OF THE INVENTION

Definitions and Nomenclature:

Before the present compounds, compositions and methods are disclosed and described, it is to be understood that this invention is not limited to specific reagents or reaction conditions, specific pharmaceutical carriers, or particular administration regimens, as such may, of course, vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "an estrone sulfatase inhibitor" includes mixtures of estrone sulfatase inhibitors, reference to "a pharmaceutical carrier" includes mixtures of two or more such carriers, and the like.

In this specification and in the claims which follow, reference will be made to a number of terms which shall be defined to have the following meanings:

The term "alkyl" as used herein refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like, as well as cycloalkyl groups such as cyclopentyl, cyclohexyl and the like. Preferred alkyl groups herein contain 1 to 12 carbon atoms. The term "lower alkyl" intends an alkyl group of one to six carbon atoms, preferably one to four carbon atoms.

The term "alkenyl" as used herein refers to a branched or unbranched hydrocarbon group of 2 to 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl and the like. Preferred alkenyl groups herein contain 2 to 12 carbon atoms. The term "lower alkenyl" intends an alkenyl group of two to six carbon atoms, preferably two to four carbon atoms. The term "cycloalkenyl" intends a cyclic alkenyl group of three to eight, preferably five or six, carbon atoms.

The term "alkynyl" as used herein refers to a branched or unbranched hydrocarbon group of 2 to 24 carbon atoms containing at least one triple bond, such as ethynyl, n-propynyl, isopropynyl, n-butynyl, isobutynyl, octynyl, decynyl and the like. Preferred alkynyl groups herein contain 2 to 12 carbon atoms. The term "lower alkynyl" intends an alkynyl group of two to six carbon atoms, preferably two to four carbon atoms.

The term "alkoxy" as used herein intends an alkyl group bound through a single, terminal ether linkage; that is, an "alkoxy" group may be defined as —OR where R is alkyl as defined above. A "lower alkoxy" group intends an alkoxy group containing one to six, more preferably one to four, carbon atoms.

The term "acyl" is used in its conventional sense to refer to a molecular substituent RCO— where R is alkyl as defined above. The term "lower acyl" refers to an acyl group wherein R contains one to six, more preferably one to four, carbon atoms.

The term "ester" is used herein in its conventional sense to refer to a molecular substituent R(CO)O— where R is alkyl as defined above. A "lower alkyl ester" group intends an ester group containing one to six, more preferably one to four, carbon atoms, i.e., a lower acyloxy group.

The term "aryl" as used herein refers to a monocyclic aromatic species of 5 to 7 carbon atoms, and is typically phenyl. Optionally, these groups are substituted with one to four, more preferably one to two, lower alkyl, lower alkoxy or hydroxyl substituents.

The term "sulfamate" is used in its conventional sense to refer to a molecular substituent having the general formula —$O(SO_2)NR^1R^2$. In some instances, a sulfamate group may be drawn as $R^1R^2NO_2SO$—, but it is to be understood that the sulfur atom is directly bonded to each of the three oxygen atoms as well as to the nitrogen atom, with no oxygen atoms separating $R^1$ and $R^2$ may be H; optionally, they may represent other substituents as discussed elsewhere herein.

The term "inhibitor" as used herein is intended to include both reversible enzyme inhibitors and irreversible enzyme inhibitors, i.e., enzyme inactivators.

"Optional" or "optionally" means that the subsequently described event or circumstance may or may not occur, and that the description includes instances where said event or circumstance occurs and instances where it does not. For example, the phrase "optional double bond" used to refer to the dotted line in the structure of formula (I) indicated as "r1" means that either a single bond or a double bond is present.

By the terms "effective amount" or "pharmaceutically effective amount" or "estrone sulfatase inhibiting amount" of an agent as provided herein are meant a nontoxic but sufficient amount of the agent to provide the desired level of enzyme inhibition and corresponding therapeutic effect. As will be pointed out below, the exact amount required will vary from subject to subject, depending on the species, age, and general condition of the subject, the severity of the condition being treated, and the particular enzyme inhibitor and mode of administration, and the like. Thus, it is not possible to specify an exact "effective amount." However, an appropriate "effective" amount in any individual case may be determined by one of ordinary skill in the art using only routine experimentation.

By "pharmaceutically acceptable carrier" is meant a material which is not biologically or otherwise undesirable, i.e., the material may be administered to an individual along with the selected estrone sulfatase inhibitor without causing any undesirable biological effects or interacting in a deleterious manner with any of the other components of the pharmaceutical composition in which it is contained. Similarly, a "pharmaceutically acceptable" salt or a "pharmaceutically acceptable" ester of a novel compound as provided herein is a salt or ester which is not biologically or otherwise undesirable.

The term "estrogenic" relates to the ability to produce some or all of the effects produced by estrogens. Conversely, the term "non-estrogenic" is used to refer to compounds which do not produce estrogenic effects. The preferred compounds described herein are non-estrogenic, and upon hydrolysis do not give rise to estrogenic products. The term "reduced estrogenic activity" refers to a compound that has 60% or less of the estrogenic activity of estradiol. A compound may also be referred to herein as having "substantially no estrogenic activity," meaning that the compound has less than about 5%, preferably less than about 2%, of the estrogenic activity of estradiol.

The term "anti-estrogenic" is used herein to mean the ability to inhibit or modify the effects produced by estrogens. An "anti-estrogenic" compound tends to inhibit the activity or the in situ production of estrogens such as estradiol, following administration to a mammalian individual. Preferred compounds of the invention are anti-estrogenic in nature and give rise to anti-estrogenic products upon hydrolysis. A "pure" antiestrogenic compound as used herein refers to an anti-estrogenic compound which has no estrogenic activity, or substantially no estrogenic activity.

In describing the location of groups and substituents, the following numbering systems will be employed. This system is intended to conform the numbering of the cyclopentanophenanthrene nucleus to the convention used by the IUPAC or Chemical Abstracts Service. The term "steroid" as used herein is intended to mean compounds having the aforementioned cyclopentanophenanthrene nucleus.

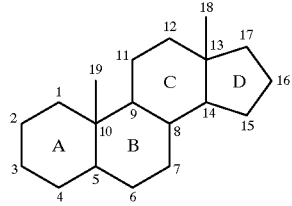

In these structures, the use of bold and dashed lines to denote particular conformation of groups again follows the IUPAC steroid-naming convention. The symbols "α" and "β" indicate the specific stereochemical configuration of a substituent at an asymmetric carbon atom in a chemical structure as drawn. Thus "α," denoted by a broken line, indicates that the group in question is below the general plane of the molecule as drawn, and "β," denoted by a bold line, indicates that the group at the position in question is above the general plane of the molecule as drawn.

In addition, the five- and six-membered rings of the steroid molecule are often designated A, B, C and D as shown.

The Novel Compounds:

The novel compounds provided herein are those defined by structural formula (I), wherein $R^1$, $R^2$, $R^3$, $R^8$ through $R^{12}$ and r1 are as defined above.

Preferred compounds are wherein $R^1$, $R^2$, $R^9$ and $R^{10}$ are hydrogen, and the optional double bond r1 is not present.

Within this preferred group, particularly preferred compounds are:

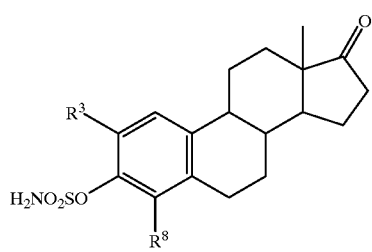

(III)

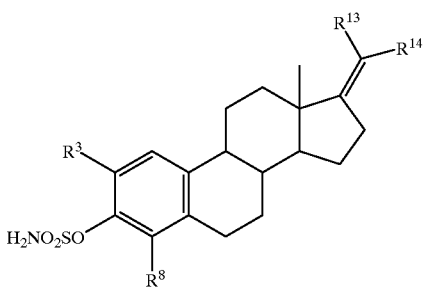

(IV)

wherein $R^3$ and $R^8$ are as defined previously, and one of $R^{13}$ and $R^{14}$ is hydrogen, and the other is as defined previously, or wherein $R^{13}$ and $R^{14}$ are both —CN; and

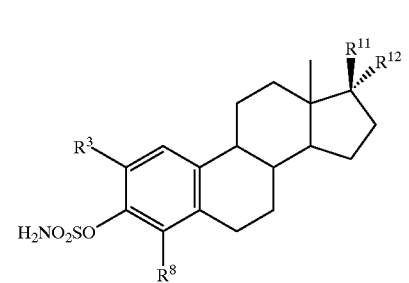

(V)

wherein one of $R^{11}$ and $R^{12}$ is hydrogen and the other is —$(CH_2)_m$—O$(CH_2)_q$—N$(CH_3)_2$, and wherein m is preferably 0 or 1 and q is preferably 2, 3 or 4.

Examples of specific compounds of formula (I) include, but are not limited to, the following:

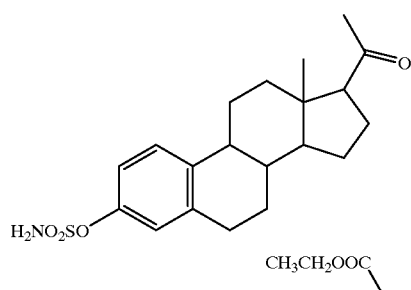

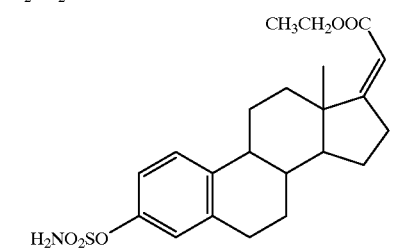

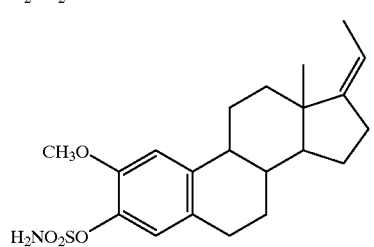

9
-continued
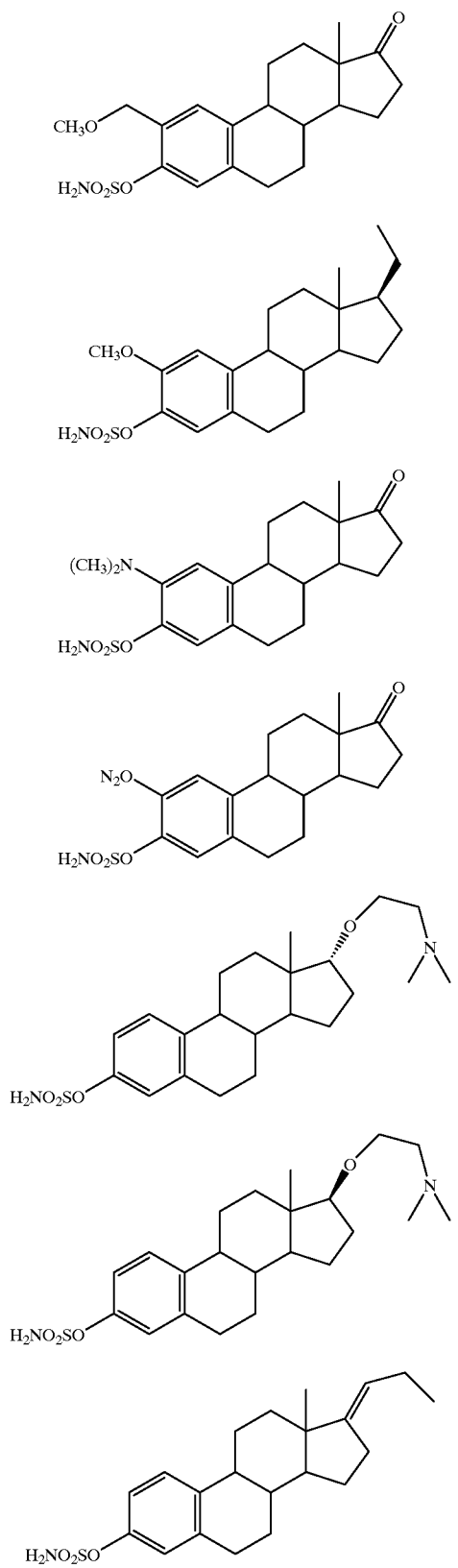
10
-continued
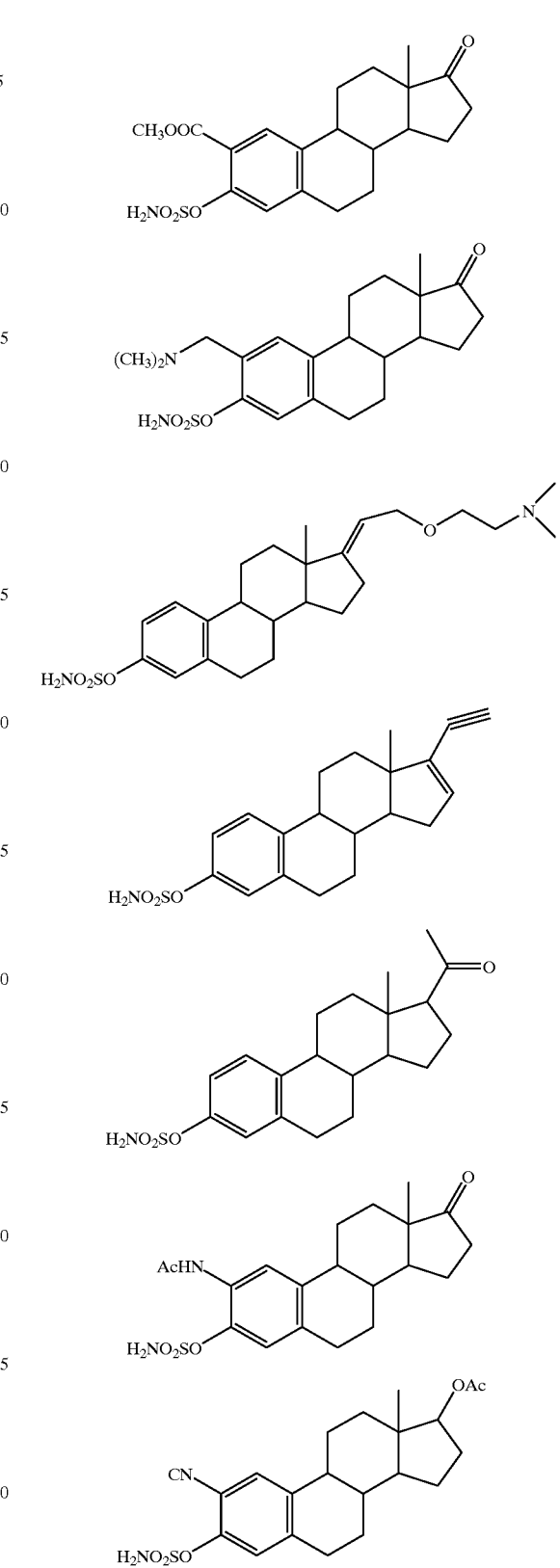

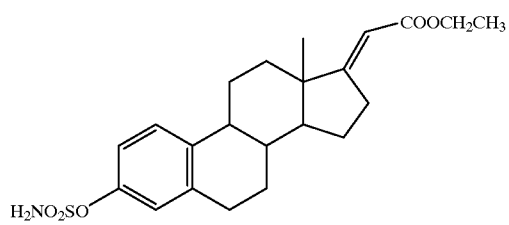
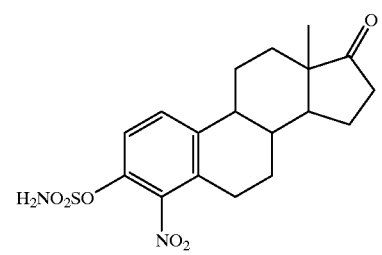
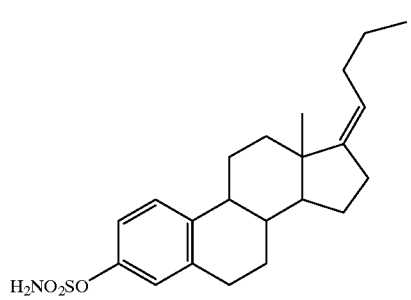
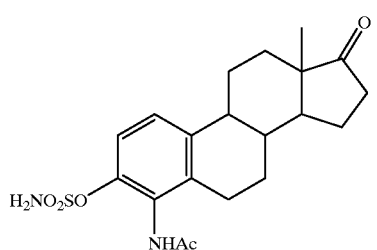
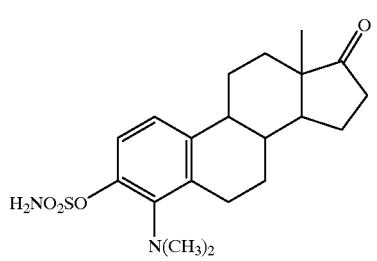
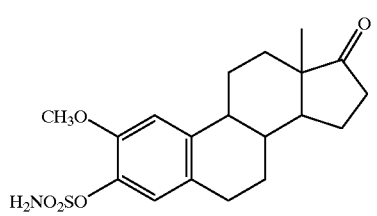
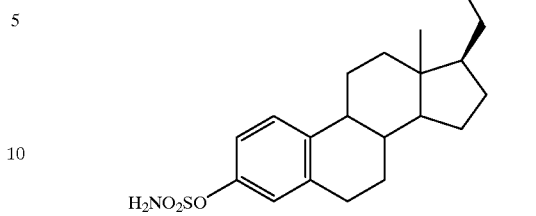
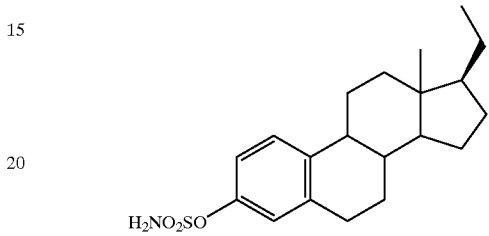
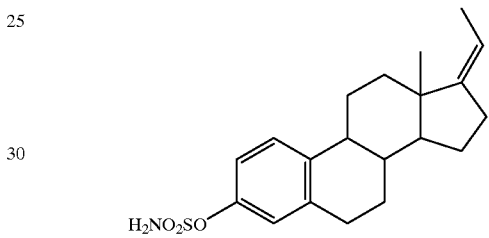
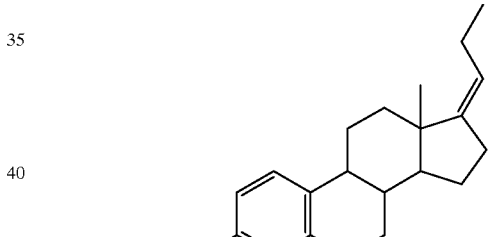
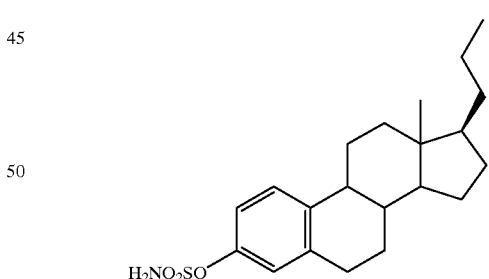
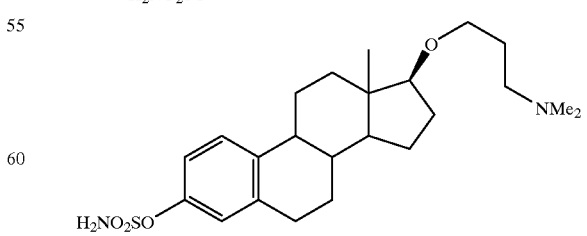

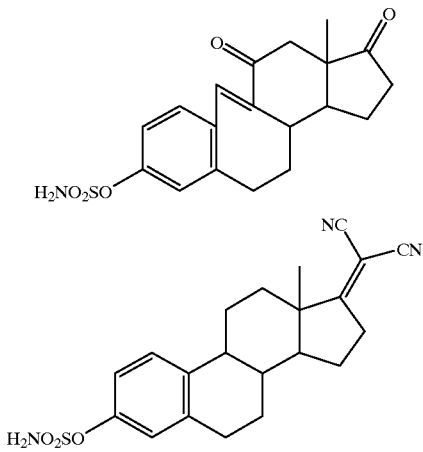

The compounds may be in the form of pharmaceutically acceptable salts or esters, or may be modified by appending one or more appropriate functionalities to enhance selected biological properties. Such modifications are known in the art and include those which increase biological penetration into a given biological system, increase oral bioavailability, increase solubility to allow administration by injection, and the like.

Salts of the compounds can be prepared using standard procedures known to those skilled in the art of synthetic organic chemistry and described, for example, by J. March, *Advanced Organic Chemistry: Reactions. Mechanisms and Structure*, 4th Ed. (New York: Wiley-Interscience, 1992). Acid addition salts are prepared from the free base (e.g., compounds having a neutral —$NH_2$ or cyclic amine group) using conventional means, involving reaction with a suitable acid. Typically, the base form of the compound is dissolved in a polar organic solvent such as methanol or ethanol and the acid is added at a temperature of about 0° C. to about 100° C., preferably at ambient temperature. The resulting salt either precipitates or may be brought out of solution by addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base.

Preparation of basic salts of acid moieties which may be present (e.g., carboxylic acid groups) are prepared in a similar manner using a pharmaceutically acceptable base such as sodium hydroxide, potassium hydroxide, ammonium hydroxide, calcium hydroxide, magnesium hydroxide, trimethylamine, or the like.

Preparation of esters involves functionalization of hydroxyl and/or carboxyl groups which may be present. These esters are typically acyl-substituted derivatives of free alcohol groups, i.e., moieties which are derived from carboxylic acids of the formula RCOOH where R is alkyl, and preferably is lower alkyl. Pharmaceutically acceptable esters may be prepared using methods known to those skilled in the art and/or described in the pertinent literature. Esters can be reconverted to the free acids, if desired, by using conventional hydrogenolysis or hydrolysis procedures.

Certain of the novel compounds are chiral in nature and can thus be in enantiomerically pure form or in a racemic mixture. The invention encompasses both the enantiomerically pure form of such compounds as well as diastereomeric and racemic mixtures thereof. Furthermore, certain compounds are stereoisomers which are asymmetric with respect to a C=C bond. In such a case, the invention encompasses both such structures, i.e., both the "E" and "Z" isomers, as well as mixtures thereof.

Utility and Administration:

The compounds defined by structural formula (I) are useful as estrone sulfatase inhibitors and are therefore useful for the treatment of estrogen-dependent disorders, i.e., conditions or diseases that are estrogen-induced or estrogen stimulated. Since the present compounds can lower circulating estrogen levels, they can effectively prevent the biologically active estrogens from reaching endocrine tumors. In addition, since the present compounds can reduce estrogen biosynthesis in tumors capable of endogenous estrogen synthesis, the present compounds are capable of inducing remissions in breast cancer, including metastatic tumors. Furthermore, the present compounds have utility in the treatment of ovarian, uterine and pancreatic tumors as well as disease conditions such as galactorrhea, McCurne-Albright syndrome, benign breast disease, and endometriosis.

An important feature of the preferred novel compounds described herein is that neither they nor their hydrolysis products are estrogenic. They are therefore especially advantageous for the applications described above because their administration will not exacerbate the conditions which they are used to treat.

In further preferred embodiments, the present compounds and their hydrolysis products are anti-estrogenic. Thus the compounds may be employed as anti-estrogenic agents, and are therefore useful for treating a variety of estrogen-dependent disorders, i.e., those conditions or diseases that are either induced or stimulated by estrogen. Such conditions include, but are not limited to: breast cancer, including metastatic tumors; ovarian, uterine and pancreatic tumors; and disease conditions such as galactorrhea, McCurne-Albright syndrome, benign breast disease, and endometriosis.

The compounds may be conveniently formulated into pharmaceutical compositions composed of one or more of the compounds in association with a pharmaceutically acceptable carrier. See *Remington: The Science and Practice of Pharmacy*, 19th Ed. (Easton, Pa.: Mack Publishing Co., 1995), which discloses typical carriers and conventional methods of preparing pharmaceutical compositions which may be used to prepare formulations using the novel enzyme inhibitors of the invention. The compounds may also be administered in the form of pharmaceutically acceptable salts, or in the form of pharmaceutically acceptable esters, as explained in the preceding section.

The compounds may be administered orally, parenterally, transdermally, rectally, nasally, buccally, vaginally or via an implanted reservoir in dosage formulations containing conventional non-toxic pharmaceutically acceptable carriers, adjuvants and vehicles. The term "parenteral" as used herein is intended to include subcutaneous, intravenous, and intramuscular injection. The amount of active compound administered will, of course, be dependent on the subject being treated, the subject's weight, the manner of administration and the judgment of the prescribing physician. Generally, however, dosage will be in the range of approximately 0.01 mg/kg/day to 10.0 mg/kg/day, more preferably in the range of about 1.0 mg/kg/day to 5.0 mg/kg/day.

Depending on the intended mode of administration, the pharmaceutical compositions may be in the form of solid, semi-solid or liquid dosage forms, such as, for example, tablets, suppositories, pills, capsules, powders, liquids, suspensions, or the like, preferably in unit dosage form suitable for single administration of a precise dosage. The compositions will include, as noted above, an effective amount of the selected inhibitor in combination with a pharmaceutically acceptable carrier and, in addition, may include other pharmaceutical agents, adjuvants, diluents, buffers, etc.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc., an estrone sulfatase inhibitor as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington: The Science and Practice of Pharmacy*, referenced above.

For oral administration, the composition will generally take the form of a tablet or capsule, or may be an aqueous or nonaqueous solution, suspension or syrup. Tablets and capsules are preferred oral administration forms. Tablets and capsules for oral use will generally include one or more commonly used carriers such as lactose and corn starch. Lubricating agents, such as magnesium stearate, are also typically added. When liquid suspensions are used, the active agent is combined with emulsifying and suspending agents. If desired, flavoring, coloring and/or sweetening agents may be added as well. Other optional components for incorporation into an oral formulation herein include, but are not limited to, preservatives, suspending agents, thickening agents, and the like.

Parenteral administration, if used, is generally characterized by injection. Injectable formulations can be prepared in conventional forms, either as liquid solutions or suspensions, solid forms suitable for solution or suspension in liquid prior to injection, or as emulsions. Preferably, sterile injectable suspensions are formulated according to techniques known in the art using suitable dispersing or wetting agents and suspending agents. The sterile injectable formulation may also be a sterile injectable solution or a suspension in a nontoxic parenterally acceptable diluent or solvent. Among the acceptable vehicles and solvents that may be employed are water, Ringer's solution and isotonic sodium chloride solution. In addition, sterile, fixed oils are conventionally employed as a solvent or suspending medium. A more recently revised approach for parenteral administration involves use of a slow release or sustained release system, such that a constant level of dosage is maintained. See, e.g., U.S. Pat. No. 3,710,795.

The compounds of the invention may also be administered through the skin or mucosal tissue using conventional transdermal drug delivery systems, wherein the agent is contained within a laminated structure that serves as a drug delivery device to be affixed to the skin. In such a structure, the drug composition is contained in a layer, or "reservoir," underlying an upper backing layer. The laminated structure may contain a single reservoir, or it may contain multiple reservoirs. In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form.

The backing layer in these laminates, which serves as the upper surface of the device, functions as the primary structural element of the laminated structure and provides the device with much of its flexibility. The material selected for the backing material should be selected so that it is substantially impermeable to the active agent and any other materials that are present. The backing layer may be either occlusive or nonocclusive, depending on whether it is desired that the skin become hydrated during drug delivery. The backing is preferably made of a sheet or film of a preferably flexible elastomeric material. Examples of polymers that are suitable for the backing layer include polyethylene, polypropylene, polyesters, and the like.

During storage and prior to use, the laminated structure includes a release liner. Immediately prior to use, this layer is removed from the device to expose the basal surface thereof, either the drug reservoir or a separate contact adhesive layer, so that the system may be affixed to the skin. The release liner should be made from a drug/vehicle impermeable material.

Transdermal drug delivery devices may be fabricated using conventional techniques, known in the art, for example by casting a fluid admixture of adhesive, drug and vehicle onto the backing layer, followed by lamination of the release liner. Similarly, the adhesive mixture may be cast onto the release liner, followed by lamination of the backing layer. Alternatively, the drug reservoir may be prepared in the absence of drug or excipient, and then loaded by soaking in a drug/vehicle mixture.

The laminated transdermal drug delivery systems may in addition contain a skin permeation enhancer. That is, because the inherent permeability of the skin to some drugs may be too low to allow therapeutic levels of the drug to pass through a reasonably sized area of unbroken skin, it is necessary to coadminister a skin permeation enhancer with such drugs. Suitable enhancers are well known in the art and include, for example, dimethylsulfoxide (DMSO), dimethyl formamide (DMF), N,N-dimethylacetamide (DMA), decyl-methylsulfoxide ($C_{10}MSO$), $C_2$–$C_6$ alkanediols, and the 1-substituted azacycloheptan-2-ones, particularly 1-n-dodecylcyclaza-cycloheptan-2-one (available under the trademark Azone® from Whitby Research Incorporated, Richmond, Va.), alcohols, and the like.

Alternatively, the pharmaceutical compositions of the invention may be administered in the form of suppositories for rectal administration. These can be prepared by mixing the agent with a suitable non-irritating excipient which is solid at room temperature but liquid at the rectal temperature and therefore will melt in the rectum to release the drug. Such materials include cocoa butter, beeswax and polyethylene glycols.

The pharmaceutical compositions of the invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Preferred formulations for vaginal drug delivery are ointments and creams. Ointments are semisolid preparations which are typically based on petrolatum or other petroleum derivatives. Creams containing the selected active agent, are, as known in the art, viscous liquid or semisolid emulsions, either oil-in-water or water-in-oil. Cream bases are water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery. As with other carriers or vehicles, an ointment base should be inert, stable, nonirritating and nonsensitizing. Also preferred are vaginal suppositories. Suppositories may be formulated using conventional means, e.g., compaction, compression-molding or the like, and will contain carriers suited to vaginal drug delivery, typically a bioerodible material which provides for the desired drug release profile.

Formulations for buccal administration include tablets, lozenges, gels and the like. Alternatively, buccal administration can be effected using a transmucosal delivery system.

Process for Preparation:

The compounds of the invention may be prepared in high yield using relatively simple, straightforward methods as exemplified in the experimental section herein. Syntheses of representative compounds are detailed in Examples 1 through 32. Reference may also be had to co-pending, commonly assigned U.S. patent application Ser. No. 08/998,877, entitled "Novel Anti-Estrogenic Steroids, and Associated Pharmaceutical Compositions and Methods of Use," inventors Tanabe et al.(filed on even date herewith.)

EXPERIMENTAL

The practice of the present invention will employ, unless otherwise indicated, conventional techniques of synthetic organic chemistry, biological testing, and the like, which are within the skill of the art. Such techniques are explained fully in the literature. See, e.g., Fieser et al., *Steriods* (New York: Reinhold, 1959), Djerassi, *Steroid Reactions: An Outline for Organic Chemists* (San Francisco: Holden-Day, 1963), and Fried et al., *Organic Reactions in Steroid Chemistry*, vols. 1 and 2 (New York: Reinhold, 1972), for detailed information concerning steroid-related synthetic procedures. Reference may be had to MacIndoe et al., *Endocrinology* 123(3):1281–1287 (1988), Duncan et al., *Cancer Res.* 53:298–303 (1993), and Yue et al., *J. Steroid Biochem.* 44:671–673 (1993), for a description of the biological testing procedures useful to evaluate compounds such as those described and claimed herein. All patents, patent applications, and publications mentioned herein, both supra and infra, are hereby incorporated by reference.

It is to be understood that while the invention has been described in conjunction with the preferred specific embodiments thereof, that the description above as well as the examples which follow are intended to illustrate and not limit the scope of the invention. Other aspects, advantages and modifications within the scope of the invention will be apparent to those skilled in the art to which the invention pertains.

In the following examples, efforts have been made to ensure accuracy with respect to numbers used (e.g., amounts, temperature, etc.) but some experimental error and deviation should be accounted for. Unless indicated otherwise, temperature is in degrees C. and pressure is at or near atmospheric. All solvents were purchased as HPLC grade, and all reactions were routinely conducted under an inert atmosphere of argon unless otherwise indicated. All reagents were obtained commercially unless otherwise indicated. Estrone and estradiol were purchased from Berlichem U.S.; ethynyl estradiol was purchased from Akzo Nobel. NMR analyses were conducted on either a Varian Gemini 300 and were referenced to chloroform at δ 7.27. FTIR spectra were recorded on a Perkin-Elmer 1610.

The following scheme illustrates the synthetic steps carried out in Examples 1 and 2 to make the estrone sulfatase inhibitors (5) and (7):

Scheme 1

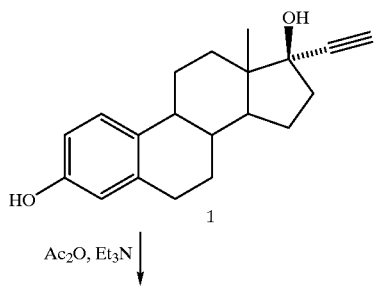

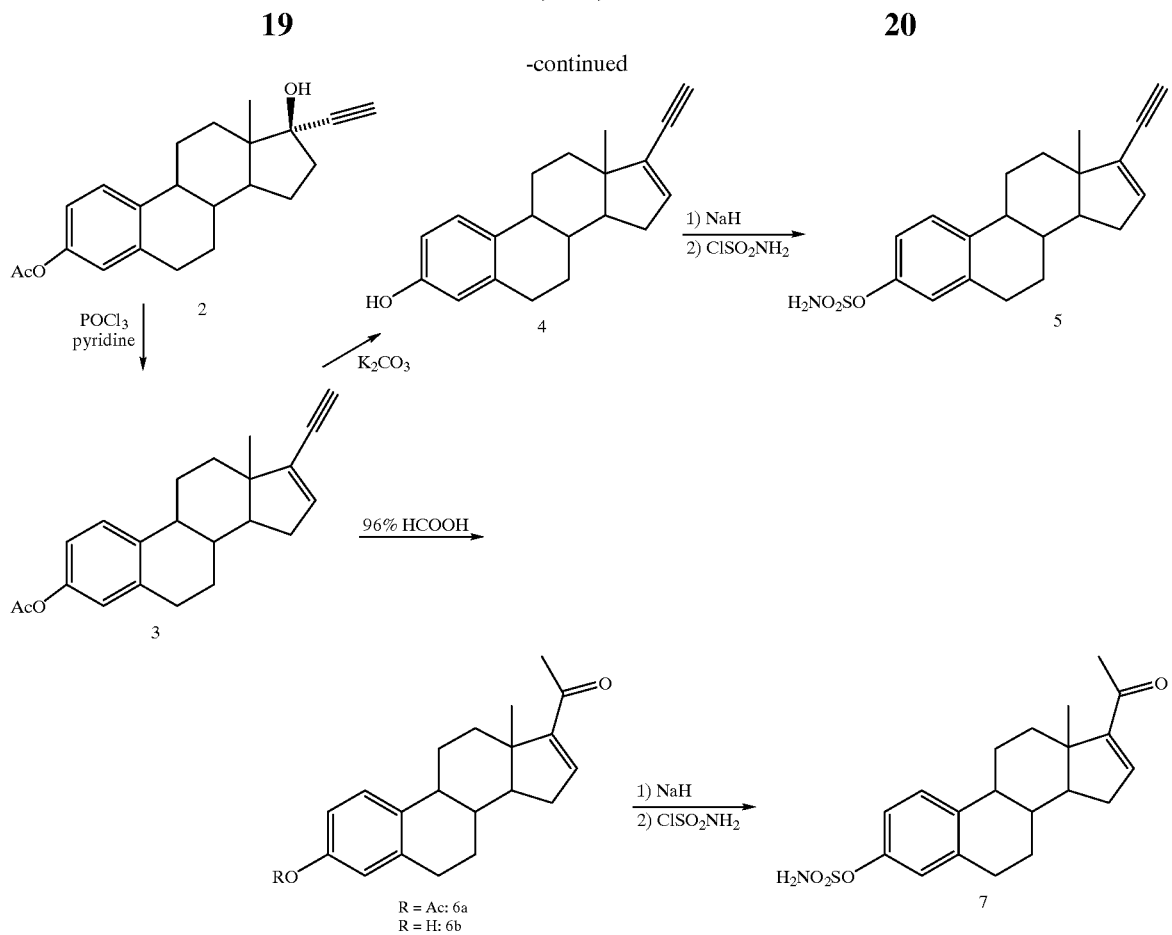

EXAMPLE 1

Preparation of 19-Norpregna-1,3,5(10),16-tetraen-20-yne-3-O-sulfamate (5)

(a) Synthesis of Ethynylestradiol 3-O-acetate (2):

To a solution of ethynylestradiol (1, 5.92 g, 20 mmol) in tetrahydrofuran (THF) (30 mL) and CH$_2$Cl$_2$ (70 mL) were added triethylamine (6.8 ml, 50 mmol) and acetic anhydride (2.8 ml, 30 mmol); the mixture was then stirred for 17 h at room temperature. Saturated aqueous NH$_4$Cl was added to the reaction mixture, which was then extracted with ethyl acetate (EtOAc). The combined organic layers were washed with H$_2$O, saturated aqueous NaCl, and then dried (Na$_2$SO$_4$). The desiccant was filtered and the solvent was evaporated at reduced pressure. The residue was washed with Et$_2$O to afford 6.08 g of 2 (90% yield) mp: 147–148° C.

$^1$H NMR: δ 7.29 (d, 1H, aromatic), 6.90–6.75 (m, 2H, aromatic), 2.60 (s, 1H, —C≡CH), 2.28 (s, 3H, —OCOCH$_3$), 0.88 (s, 3H, 18-CH$_3$).

(b) Synthesis of 19-Norpregna-1,3,5(10),16-tetraen-20-yn-3-ol 3-O-acetate (3):

To a solution of ethynylestradiol 3-O-acetate (2, 3.05 g, 9.0 mmol) in pyridine (25 mL) was added phosphorousoxychloride (1.7 ml, 18 mmol) and stirred for 2 h at 110° C. Afterwards, the reaction mixture was cooled to room temperature, poured into ice (100 g) and acidified with 5 N HCl, and then extracted with EtOAc. The combined organic layers were washed with H$_2$O, saturated aqueous NaCl, and then dried (Na$_2$SO$_4$). The desiccant was filtered and the solvent was evaporated at reduced pressure. The residue was purified by column chromatography (silica gel) using n-hexane:EtOAc (15:1→10:1, v/v) to afford 1.83 g of 3 (64% yield) mp: 104–106° C.

$^1$H NMR: δ 7.28 (d, 1H, aromatic), 6.95–6.75 (m, 2H aromatic), 6.22–6.10 (m, 1H, 16-H), 3.09 (s, 1H, —C≡CH), 2.28 (s, 3H, —OCOCH$_3$), 0.88 (s, 3H, 18—CH$_3$).

(c) Synthesis of 19-Norpregna-1,3,5(10),16-tetraen-20-yn-3-ol (4):

To a solution of 19-norpregna-1,3,5(10),16-tetraen-20-yn-3-ol 3-O-acetate (3, 0.670 g, 2.1 mmol) in THF (2.0 mL) and methanol (MeOH) (5.0 mL) was added potassium carbonate (0.290 g, 2.1 mmol) and stirred for 1 h at room temperature. The reaction mixture was acidified with 1 N HCl, and extracted with EtOAc. The combined organic layers were washed with H$_2$O, saturated aqueous NaCl, and then dried (Na$_2$SO$_4$). The desiccant was filtered and the solvent was evaporated at reduced pressure. The residue was purified by column chromatography (silica gel) using n-hexane:EtOAc (5:1→2:1, v/v) to afford 0.573 g of (4) (99% yield) mp: 158–159° C.

$^1$H NMR: δ 7.15 (d, 1H, aromatic), 6.68–6.52 (m, 2H, aromatic), 6.20–6.10 (m, 1H, 16-H), 4.55 (s, 1H, —OH), 3.09 (s, 1H, —C≡CH), 0.88 (s, 3H, 18-CH$_3$); MS (EI): m/z 278 (M$^+$).

(d) Synthesis of 19-Norpregna-1,3,5(10),16-tetraen-20-yne-3-O-sulfamate (5):

To a solution of chlorosulfonyl isocyanate (0.22 ml, 2.5 mmol) in CH$_2$Cl$_2$ (1.0 mL) was added formic acid (0.5 ml of a CH$_2$Cl$_2$ solution, 5.0 M, 2.5 mmol) at 0° C. The reaction mixture was warmed to room temperature and stirred for 1 h. To a solution of 19-norpregna-1,3,5(10),16-tetraen-20-yn-3-ol (4, 0.139 g, 0.5 mmol) in DMF (3.0 mL) was added sodium hydride (0.100 g of a mineral oil dispersion, 60%, 2.5 mmol) at 0° C. The reaction mixture was stirred for 1 h, and the chlorosulfonyl isocyanate in formic acid was then added, and stirring continued for 2 h. The reaction mixture was quenched with saturated aqueous NH₄Cl at 0° C., and extracted with EtOAc. The combined organic layers were washed with H₂O, saturated aqueous NaCl, and then dried (Na₂SO₄). The desiccant was filtered and the solvent was evaporated at reduced pressure. The residue was purified by column chromatography (silica gl) using n-hexane:EtOAc (3:1→2:1, v/v) to afford 0.142 g of 5, (79% yield) mp: 210° C. (decomposed).

¹H NMR: δ 7.31 (d, 1H, aromatic), 7.15–7.00 (m, 2H, aromatic), 6.18–6.12 (m, 1H, 16-H), 4.91 (s, 2H, —NH₂), 3.09 (s, 1H, —C≡CH), 0.88 (s, 3H, 18-CH₃); MS (EI): m/z 357 (M⁺).

EXAMPLE 2

Preparation of 19-Norpregna-1,3,5(1), 16-tetraen-20-one-3-O-sulfamate (7)

(a) Synthesis of 19-Norpregna-1,3,5(10),16-tetraen-20-yn-3-ol 3-O-acetate (3):

The procedure described in steps (a) and (b) of Example 1 above was used to obtain 3.

(b) Synthesis of 3-Hydroxy-19-norpregna-1,3,5(10,16-tetraen-20-one 3-O-acetate (6a) and 3-Hydroxy-19-norpregna-1,3,5(10),16-tetraen-20-one (6b):

A solution of 19-norpregna-1,3,5(10),16- tetraen-20-yn-3-ol 3-O-acetate (3, 1.05 g, 3.3 mmol) in 96% formic acid (30 mL) was stirred for 30 min at 100° C. Afterwards, the reaction mixture was cooled to room temperature, poured into ice (100 g) and stood for 18 h at 0° C. The precipitate was collected by filtration and washed with H₂O, and purified by column chromatography (silica gel) using n-hexane:EtOAc (5:16→2:1, v/v) to afford 0.418 g of 6a (37% yield) mp: 154–155° C., and 0.267 g of 6b (27% yield) mp: 243–244° C.

6a: ¹H NMR: δ 7.28 (d, 1H, aromatic), 6.95–6.68 (m, 3H, aromatic, 16-H), 2.28 (s, 3H, 21-CH₃), 2.28 (s, 3H, —OCOCH₃), 0.92 (s, 3H, 18—CH₃).

6b: ¹H NMR: δ 7.15 (d, 1H, aromatic), 6.80–6.72 (m, 1H, 16-H), 6.68–6.53 (m, 2H, aromatic), 2.29 (s, 3H, 21-CH₃), 0.92 (s, 3H, 18-CH₃); MS (EI): m/z 296 (M⁺).

(c) Synthesis of 19-Norpregna-1,3,5(10),16-tetraen-20-one-3-O-sulfamate (7):

Beginning with 3-hydroxy-19-norpregna-1,3,5(10),16-tetraen-20-one (6b, 0.148 g, 0.50 mmol), by using the procedure described in step (d) of Example 1 above, 0.139 g of (7) (74% yield) mp: 189–190° C. was obtained after chromatography (n-hexane:EtOAc 2:1→3:2, v/v). ¹H NMR: δ 7.31 (d, 1H, aromatic), 7.13–7.00 (m, 2H, aromatic), 6.78–6.70 (m, 1H, 16-H), 4.97 (s, 2H, —NH₂), 2.29 (s, 3H, 21-CH₃), 0.92 (s, 3H, 18-CH₃); MS (EI): m/z 375 (M⁺).

EXAMPLE 3

Preparation of 19-Norpregna-1,3,5(10)trien-20-one-3-O-sulfamate (10)

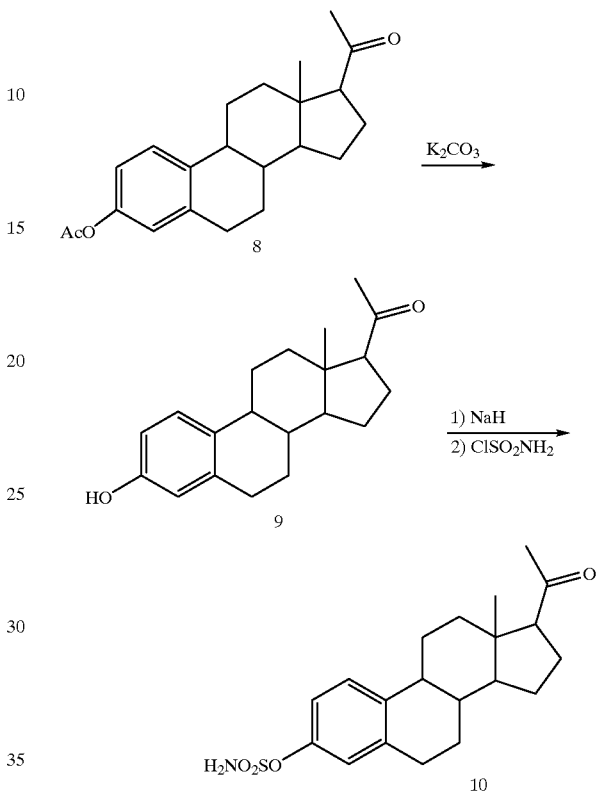

Scheme 2

(a) Synthesis of 3-Hydroxy-19-norpregna-1,3,5(10)trien-20-one (9):

To a solution of 3-hydroxy-19-norpregna-1,3,5(10)trien-20-one 3-O-acetate (8, 0.340 g, 1.0 mmol) in THF (5.0 mL) and MeOH (5.0 mL) was added potassium carbonate (0.138 g, 1.0 mmol) at 0° C. The reaction mixture was stirred for 2 h, and quenched with saturated aqueous NH₄Cl at 0° C., and extracted with EtOAc. The combined organic layers were washed with H₂O, saturated aqueous NaCl, and then dried (Na₂SO₄). The desiccant was filtered and the solvent was evaporated at reduced pressure. The residue was washed with Et₂O to afford 0.267 g of 9 (90% yield) mp: 237–238° C.

¹H NMR: δ 7.15 (d, 1H, aromatic), 6.67–6.52 (m, 2H, aromatic), 4.76 (s, 1H, —OH), 2.62 (t, 1H,17α-H), 2.16 (s, 3H, 21-CH₃), 0.66 (s, 3H, 18-CH₃); MS (EI): m/z 298 (M⁺).

(b) Synthesis of 19-Norpregna-1,3,5(10)trien-20-one-3-O-sulfamate (10):

To a solution of chlorosulfonyl isocyanate (0.22 mL, 2.5 mmol) in CH₂Cl₂ (1.0 mL) was added formic acid (0.5 mL of a CH₂Cl₂ solution, 5.0 M, 2.5 mmol) at 0° C. The reaction mixture was warmed to room temperature and stirred for 1 h. To a solution of 3-hydroxy-19-norpregna-1,3,5(10)trien-20-one (9, 0.149 g, 0.5 mmol) in DMF (3.0 mL) was added sodium hydride (0.100 g of a mineral oil dispersion, 60%, 2.5 mmol) at 0° C. The reaction mixture was stirred for 1 h, and the chlorosulfonyl isocyanate in formic acid was added, and stirring continued for 2 h. The reaction mixture was quenched with saturated aqueous NH₄Cl at 0° C., and extracted with EtOAc. The combined organic layers were washed with H₂O, saturated aqueous NaCl, and then dried (Na₂SO₄). The desiccant was filtered and the solvent was evaporated at reduced pressure. The residue was washed with Et₂O to afford 0.151 g of 10 (80% yield) mp: 189–190° C.

¹H NMR: δ 7.31 (d, 1H, aromatic), 7.13–7.00 (m, 2H, aromatic), 4.89 (s, 2H, —NH₂), 2.61 (t, 1H,17α-H), 2.16 (s, 3H, 21-CH₃), 0.66 (s, 3H, 18-CH₃); MS (EI): m/z 377 (M⁺)

The following scheme illustrates the synthetic steps carried out in Examples 4 through 9 to make the anti-estrogenic compounds (13), (15), (17), (19), (21) and (23):

mL of a CH₂Cl₂ solution, 5.0 M, 2.5 mmol) at 0° C. The reaction mixture was warmed to room temperature and stirred for 1 h. To a solution of [17(20)Z]-19-norpregna-1, 3,5(10),17(20)-tetraene-3-ol (12, 0.141 g, 0.50 mmol) in DMF (3.0 mL) was added sodium hydride (0.100 g of a mineral oil dispersion, 60%, 2.5 mmol) at 0° C. The reaction mixture was stirred for 1 h, the chlorosulfonyl isocyanate in formic acid was added, and stirring continued for 2 h. The reaction mixture was quenched with saturated aqueous NH₄Cl at 0° C., and extracted with EtOAc. The combined organic layers were washed with H₂O, saturated aqueous

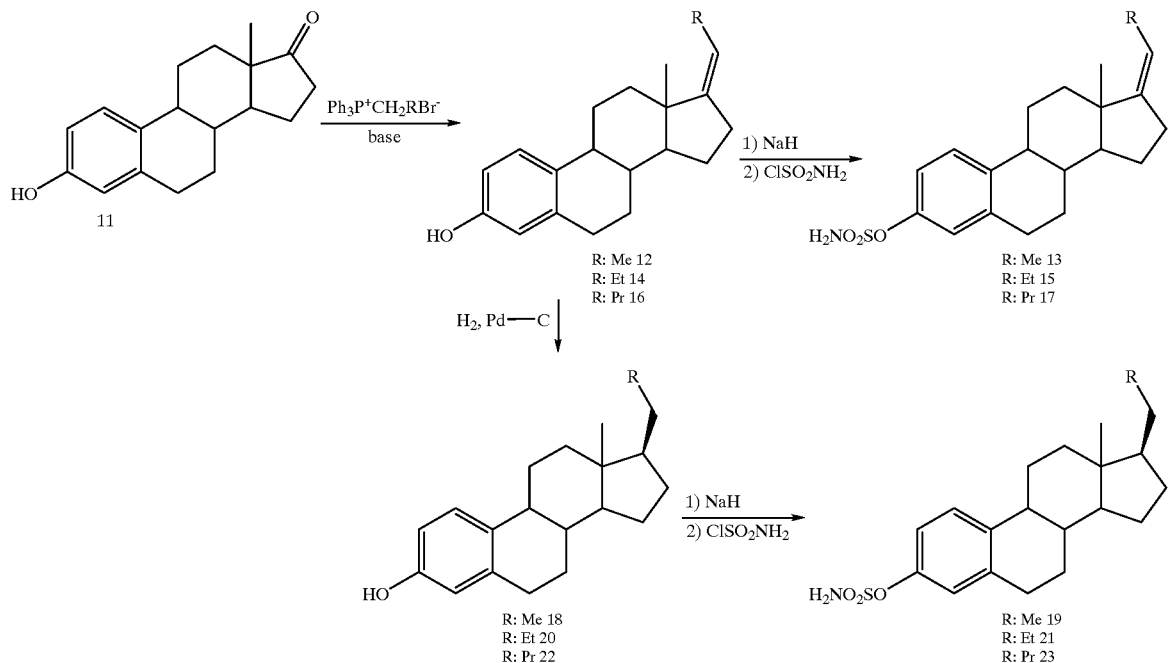

Scheme 3

EXAMPLE 4

Synthesis of [17(20)Z]-19-Norpregna-1,3,5(10), 17 (20)-tetraene-3-O-sulfamate (13)

(a) Synthesis of [17(20)Z]-19-Norpregna-1,3,5(10),17,(20)-tetraen-3-ol (12):

To a suspension of ethyltriphenylphosphonium bromide (4.64 g, 12.5 mmol) in THF (40 mL) was added potassium tert-butoxide (1.35 g, 12 mmol) and stirred for 30 min at room temperature. Estrone (11, 1.35 g, 5.0 mmol) was then added, and the mixture was then stirred for 24 h at room temperature. The reaction mixture was quenched with saturated aqueous NH₄Cl at 0° C. and extracted with EtOAc. The combined organic layers were washed with H₂O, saturated aqueous NaCl, and then dried (Na₂SO₄). The desiccant was filtered and the solvent was evaporated at reduced pressure. The residue was purified by column chromatography (silica gel) using n-hexane:EtOAc (5:1→2:1, v/v) to afford 1.03 g of 12 (72% yield) mp: 138–139° C.

¹H NMR: δ 7.16 (d, 1H, aromatic), 6.68–6.50 (m, 2H, aromatic), 5.22–5.08 (m, 1H, =C<u>H</u>—CH₃), 4.48 (s, 1H, —OH), 1.72–1.65 (m, 3H, =CH—C<u>H</u>₃), 0.91 (s, 3H, 18-CH₃); MS (EI): m/z 282 (M⁺).

(b) Synthesis of [17(20)Z]-19-Norpregna-1,3,5(10),17(20)-tetraene-3-O-sulfamate (13):

To a solution of chlorosulfonyl isocyanate (0.22 mL, 2.5 mmol) in CH₂Cl₂ (1.0 10 mL) was added formic acid (0.5

NaCl, and then dried (Na₂SO₄). The desiccant was filtered and the solvent was evaporated at reduced pressure. The residue was purified by column chromatography (silica gel) using n-hexane:CHCl₃:EtOAc (5:5:1→3:3:1, v/v/v) to afford 0.181 g of 13 (100% yield) mp: 131–132° C.

¹H NMR: δ 7.31 (d, 1H, aromatic), 7.18–6.95 (m, 2H, aromatic), 5.25–5.10 (m, 1H, =CH—CH₃), 4.96 (s, 2H, —NH₂), 1.69 (d, 3H, =C<u>H</u>—CH₃), 0.91 (s, 3H, 18-CH₃); MS (DCI): m/z 379 (M⁺+NH₄⁺), 362 (M⁺+H).

EXAMPLE 5

Synthesis of [17(20))Z]-Propylideneestra-1,3,5(10)-triene-3-O-sulfamate (15)

(a) Synthesis of [17(20)Z]-Propylideneestra-1,3,5(1)-trien-3-ol (14):

To sodium hydride (1.20 g of a mineral oil dispersion, 60%, 30 mmol) was added DMSO (100 mL) and the mixture stirred for 1 h at 75° C. Propyltriphenyl-phosphonium bromide (12.3 g, 32.0 mmol) was then added, and stirring continued for 30 min at room temperature. Estrone (11, 2.70 g, 10 mmol) was added to the reaction mixture, and it was then stirred for 4 days at 80° C. The reaction mixture was quenched with saturated aqueous NH₄Cl at 0° C. and extracted with Et₂O. The combined organic layers were washed with H₂O, saturated aqueous NaCl, and then dried (Na$_2$SO$_4$). The desiccant was filtered and the solvent was evaporated at reduced pressure. The residue was purified by column chromatography (silica gel) using n-hexane:EtOAc (10:1→1:1, v/v) to afford 1.30 g of 14 (44% yield) and 1.05 g of the starting material 11 (39% yield) mp: 149–151° C.

$^1$H NMR: δ 7.15 (d, 1H, aromatic), 6.68–6.50 (m, 2H, aromatic), 5.12–5.00 (m, 1H, =C$\underline{H}$—CH$_2$—), 4.57 (s, 1H, —OH), 0.96 (t, 3H, 23-CH$_3$), 0.90 (s, 3H, 18-CH$_3$); MS (EI): m/z 296 (M$^+$).

(b) Synthesis of [17(20)Z]-Propylideneestra-1,3,5(10)-trien-3-O-sulfamate (15):

Beginning with [17(20)Z]-propylideneestra-1,3,5(10)-trien-3-ol (14, 0.148 g, 0.50 mmol), by using the procedure described in step (b) of Example 4 above, 0.145 g of 15 (77% yield; mp: 120–121° C.) was obtained after chromatography (n-hexane:EtOAc 5:1→2:1, v/v).

$^1$H NMR: δ 7.31 (d, 1H, aromatic), 7.13–6.98 (m, 2H, aromatic), 5.12–5.00 (m, 1H, =C$\underline{H}$—CH$_2$—), 4.94 (s, 2H, —NH$_2$), 0.96 (t, 3H, 23-CH$_3$), 0.90 (s, 3H, 18-CH$_3$; MS (EI): m/z 375 (M$^+$).

EXAMPLE 6

Preparation of [17(20)]-19,21-Dinorchola-1,3,5(10) 17(20)-tetraene-3-O-sulfamate (17)

(a) Synthesis of [17(20)Z]-19,21-Dinorchola-1,3,5(10)17 (20)-tetraen-3-ol (16):

To a suspension of butyltriphenylphosphonium bromide (12.8 g, 32.0 mmol) in THF (100 mL) was added potassium tert-butoxide (3.37 g, 30 mmol) and stirred for 30 min at room temperature. Estrone (11, 2.70 g, 10 mmol) was added to the reaction mixture, and stirring continued for 5 days at 80° C. The reaction mixture was quenched with saturated aqueous NH$_4$Cl at 0° C. and extracted with EtOAc. The combined organic layers were washed with H$_2$O, saturated aqueous NaCl, and then dried (Na$_2$SO$_4$). The desiccant was filtered and the solvent was evaporated at reduced pressure. The residue was purified by column chromatography (silica gel) using n-hexane:EtOAc (10:1→2:1, v/v) to afford 2.45 g of 16 (79% yield) mp: 85–86° C.

$^1$H NMR: δ 7.15 (d, 1H, aromatic), 6.70–6.52 (m, 2H, aromatic), 5.13–5.00 (m, 1H, =C$\underline{H}$—CH$_2$—), 4.49 (s, 1H, —OH), 0.91 (t, 3H, 24-CH$_3$), 0.90 (s, 3H, 18-CH$_3$); MS (EI): m/z 310 (M$^+$).

(b) Synthesis of [17(20)Z]-19,21-Dinorchola-1,3,5(10)17 (20)-tetraene-3-O-sulfamate (17):

Beginning with [17(20)Z]-19,21- dinorchola-1,3,5(10)17 (20)-tetraen-3-ol (16, 0.176 g, 0.57 mmol), by using the procedure described in step (b) of Example 4 above, 0.173 g of 17 (78% yield; mp: 117–118° C.) was obtained after chromatography (n-hexane:EtOAc 5:1→3:1, v/v).

$^1$H NMR: δ 7.30 (d, 1H, aromatic), 7.15–6.97 (m, 2H, aromatic), 5.20–4.85 (m, 3H, =C$\underline{H}$—CH$_2$—, and —NH$_2$), 0.91 (t, 3H, 24-CH$_3$), 0.90 (s, 3H, 18-CH$_3$); MS (EI): m/z 389 (M$^+$).

EXAMPLE 7

Preparation of 19-Norpregna-1,3,5(10)-triene-3-O-sulfamate (19)

(a) Synthesis of [17(20)Z]-19-Norpregna-1,3,5(10),17,(20)-tetraen-3-ol (12):

By using the procedure described in step (a) of Example 4 above, 12 was obtained from 11.

(b) Synthesis of 19-Norpregna-1,3,5(10)-trien-3-ol (18):

To a solution of [17(20)Z]-19-norpregna-1,3,5(10),17 (20)-tetraen-3-ol (12, 0.565 g, 2.00 mmol) in EtOAc (10 mL) was added 10% palladium on carbon (0.100 g). The reaction mixture was stirred for 2 h under a hydrogen atmosphere at room temperature. After the catalyst was filtered, the solvent was evaporated at reduced pressure. The residue was purified by column chromatography (silica gel) using n-hexane:EtOAc (5:1, v/v) to afford 0.483 g of 18 (85% yield) mp: 112–113° C.

$^1$H NMR: δ 7.15 (d, 1H, aromatic), 6.67–6.50 (m, 2H, aromatic), 0.90 (t, 3H, 21-CH$_3$), 0.60 (s, 3H, 18-CH$_3$); MS (EI): m/z 284 (M$^+$).

(c) Synthesis of 19-Norpregna-1,3,5(10)-triene-3-O-sulfamate (19):

Beginning with 19-norpregna-1,3,5(10)- trien-3-ol (18, 0.284 g, 1.00 mmol), by using the procedure described in step (b) of Example 4 above, 0.279 g of 19 (77% yield; mp: 167–168° C.) was obtained after chromatography (n-hexane:EtOAc 3:1→2:1, v/v).

$^1$H NMR: δ 7.31 (d, 1H, aromatic), 7.12–6.98 (m, 2H, aromatic), 4.90 (s, 2H, —NH$_2$), 0.90 (t, 3H, 21-CH$_3$), 0.61 (s, 3H, 18-CH$_3$); MS (DCI): m/z 381 (M$^+$+NH$_4^+$); HRMS calcd. for C$_{20}$H$_{28}$N$_1$O$_3$S$_1$, 362.1790; found, 362.1812.

EXAMPLE 8

Preparation of 17β-Propylestra-1,3,5(10)-triene-3-O-sulfamate (21)

(a) Synthesis of [17(20)Z]-Propylideneestra-1,3,5(1)-trien-3-ol (14):

By using the procedure described in step (a) of Example 5 above, 14 was obtained from 11.

(b) Synthesis of 17β-Propylestra-1,3,5(10)-trien-3-ol (20):

Beginning with [17(20)Z]-propylideneestra-1,3,5(10)-trien-3-ol (14, 0.371 g, 1.25 mmol), by using the procedure described in step (b) of Example 7 above, 0.311 g of 20 (83% yield; mp: 130–131° C.) was obtained after chromatography (n-hexane:EtOAc 10:1→5:1, v/v).

$^1$H NMR: δ 7.15 (d, 1H, aromatic), 6.70–6.52 (m, 2H, aromatic), 4.49 (s, 1H, —OH), 0.90 (t, 3H, 23-CH$_3$), 0.60 (s, 3H, 18-CH$_3$); MS (EI): m/z 298 (M$^+$).

(c) Synthesis of 17β-Propylestra-1,3,5(10)-triene-3-O-sulfamate (21):

Beginning with 17β-propylestra-1,3,5(10)-trien-3-ol (20, 0.149 g, 0.50 mmol), by using the procedure described in step (b) of Example 4 above, 0.184 g of 21 (97% yield; mp: 170–171° C.) was obtained after chromatography (n-hexane:EtOAc 5:1→2:1, v/v).

$^1$H NMR: δ 7.31 (d, 1H, aromatic), 7.15–7.00 (m, 2H, aromatic), 4.89 (s, 2H, —NH$_2$), 0.91 (t, 3H, 23-CH$_3$), 0.61 (s, 3H, 18-CH$_3$); MS (EI): m/z 377 (M$^+$).

EXAMPLE 9

Preparation of 19,21-Dinorchola-1,3,5(10)-triene-3-O-sulfamate (23)

(a) Synthesis of [17(20)Z]-19,21-Dinorchola-1,3,5(10)17 (20)-tetraen-3-ol (16):

By using the procedure described in step (a) of Example 6 above, 16 was obtained from 11.

(b) Synthesis of 19,21-Dinorchola-1,3,5(10)-trien-3-ol (22):

Beginning with [17(20)Z]-19,21-dinorchola-1,3,5(10)17 (20)-tetraen-3-ol (16, 0.473 g, 1.52 mmol), 0.367 g of 22 (77% yield; mp: 97–98° C.) was obtained after chromatography (n-hexane:EtOAc 10:1, v/v).

$^1$H NMR: δ 7.16 (d, 1H, aromatic), 6.70–6.50 (m, 2H, aromatic), 4.56 (s, 1H, —OH), 0.90 (t, 3H, 24-CH$_3$), 0.61 (s, 3H, 18-CH$_3$); MS (EI): m/z 312 (M$^+$).

(c) Synthesis of 19,21-Dinorchola-1,3,5(10)-triene-3-O-sulfamate (23):

Beginning with 19,21-dinorchola-1,3,5(10)-trien-3-ol (22, 0.177 g, 0.57 mmol), by using the procedure described in step (b) of Example 4 above, there was obtained 0.198 g of 23 (89% yield; mp: 144–145° C.) after chromatography (n-hexane:EtOAc 5:1° 2:1, v/v).

$^1$H NMR: δ 7.31 (d, 1H, aromatic), 7.13–6.97 (m, 2H, aromatic), 4.90 (s, 2H, —NH$_2$), 0.90 (t, 3H, 24-CH$_3$), 0.61 (s, 3H, 18-CH$_3$); MS (EI): m/z 391 (M$^+$).

EXAMPLE 10

Preparation of 3-tert-Butyldimethylsilyloxy-17α-ethenylestra-1,3,5(10)-trien-17β-ol (28)

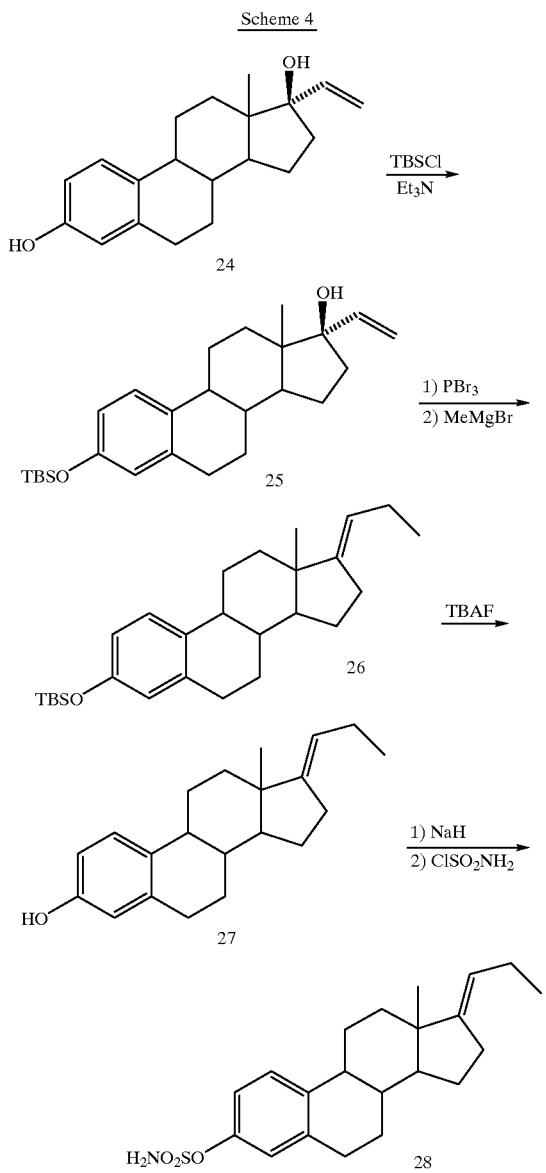

(a) Synthesis of 3-tert-Butyldimethylsilyloxy-17α-ethenylestra-1,3,5(10)-trien-17β-ol (25):

To a solution of 17α-ethenylestradiol (24, 0.298 g, 1.0 mmol) in 1,2-dichloroethane (5.0 mL) and THF (1.0 mL) were added triethylamine (0.35 mL, 2.5 mmol) and tert-butyldimethylchlorosilane (0.226 g, 1.5 mmol) and 4-dimethylaminopyridine (0.006 g, 0.05 mmol) at room temperature. The reaction mixture was stirred for 2 days, diluted with EtOAc, washed with H$_2$O, saturated aqueous NaCl, and then dried (Na$_2$SO$_4$). The desiccant was filtered and the solvent was evaporated at reduced pressure. The residue was purified by column chromatography (silica gel) using n-hexane:EtOAc (5:1→3:1, v/v) to afford 0.358 g of (87% yield) mp: 127–128° C.

$^1$H NMR: δ 7.10 (d, 1H, aromatic), 6.67–6.52 (m, 2H, aromatic), 6.12 (dd, 1H, —C$\underline{H}$=CH$_2$), 5.25–5.13 (m, 2H, —CH=C$\underline{H}_2$), 0.97 (s, 9H, —C(CH$_3$)$_3$), 0.9 (s, 3H, 18-CH$_3$), 0.18 (s, 6H, —Si(CH$_3$)$_2$).

(b) Synthesis of 3-tert-Butyldimethylsilyloxy-[17(20)E]-propylideneestra-1,3,5(10)-triene (26):

To a solution of phosphorous tribromide (4.5 mL of a CH$_2$Cl$_2$ solution, 1.0 M, 4.5 mmol) in toluene (6.0 mL) was added a solution of 3-tert-butyldimethylsilyloxy-17α-ethenylestra-1,3,5(10)-trien-17β-ol (25, 1.86 g, 4.5 mmol) and pyridine (0.40 mL, 5.0 mmol) in toluene (25 mL) at 0° C. The reaction mixture was stirred for 2 h, quenched with H$_2$O and extracted with EtOAc. The combined organic layers were washed with H$_2$O, saturated aqueous NaCl, and then dried (Na$_2$SO$_4$). The desiccant was filtered and the solvent was evaporated at reduced pressure. The residue was dissolved in THF (20 mL) and added methylmagnesium-bromide (7.5 mL of a Et$_2$O solution, 3.0 M, 22.5 mmol) at 0° C. The reaction mixture was stirred for 19 h at room temperature, quenched with H$_2$O at 0° C. and extracted with EtOAc. The combined organic layers were washed with H$_2$O, saturated aqueous NaCl, and then dried (Na$_2$SO$_4$). The residue was purified by column chromatography (silica gel) using n-hexane:CHCl$_3$ (5:1→3:1, v/v) to afford 1.06 g of 26 (57% yield) mp: 59–60° C.

$^1$H NMR: δ 7.13 (d, 1H, aromatic), 6.66–6.51 (m, 2H, aromatic), 5.08–4.95 (m, 1H, =C$\underline{H}$—CH$_2$—), 0.98 (s, 9H, —C(CH$_3$)$_3$), 0.93 (t, 3H, 23-CH$_3$), 0.78 (s, 3H, 18-CH$_3$), 0.18 (s, 6H, —Si(CH$_3$)$_2$).

(c) Synthesis of [17(20)E]-Propylideneestra-1,3,5(10)-trien-3-ol (27):

To a solution of 3-tert-butyldimethylsilyloxy-[17(20)E]-propylideneestra-1,3,5(10)-triene (26, 0.821 g, 2.0 mmol) in THF (20 mL) was added tetrabutylammonium fluoride (2.4 mL of a THF solution, 1.0 M, 2.4 mmol) at 0° C. The reaction mixture was stirred for 1 h, diluted with EtOAc, washed with H$_2$O, saturated aqueous NaCl, and then dried (Na$_2$SO$_4$). The desiccant was filtered and the solvent was evaporated at reduced pressure. The residue was purified by column chromatography (silica gel) using n-hexane:EtOAc (10:1→5:1, v/v) to afford 0.598 g of 27 (100% yield) mp: 105–106° C.

$^1$H NMR: δ 7.17 (d, 1H, aromatic), 6.67–6.52 (m, 2H, aromatic), 5.06–4.95 (m, 1H, =C$\underline{H}$—CH$_2$—), 4.53 (s, 1H, —OH), 0.95 (t, 3H, 23-CH$_3$), 0.78 (s, 3H, 18-CH$_3$); MS (EI): m/z 296 (M$^+$).

(d) Synthesis of [17(20)E]-Propylideneestra-1,3,5(10)-triene-3-O-sulfamate (28):

To a solution of chlorosulfonyl isocyanate (0.22 mL, 2.5 mmol) in CH$_2$Cl$_2$ (1.0 mL) was added formic acid (0.5 mL of a CH$_2$Cl$_2$ solution, 5.0 M, 2.5 mmol) at 0° C. The reaction mixture was warmed to room temperature and stirred for 1 h. To a solution of [17(20)E]-propylideneestra-1,3,5(10)-trien-3-ol (27, 0.148 g, 0.5 mmol) in DMF (3.0 mL) was added sodium hydride (0.100 g of a mineral oil dispersion, 60%, 2.5 mmol) at 0° C. The reaction mixture was stirred for 1 h, and the chlorosulfonyl isocyanate in formic acid was added, and stirring continued for 1 h. The reaction mixture was quenched with saturated aqueous NH$_4$Cl at 0° C., and extracted with EtOAc. The combined organic layers were washed with H$_2$O, saturated aqueous NaCl, and then dried (Na$_2$SO$_4$). The desiccant was filtered and the solvent was evaporated at reduced pressure. The residue was purified by column chromatography (silica gel) using n-hexane:EtOAc (5:1→3:1, v/v) to afford 0.177 g of 28 (94% yield) mp: 149–151° C.

$^1$H NMR: δ 7.33 (d, 1H, aromatic), 7.13–7.00 (m, 2H, aromatic), 5.08–4.95 (m, 1H, =C$\underline{H}$—CH$_2$—), 4.89 (s, 2H, —NH$_2$), 0.96 (t, 3H, 23-CH$_3$), 0.79 (s, 3H, 18-CH$_3$); MS (EI): m/z 375 (M$^+$).

The following scheme illustrates the synthetic steps carried out in Examples 11 and 12 to make the anti-estrogenic compounds (32) and (34):

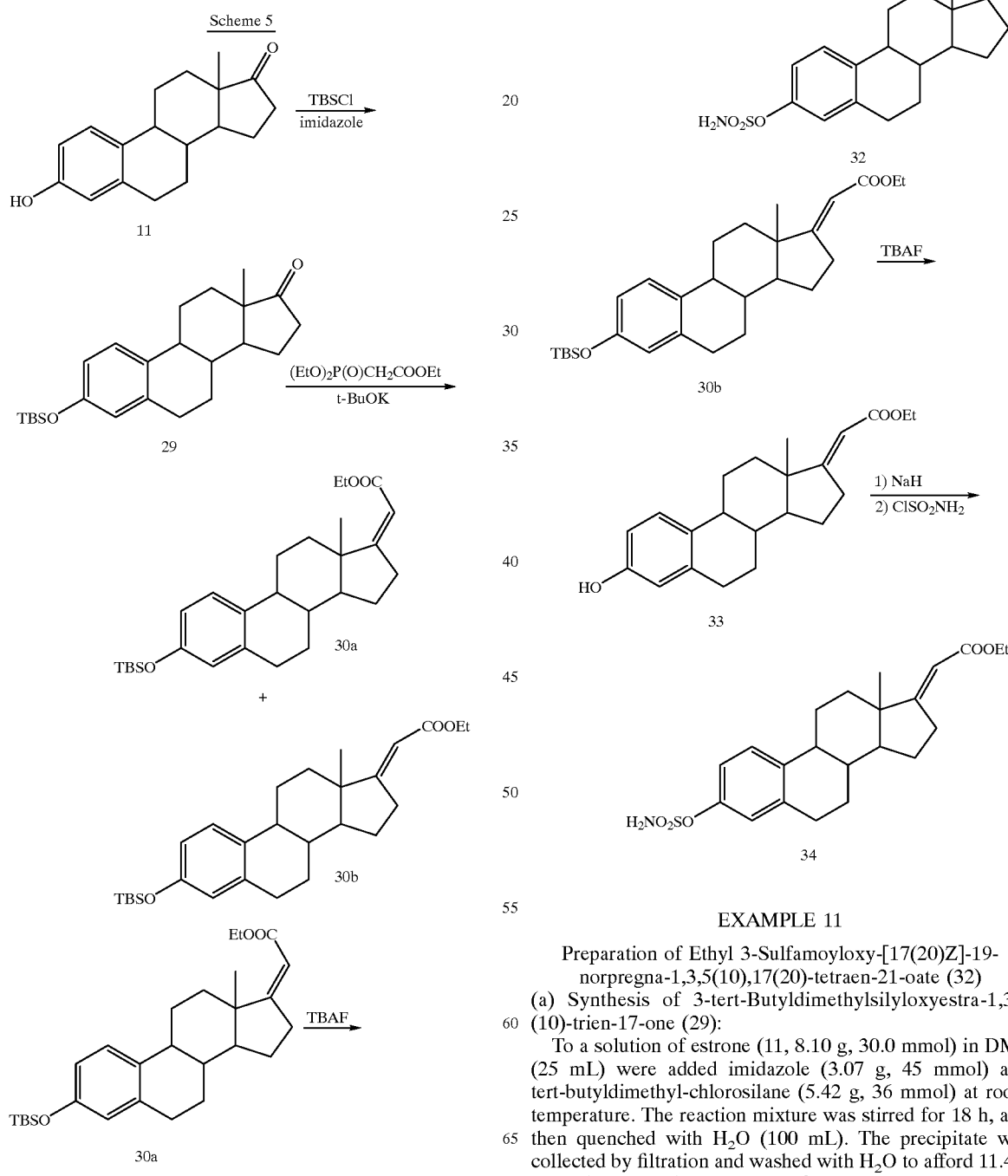

EXAMPLE 11

Preparation of Ethyl 3-Sulfamoyloxy-[17(20)Z]-19-norpregna-1,3,5(10),17(20)-tetraen-21-oate (32)

(a) Synthesis of 3-tert-Butyldimethylsilyloxyestra-1,3,5 (10)-trien-17-one (29):

To a solution of estrone (11, 8.10 g, 30.0 mmol) in DMF (25 mL) were added imidazole (3.07 g, 45 mmol) and tert-butyldimethyl-chlorosilane (5.42 g, 36 mmol) at room temperature. The reaction mixture was stirred for 18 h, and then quenched with H$_2$O (100 mL). The precipitate was collected by filtration and washed with H$_2$O to afford 11.4 g of 29 (99% yield) mp: 171–172° C.

¹H NMR: δ 7.12 (d, 1H, aromatic), 6.67–6.55 (m, 2H, aromatic), 0.98 (s, 9H, —C(CH₃)₃), 0.91 (s, 3H, 18-CH₃), 0.19 (s, 6H, —Si(CH₃)₂).

(b) Synthesis of Ethyl-3-tert-Butyldimethylsilyloxy-[17(20)Z]-19-norpregna-1,3,5(10),17(20)-tetraen-21-oate (30a) and Ethyl 3-tert-Butyldimethylsilyloxy-[17(20)E]-19-norpregna-1,3,5(10),17(20)-tetraen-21-oate (30b):

To a solution of triethylphosphonoacetate (3.17 mL, 16 mmol) in THF (40 mL) was added potassium tert-butoxide (1.68 g, 15 mmol) at room temperature. The reaction mixture was stirred for 30 min, and 3-tert-butyldimethylsilyloxyestra-1,3,5(10)-trien-17-one (29, 1.92 g, 5.0 mmol) was added. The stirring continued for 2 days at reflux condition. After the reaction mixture was cooled to room temperature, saturated aqueous NH₄Cl was added and the mixture extracted with EtOAc. The combined organic layers were washed with H₂O, saturated aqueous NaCl, and then dried (Na₂SO₄). The desiccant was filtered and the solvent was evaporated at reduced pressure. The residue was purified by column chromatography (silica gel) using n-hexane:EtOAc (40:1→30:1, v/v) to afford 0.473 g of 30a (21% yield) mp: 148–149° C., and 1.26 g of 30b (55% yield) mp: 109–110° C.

¹H NMR (30a): δ 7.12 (d, 1H, aromatic), 6.65–6.50 (m, 2H, aromatic), 5.70–5.63 (m, 1H, =CH—COOEt—), 4.23–4.05 (m, 2H, —COOCH₂CH₃), 1.29 (t, 3H, —COOCH₂CH₃), 1.04 (s, 3H, 18-CH₃), 0.98 (s, 9H, —C(CH₃)₃), 0.18 (s, 6H, —Si(CH₃)₂).

¹H NMR (30b): δ 7.12 (d, 1H, aromatic), 6.65–6.50 (m, 2H, aromatic), 5.59 (s, 1H, =CH—COOEt—), 4.16 (q, 2H, —COOCH₂CH₃), 1.29 (t, 3H, —COOCH₂CH₃), 0.98 (s, 9H, —C(CH₃)₃), 0.86 (s, 3H, 18-CH₃), 0.19 (s, 6H, Si(CH₃)₂).

(c) Synthesis of Ethyl 3-Hydroxy-[17(20)Z]-19-norpregna-1,3,5(10), 17(20)-tetraen-21-oate (31):

To a solution of ethyl 3-tert-butyldimethylsilyloxy-[17(20)Z]-19-norpregna-1,3,5(10),17(20)-tetraen-21-oate (30a, 0.387 g, 0.85 mmol) in THF (10 mL) was added tetrabutylammonium fluoride (0.90 mL of a THF solution, 1.0 M, 0.90 mmol) at 0° C. The reaction mixture was stirred for 1 h, diluted with EtOAc, washed with H₂O, saturated aqueous NaCl, and then dried (Na₂SO₄). The desiccant was filtered and the solvent was evaporated at reduced pressure. The residue was purified by column chromatography (silica gel) using n-hexane:EtOAc (7:1→5:1, v/v) to afford 0.279 g of 31 (97% yield) mp: 144–145° C.

1H NMR: δ 7.15 (d, 1H, aromatic), 6.67–6.52 (m, 2H, aromatic), 5.72–5.66 (m, 1H, =CH—COOEt), 4.23–4.08 (m, 2H, —COOCH₂CH₃), 1.29 (t, 3H, —COOCH₂CH₃), 1.04 (s, 3H, 18-CH₃); MS (EI): m/z 340 (M⁺).

(d) Synthesis of Ethyl 3-Sulfamoyloxy-[17(20)Z]-19-norpregna-1,3,5(10),17(20)-tetraen-21-oate (32):

To a solution of chlorosulfonyl isocyanate (0.22 mL, 2.5 mmol) in CH₂Cl₂ (1.0 mL) was added formic acid (0.5 mL of a CH₂Cl₂ solution, 5.0 M, 2.5 mmol) at 0° C. The reaction mixture was warmed to room temperature and stirred for 1 h. To a solution of ethyl 3-hydroxy-[17(20)Z]-19-norpregna-1,3,5(10),17(20)-tetraen-21-oate (31, 0.170 g, 0.5 mmol) in DMF (3.0 mL) and THF (1.0 mL) was added sodium hydride (0.100 g of a mineral oil dispersion, 60%, 2.5 mmol) at 0° C. The reaction mixture was stirred for 1 h, and the chlorosulfonyl isocyanate in formic acid was added, and stirring continued for 2 h. The reaction mixture was quenched with saturated aqueous NH₄Cl at 0° C., and extracted with EtOAc. The combined organic layers were washed with H₂O, saturated aqueous NaCl, and then dried (Na₂SO₄). The desiccant was filtered and the solvent was evaporated at reduced pressure. The residue was purified by column chromatography (silica gel) using n-hexane:EtOAc (3:1→2:1, v/v) to afford 0.174 g of 32 (83% yield) mp: 154–155° C. ¹H NMR: δ 7.31 (d, 1H, aromatic), 7.15–7.00 (m, 2H, aromatic), 5.69 (s, 1H, =CH—COOEt), 4.93 (s, 1H, —NH₂), 4.15 (q, 2H, —COOCH₂CH₃), 1.29 (t, 3H,—COOCH₂CH₃), 1.04 (s, 3H, 18-CH₃); MS (EI): m/z 419 (M⁺).

EXAMPLE 12

Preparation of Ethyl 3-Sulfamoyloxy-[17(20)E]-19-norpregna-1,3,5(10),20-tetraen-21-oate (34)

(a) Synthesis of Ethyl 3-tert-Butyldimethyl-silyloxy-[17(20)E]-19-norpregna-1,3,5(10),17(20)-tetraen-21-oate (30b):

The procedure described in steps (a) and (b) of Example 11 above was used to obtain 30b from 11.

(b) Synthesis of Ethyl 3-Hydroxy-[17(20)E]-19-norpregna-1,3,5(10),17(20)-tetraen-21-oate (33):

By using the procedure described in step (c) of Example 11 above, beginning with ethyl 3-tert-butyldimethylsilyloxy-[17(20)E]-19-norpregna-1,3,5(10), 17(20)-tetraen-21-oate (30b, 1.00 g, 2.2 mmol), there was obtained 0.727 g of 33 (97% yield;

mp: 153–154° C.) after chromatography (n-hexane:EtOAc 5:1→3:1, v/v).

¹H NMR: δ 7.15 (d, 1H, aromatic), 6.68–6.53 (m, 2H, aromatic), 5.59 (s, 1H, =CH—COOEt—), 4.77–4.65 (m, 1H, —OH), 4.17 (q, 2H, —COOCH₂CH₃), 1.29 (t, 3H, —COOCH₂CH₃), 0.86 (s, 3H, 18-CH₃); MS (EI): m/z 340 (M⁺).

(c) Synthesis of Ethyl 3-Sulfamoyloxy-[17(20)E]-19-norpregna-1,3,5(10),17(20)-tetraen-21-oate (34):

By the procedure described in step (d) of Example 11 above, there was obtained from ethyl 3-hydroxy-[17(20)E]-19-norpregna-1,3,5(10),17(20)-tetraen-21-oate (33, 0.102 g, 0.3 mmol) after chromatography (n-hexane:EtOAc 5:1→3:1, v/v), 0.097 g of 34 (77% yield) mp: 174–175° C.

¹H NMR: δ 7.32 (d, 1H, aromatic), 7.13–7.00 (m, 2H, aromatic), 5.62–5.57 (m, 1H, =CH—COOEt), 4.89 (s, 1H, —NH₂), 4.16 (q, 2H, —COOCH₂CH₃), 1.29 (t, 3H, —COOCH₂CH₃), 0.87 (s, 3H, 18-CH₃); MS (EI): m/z 419 (M⁺).

EXAMPLE 13

Preparation of 20-Cyano-19-Norpregna-1,3,5(10),17(20)-tetraene-21-nitrile-3-O-sulfamate (36)

Scheme 6

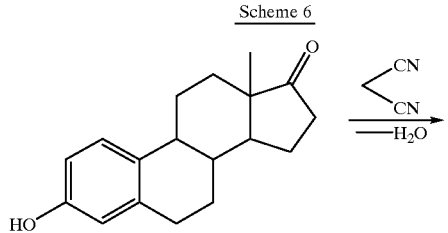

11

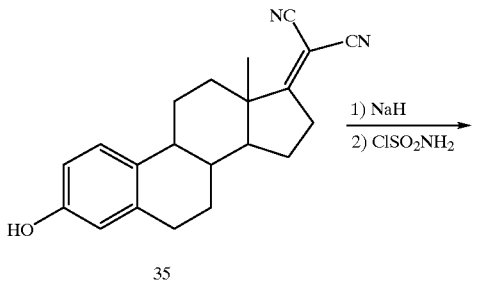

(a) Synthesis of 20-Cyano-3-hydroxy-19-norpregna-1,3,5(10),17(20)-tetraene-21-nitrile (35):

To a suspension of estrone (11, 1.35 g, 5.0 mmol) in benzene (35 mL) and acetic acid (5.0 mL) were added malononitrile (1.65 g, 40 nunol) and β-alanine (0.535 g, 6.0 mmol), and stirred for 19 h at reflux condition. After the reaction mixture was cooled to room temperature, $H_2O$ was added and extracted with EtOAc. The combined organic layers were washed with $H_2O$, saturated aqueous NaCl, and then dried ($Na_2SO_4$). The desiccant was filtered and the solvent was evaporated at reduced pressure. The residue was washed with $Et_2O$ to afford 1.46 g of 35 (92% yield) mp: >250° C.

$^1$H NMR: δ 7.13 (d, 1H, aromatic), 6.70–6.53 (m, 2H, aromatic), 1.07 (s, 3H, 18-$CH_3$); MS (EI): m/z 318 ($M^+$).

(b) Synthesis of 20-Cyano-19-norpregna-1,3,5(10),17(20)-tetraene-21-nitrile-3-O-sulfamate (36):

To a solution of chlorosulfonyl isocyanate (0.22 mL, 2.5 mmol) in $CH_2Cl_2$ (1.0 mL) was added formic acid (0.5 mL of a $CH_2Cl_2$ solution, 5.0 M, 2.5 mmol) at 0° C. The reaction mixture was warmed to room temperature and stirred for 1 h. To a solution of 20-cyano-3-hydroxy-19-norpregna-1,3,5(10),17(20)-tetraene-21-nitrile (35, 0.159 g, 0.5 mmol) in DMF (3.0 mL) was added sodium hydride (0.100 g of a mineral oil dispersion, 60%, 2.5 mmol) at 0° C. The reaction mixture was stirred for 1 h, and the chlorosulfonyl isocyanate in formic acid was added, and stirring continued for 1 h. The reaction mixture was quenched with saturated aqueous $NH_4Cl$ at 0° C., and extracted with EtOAc. The combined organic layers were washed with $H_2O$, saturated aqueous NaCl, and then dried ($Na_2SO_4$). The desiccant was filtered and the solvent was evaporated at reduced pressure. The residue was purified by column chromatography (silica gel) using n-hexane:acetone (3:1→3:2, v/v) to afford 0.152 g of 36 (77% yield) mp: 183–184° C.

$^1$H NMR: δ 7.31 (d, 1H, aromatic), 7.20–7.00 (m, 2H, aromatic), 4.93 (s, 1H, —$NH_2$), 1.08 (s, 3H, 18-$CH_3$); MS (EI): m/z 397 ($M^+$).

EXAMPLE 14

Preparation of 21-(2'-N,N-Dimethylaminoethoxy)-[17(20)E]-19-norpregna-1,3,5(10),18(20)-tetraene-3-O-sulfamate (39)

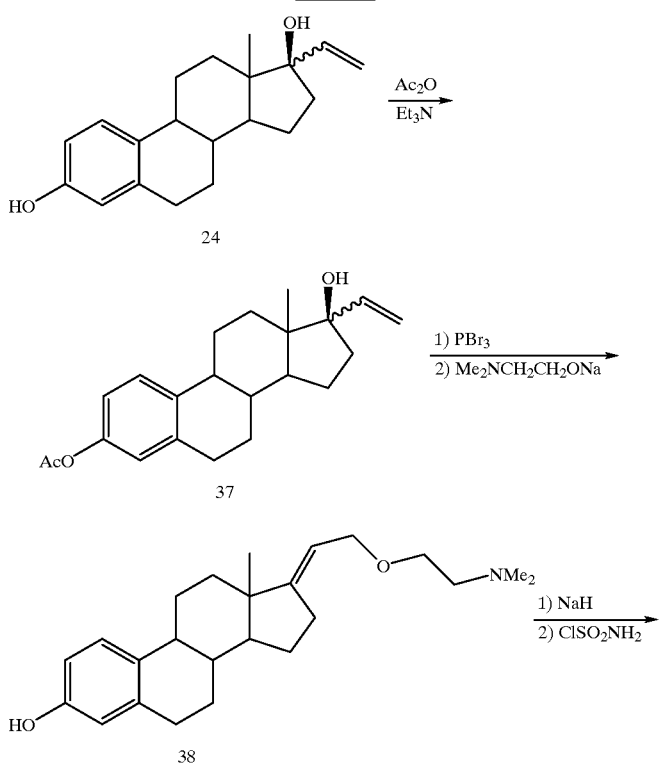

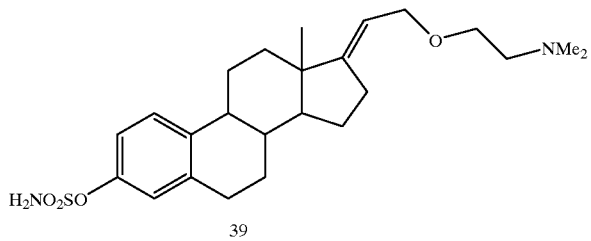

39

(a) Synthesis of 17α-Ethenylestra-1,3,5(10)-trien-3,17β-diol 3-O-acetate (37):

To a solution of 17α-ethenylestradiol (24, 0.895 g, 3.0 mmol) in CH$_2$Cl$_2$ (7.0 mL) and THF (3.0 mL) were added triethylamine (0.95 mL, 6.7 mmol) and acetic anhydride (0.4 mL, 4.0 mmol) at room temperature. The reaction mixture was stirred for 20 h, diluted with EtOAc, washed with H$_2$O, saturated aqueous NaCl, and then dried (Na$_2$SO$_4$). The desiccant was filtered and the solvent was evaporated at reduced pressure. The residue was purified by column chromatography (silica gel) using n-hexane:EtOAc (3:1→2:1, v/v) to afford 1.02 g of 37 (100% yield) mp: 127–128° C.

$^1$H NMR: δ 7.26 (d, 1H, aromatic), 6.88–6.77 (m, 2H, aromatic), 6.10 (dd, 1H, —C<u>H</u>═CH$_2$), 5.25–5.10 (m, 2H, —CH═C<u>H</u>$_2$), 2.27 (s, 3H, —OCOCH$_3$), 0.94 (s, 3H, 18-CH$_3$).

(b) Synthesis of 21-(2'-N,N-Dimethylaminoethoxy)-[17(20) E]-19-norpregna-1,3,5(10),17(20)-tetraen-3-ol (38):

To a solution of phosphorous tribromide (3.2 mL of a CH$_2$Cl$_2$ solution, 1.0 M, 3.2 mmol) in toluene (4.0 mL) was added a solution of 17α-ethenylestra-1,3,5(10)-trien-3,17β-diol 3-O-acetate (37, 1.09 g, 3.2 mmol) and pyridine (0.3 mL, 3.7 mmol) in toluene (20 mL) at 0° C. The reaction mixture was stirred for 2 h, and quenched with saturated aqueous NH$_4$Cl at 0° C. and extracted with EtOAc. The combined organic layers were washed with H$_2$O, saturated aqueous NaCl, and then dried (Na$_2$SO$_4$). The desiccant was filtered and the solvent was evaporated at reduced pressure. The residue was dissolved in THF (20 mL) and added to a mixture of N,N-dimethylethanolamine (3.0 mL, 30 mmol) and sodium hydride (1.00 g of a mineral oil dispersion, 60%, 25 mmol) in THF (20 mL) at 0° C. The reaction mixture was stirred for 2 h, and quenched with saturated aqueous NaHCO$_3$ at 0° C. and extracted with EtOAc. The combined organic layers were washed with H$_2$O, saturated aqueous NaCl, and then dried (Na$_2$SO$_4$). The desiccant was filtered and the solvent was evaporated at reduced pressure. The residue was purified by column chromatography (silica gel) using CHCl$_3$:MeOH (10:1→7:1, v/v) to afford 0.309 g of 38 (26% yield) mp: 116–117° C.

$^1$H NMR: δ 7.12 (d, 1H, aromatic), 6.63–6.48 (m, 2H, aromatic), 5.25–5.14 (m, 1H, ═C<u>H</u>—CH$_2$O—), 3.98 (d, 2H, ═CH—C<u>H</u>$_2$O—), 3.65–3.45 (m, 2H, —OC<u>H</u>$_2$CH$_2$N—) 2.61 (t, 2H, —OCH$_2$C<u>H</u>$_2$N—), 2.34 (s, 6H, —N(CH$_3$)2), 0.76 (s, 3H, 18-CH$_3$); MS (DCI): m/z 370 (M$^+$H).

(c) Synthesis of 21-(2'-N,N-Dimethylaminoethoxy)-[17(20) E]-19-norpregna-1,3,5(10),17(20)-tetraene-3-O-sulfamate (39):

To a solution of chlorosulfonyl isocyanate (0.14 mL, 1.5 mmol) in CH$_2$Cl$_2$ (0.6 mL) was added formic acid (0.3 mL of a CH$_2$Cl$_2$ solution, 5.0 M, 1.5 mmol) at 0° C. The reaction mixture was warmed to room temperature and stirred for 1 h. To a solution of 21-(2'-N,N-dimethylaminoethoxy)-[17 (20)E]-19-norpregna-1,3,5(10),17(20)-tetraen-3-ol (38, 0.111 g, 0.3 mmol) in DMF (2.0 mL) was added sodium hydride (0.060 g of a mineral oil dispersion, 60%, 1.5 mmol) at 0° C. The reaction mixture was stirred for 1 h, and the chlorosulfonyl isocyanate in formic acid was added, and stirring continued for 2 h. The reaction mixture was quenched with saturated aqueous NaHCO$_3$ at 0° C., and extracted with EtOAc. The combined organic layers were washed with H$_2$O, saturated aqueous NaCl, and then dried (Na$_2$SO$_4$). The desiccant was filtered and the solvent was evaporated at reduced pressure. The residue was purified by column chromatography (silica gel) using CHCl$_3$:MeOH (10:1→5:1, v/v) to afford 0.121 g of 39 (90% yield) mp: 147–148° C.

$^1$H NMR: δ 7.30 (d, 1H, aromatic), 7.13–7.00 (m, 2H, aromatic), 5.30–5.18 (m, 1H, ═C<u>H</u>—CH$_2$O—), 4.05–3.90 (m, 2H, ═CH—C<u>H</u>$_2$O—), 3.53 (t, 2H, —OC<u>H</u>$_2$CH$_2$N—) 2.55 (t, 2H, —OCH$_2$C<u>H</u>$_2$N—), 2.30 (s, 6H, —N(CH$_3$)$_2$), 0.78 (s, 3H, 18-CH$_3$); MS (DCI): m/z 449 (M$^+$+H).

The following scheme illustrates the synthetic steps carried out in Examples 15 and 16 to make the estrone sulfatase inhibitory compounds (44) and (47):

Scheme 8

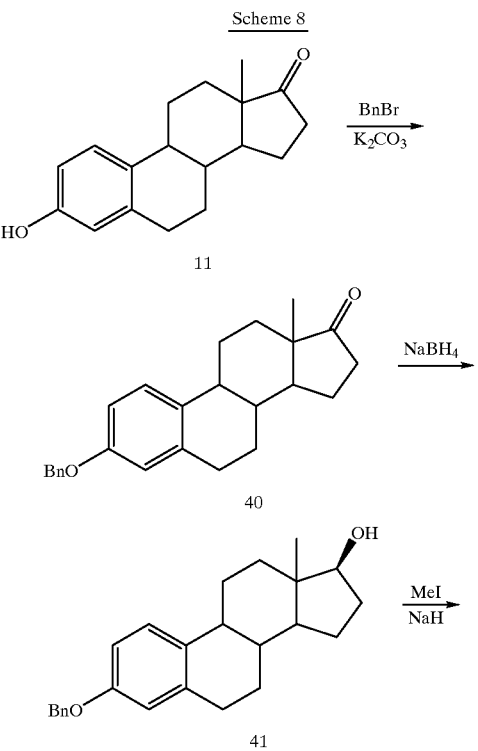

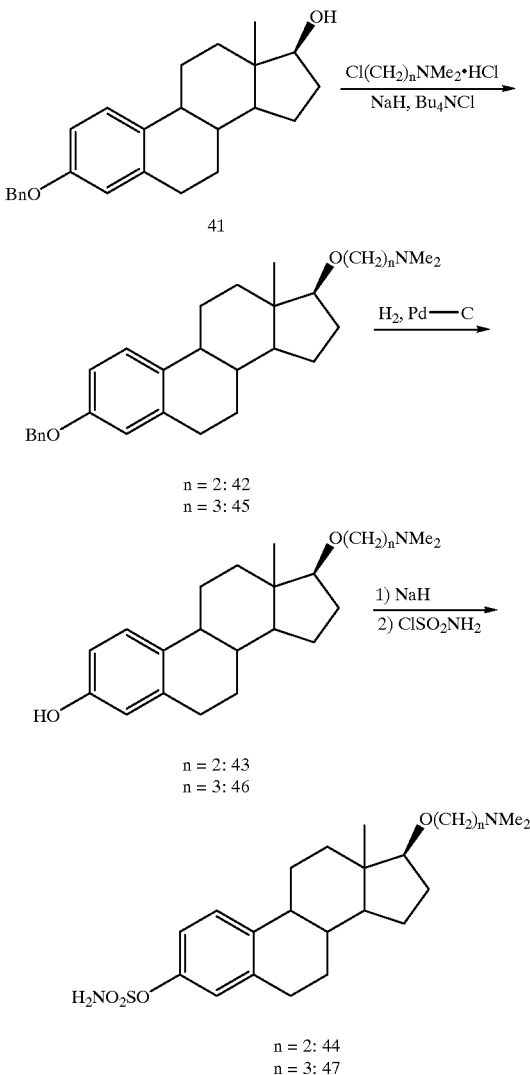

n = 2: 42
n = 3: 45 n = 2: 43
n = 3: 46 n = 2: 44
n = 3: 47

EXAMPLE 15

Preparation of 17β-(2'-N,N-Dimethylaminoethoxy)estra-1,3,5(10)-triene-3-O-sulfamate (44)

(a) Synthesis of 3-Benzyloxyestra-1,3,5(10)-trien-17-one (40):

To a solution of estrone (11, 2.70 g, 10 mmol) in DMF (40 mL) were added potassium carbonate (2.76 g, 20 mmol) and benzyl bromide (1.8 mL, 15 mmol) at room temperature. The reaction mixture was stirred for 26 h, then quenched with H₂O, and extracted with EtOAc. The combined organic layers were washed with H₂O, saturated aqueous NaCl, and then dried (Na₂SO₄). The desiccant was filtered and the solvent was evaporated at reduced pressure. The residue was washed with Et₂O to afford 2.91 g of 40 (81% yield) mp: 126–127° C.

$^1$H NMR: δ 7.65–7.10 (m, 6H, aromatic), 6.90–6.65 (m, 2H, aromatic), 5.04 (s, 2H, —OCH₂Ph), 0.91 (s, 3H, 18-CH₃); MS (EI): m/z 360 (M⁺).

(b) Synthesis of 3-Benzyloxyestra-1,3,5(10)-trien-17β-ol (41):

To a solution of 3-benzyloxyestra-1,3,5(10)-trien-17-one (40, 2.70 g, 7.5 mmol) in THF (5.0 mL) and MeOH (30 mL) was added sodium borohydride (284 mg, 7.5 mmol) at 0° C.

The reaction mixture was stirred for 30 min, then quenched with saturated aqueous NH₄Cl, and H₂O added. The precipitate was collected by filtration and washed with H₂O to afford 2.73 g of 41 (100% yield) mp: 118–119° C.

$^1$H NMR: δ 7.50–7.15 (m, 6H, aromatic), 6.83–6.67 (m, 2H, aromatic), 5.03 (s, 2H, —OCH₂Ph), 3.80–3.65 (m, 2H, 17α-H, —OH), 0.78 (s, 3H, 18-CH₃); MS (EI): m/z 362 (M⁺).

(c) Synthesis of 3-Benzyloxy-17β-ol (2'-N,N-dimethyl-aminoethoxy)estra-1,3,5(10)-triene (42):

To a solution of 3-benzyloxyestra-1,3,5(10)-trien-17β-ol (41, 1.81 g, 5.0 mmol) in DMF (40 mL) was added sodium hydride (3.00 g of a mineral oil dispersion, 60%, 75 mmol) at 0° C., and stirred for 30 min, then added 2-N,N-dimethylaminoethylchloride hydrochloride (2.16 g, 15 mmol) and tetrabutylammonium iodide (0.185 g, 0.50 mmol) and stirred for 3 h at 100° C. After the reaction mixture was cooled to room temperature, saturated aqueous NaHCO₃ was added and the mixture extracted with EtOAc. The combined organic layers were washed with H₂O, saturated aqueous NaCl, and then dried (Na₂SO₄). The desiccant was filtered and the solvent was evaporated at reduced pressure. The residue was purified by column chromatography (silica gel) using CHCl₃:MeOH (30:1→10:1, v/v) to afford 1.82 g of 42 (84% yield) mp: 153–155° C.

$^1$H NMR: δ 7.50–7.15 (m, 6H, aromatic), 6.85–6.67 (m, 2H, aromatic), 5.03 (s, 2H, —OCH₂Ph), 4.03–3.85 (m, 2H, 17β-OCH₂-), 3.44 (t, 1H, 17α-H), 2.89 (s, 6H, —N(CH₃)₂), 0.77 (s, 3H, 18-CH₃).

(d) Synthesis of 17β-(2'-N,N-Dimethylamino-ethoxy)estra-1,3,5(10)-trien-3-ol (43):

To a solution of 3-benzyloxy-17β-(2'-N,N-dimethylaminoethoxy) estra-1,3,5(10)-triene (42, 1.73 g, 4.0 mmol) in MeOH (20 mL) was added 10% palladium on carbon (0.500 g). The reaction mixture was stirred for 2 h under a hydrogen atmosphere at room temperature. After the catalyst was filtered, the solvent was evaporated at reduced pressure. The residue was purified by column chromatography (silica gel) using CHCl₃:MeOH (10:1→3:1, v/v) to afford 1.27 g of 43 (92% yield) mp: 191–192° C.

$^1$H NMR: δ 7.13 (d, 1H, aromatic), 6.68–6.48 (m, 2H, aromatic), 3.73–3.48 (m, 2H, 17β-OCH₂—), 3.37 (t, 1H, 17α-H), 2.33 (s, 6H, —N(CH₃)₂), 0.74 (s, 3H, 18-CH₃); MS (DCI): m/z 344 (M⁺+H).

(e) Synthesis of 17β-(2'-N,N-Dimethylaminoethoxy)estra-1,3,5(10)-triene-3-O-sulfamate (44):

To a solution of chlorosulfonyl isocyanate (0.22 mL, 2.5 mmol) in CH₂Cl₂ (1.0 mL) was added formic acid (0.5 mL of a CH₂Cl₂ solution, 5.0 M, 2.5 mmol) at 0° C. The reaction mixture was warmed to room temperature and stirred for 1 h. To a solution of 17β-(2'-N,N-dimethylaminoethoxy)estra-1,3,5(10)-trien-3-ol (43, 0.172 g, 0.5 mmol) in DMF (3.0 mL) and THF (1.0 mL) was added sodium hydride (0.100 g of a mineral oil dispersion, 60%, 2.5 mmol) at 0° C. The reaction mixture was stirred for 1 h, and the chlorosulfonyl isocyanate in formic acid was added, and stirring continued for 2 h. The reaction mixture was quenched with saturated aqueous NaHCO₃ at 0° C., and extracted with EtOAc. The combined organic layers were washed with H₂O, saturated aqueous NaCl, and then dried (Na₂SO₄). The desiccant was filtered and the solvent was evaporated at reduced pressure. The residue was purified by column chromatography (silica gel) using CHCl₃:MeOH (10:1→5:1, v/v) to afford 0.180 g of 44 (85% yield) mp: 142–143° C.

$^1$H NMR: δ 7.28 (d, 1H, aromatic), 7.13–7.00 (m, 2H, aromatic), 3.90–3.45 (m, 4H, 17β-OCH₂—, —NH₂), 3.37 (t, 1H, 17α-H), 2.34 (s, 6H, —N(CH₃)₂), 0.73 (s, 3H, 18-CH₃); MS (DCI): m/z 423 (M⁺+H).

EXAMPLE 16

Preparation of 17β-(3'-N,N-Dimethylaminopropoxy)estra-1,3,5(10)-triene-3-O-sulfamate (47)

(a) Synthesis of 3-Benzyloxyestra-1,3,5(10)-trien-17β-ol (41):

The procedure described in steps (a) and (b) of Example 15 above was used to obtain 41.

(b) Synthesis of 3-Benzyloxy-17(3-N,N-dimethylaminopropoxy)estra-1,3,5(10)-triene (45):

To a solution of 3-benzyloxyestra-1,3,5(10)-trien-17β-ol (41, 1.27 g, 3.5 mmol) in DMF (30 mL) were added sodium hydride (2.10 g of a mineral oil dispersion, 60%, 52.5 mmol) at 0° C., and stirred for 30 min. Next was added 3-N,N-dimethylaminopropylchloride hydrochloride (1.66 g, 10.5 mmol) and tetrabutylammonium iodide (0.129 g, 0.35 mmol) and stirred for 19 h at 100° C. After the reaction mixture was cooled to room temperature, saturated aqueous NaHCO$_3$ was added and the mixture extracted with EtOAc. The combined organic layers were washed with H$_2$O, saturated aqueous NaCl, and then dried (Na$_2$SO$_4$). The desiccant was filtered and the solvent was evaporated at reduced pressure. The residue was purified by column chromatography (silica gel) using CHCl$_3$:MeOH (20:1→10:1, v/v) to afford 1.57 g of 45 (100% yield) mp: 190–192° C.

$^1$H NMR: δ 7.50–7.15 (m, 6H, aromatic), 6.83–6.67 (m, 2H, aromatic), 5.03 (s, 2H, —OCH$_2$Ph), 3.60–3.43 (m, 2H, 17β-OCH$_2$—), 3.37 (t, 1H, 17α-H), 2.28 (s, 6H, —N(CH$_3$)$_2$), 0.78 (s, 3H, 18-CH$_3$).

(c) Synthesis of 17β-(3'-N,N-Dimethylaminopropoxy)estra-1,3,5(10)-trien-3-ol (46):

By the procedure described in step (d) of Example 15 above, there was obtained from 3-benzyloxy-17β-(3'-N,N-dimethylaminopropoxy)estra-1,3,5(10)-triene (45, 1.57 g, 3.50 mmol) after washing with Et$_2$O, 0.992 g of 46 (79% yield) mp: >250° C.

$^1$H NMR (CDCl$_3$-DMSO-d$_6$): δ 8.20 (s, 1H, —OH), 6.91 (d, 1H, aromatic), 6.50–6.33 (m, 2H, aromatic), 3.47–3.30 (m, 2H, 17β-OCH$_2$—), 3.18 (t, 1H, 17α-H), 2.64, 2.63 (s and s, each 3H, —N(CH$_3$)$_2$), 0.55 (s, 3H, 18—CH$_3$); MS (DCI): m/z 358 (M$^+$+H).

(d) Synthesis of 17β—(3'-N,N-Dimethylaminopropoxy)estra-1,3,5(10)-triene-3-O-sulfamate (47):

By the procedure described in step (e) of Example 15 above, there was obtained from 17β-(3'-N,N-dimethylaminopropoxy)estra-1,3,5(10)-trien-3-ol (46, 0.179 g, 0.50 mmol) after chromatography (CHCl$_3$:MeOH 10:1→5:1, v/v), 0.161 g of 47 (74% yield) mp: 122–123° C.

$^1$H NMR (CDCl$_3$-DMSO-d$_6$): d 7.28 (d, 1H, aromatic), 7.11–7.00 (m, 2H, aromatic), 3.62–3.45 (m, 2H, 17β-OCH$_2$—), 3.38 (t, 1H, 17α-H), 2.41 (s, 6H, —N(CH$_3$)$_2$), 0.77 (s, 3H, 18-CH$_3$); MS (DCI): m/z 437 (M$^+$+H).

The following scheme illustrates the synthetic steps carried out in Examples 17 and 18 to make the estrone sulfatase inhibitory compounds (52) and (55):

Scheme 9

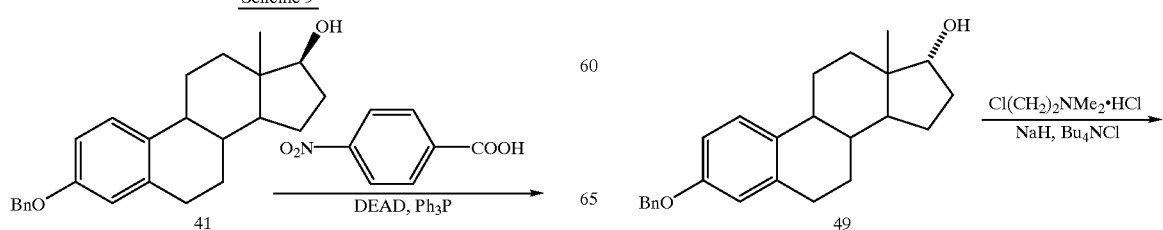

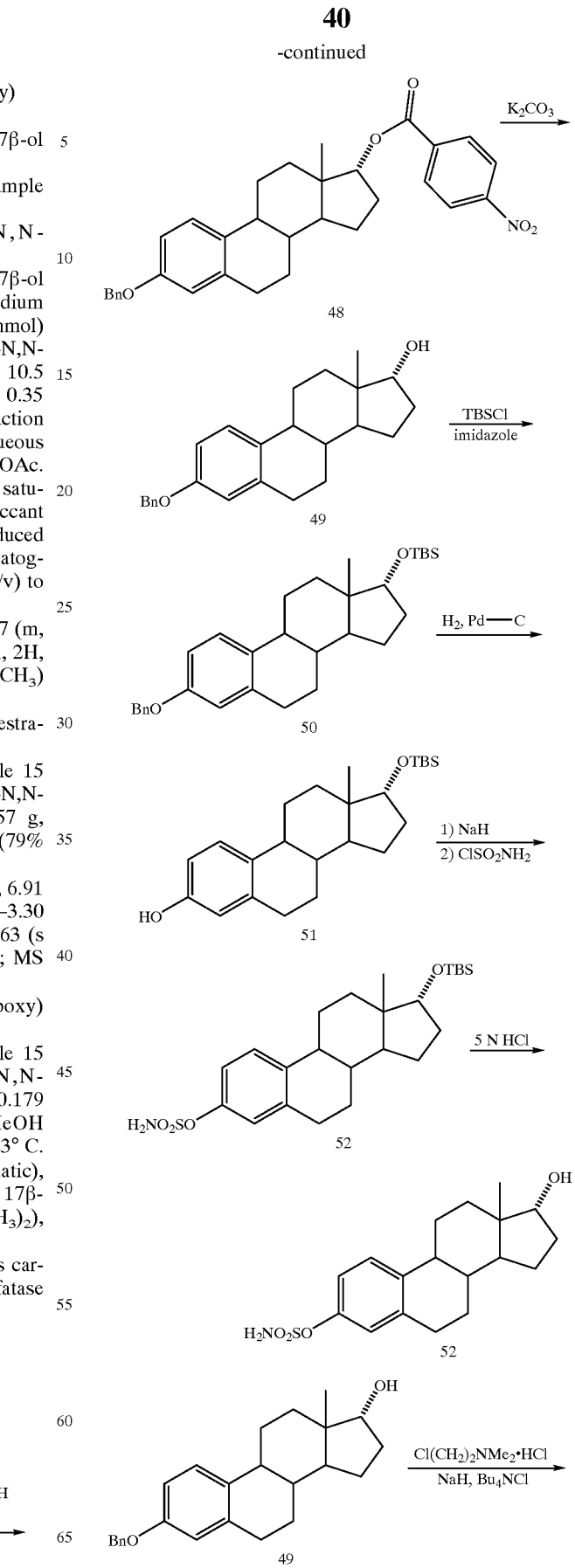

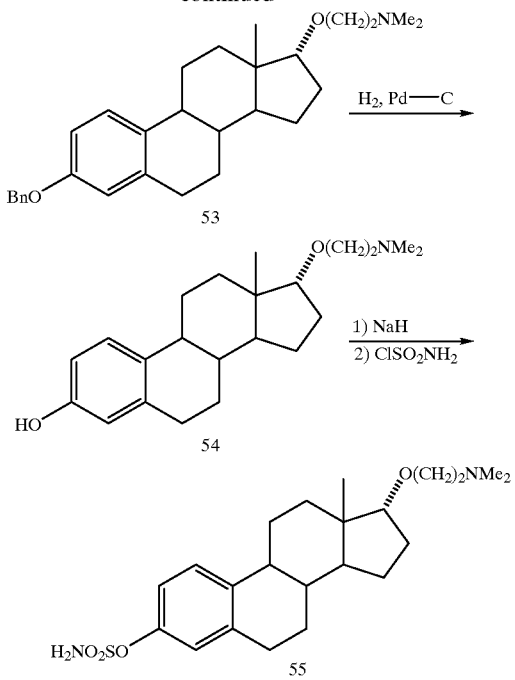

EXAMPLE 17

Preparation of 17α-tert-Butyldimethylsilyloxyestra-1,3,5(10)-triene-3-O-sulfamate (52)

(a) Synthesis of 3-Benzyloxyestra-1,3,5(10)-trien-17β-ol (41):

The procedure described in steps (a) and (b) of Example 15 above was used to obtain 41 from 11.

(b) Synthesis of 3-Benzyloxyestra-1,3,5(10)-trien-17α-ol 17α-O-p-nitrobenzoate (48):

To a suspension of triphenylphosphine (6.29 g, 24 mmol) and diethyl azodicarboxylate (4.18 g 24 mmol) in toluene (40 mL) was added a solution of 3-benzyloxyestra-1,3,5 (10)-trien-17β-ol (41, 4.35 g, 12.0 mmol) in toluene (40 mL) at room temperature, and stirred for 2 h at 80° C. After the reaction mixture was cooled to room temperature, $H_2O$ was added and the mixture extracted with EtOAc. The combined organic layers were washed with $H_2O$, saturated aqueous NaCl, and then dried ($Na_2SO_4$). The desiccant was filtered and the solvent was evaporated at reduced pressure. The residue was purified by column chromatography (silica gel) using n-hexane:EtOAc (10:1→7:1, v/v) to afford 5.82 g of 48 (95% yield) mp: 135–136° C.

$^1$H NMR: δ 8.37–8.18 (m, 4H, aromatic), 7.52–7.30 (m, 5H, aromatic), 7.19 (d, 1H, aromatic), 6.85–6.68 (m, 2H, aromatic), 5.15 (d, 1H, 17β-H), 5.03 (s, 2H, —OCH$_2$Ph), 0.88 (s, 3H, 18-CH$_3$).

(c) Synthesis of 3-Benzyloxyestra-1,3,5(10)-trien-17α-ol (49):

To a solution of 3-benzyloxyestra-1,3,5(10)-trien-17α-ol 17α-O-p-nitrobenzoate (48, 6.14 g, 12 mmol) in THF (40 mL) and MeOH (40 mL) was added potassium carbonate (1.66 g, 12 mmol) and stirred for 2 h at room temperature. The reaction mixture was quenched with $H_2O$, and extracted with EtOAc. The combined organic layers were washed with $H_2O$, saturated aqueous NaCl, and then dried ($Na_2SO_4$). The desiccant was filtered and the solvent was evaporated at reduced pressure. The residue was purified by column chromatography (silica gel) using n-hexane:EtOAc (5:1→3:1, v/v) to afford 4.10 g of 49 (94% yield) mp: 85–86° C.

$^1$H NMR: δ 7.55–7.30 (m, 5H, aromatic), 7.22 (d, 1H, aromatic), 6.85–6.67 (m, 2H, aromatic), 5.03 (s, 2H, —OCH$_2$Ph), 3.81 (d, 1H, 17β-H), 0.70 (s, 3H, 18-CH$_3$).

(d) Synthesis of 3-Benzyloxy-17α-tert-butyldimethylsilyloxyestra-1,3,5(10)-triene (50):

To a solution of 3-benzyloxyestra-1,3,5(10)-trien-17α-ol (49, 1.45 g, 4.0 mmol) in DMF (5.0 mL) were added imidazole (0.408 g, 6.0 mmol) and tert-butyldimethylchlorosilane (0.784 g, 5.2 mmol) at room temperature. The reaction mixture was stirred for 2 h, and quenched with saturated aqueous NaHCO$_3$ at 0° C., and extracted with EtOAc. The combined organic layers were washed with $H_2O$, saturated aqueous NaCl, and then dried ($Na_2SO_4$). The desiccant was filtered and the solvent was evaporated at reduced pressure. The residue was purified by column chromatography (silica gel) using n-hexane:CHCl$_3$:EtOAc (50:50:1→20:20:1, v/v) to afford 1.91 g of 50 (100% yield).

$^1$H NMR: δ 7.53–7.25 (m, 5H, aromatic), 7.22 (d, 1H, aromatic), 6.85–6.68 (m, 2H, aromatic), 5.03 (s, 2H, —OCH$_2$Ph), 3.72 (d, 1H, 17β-H), 0.90 (s, 9H, —C(CH$_3$)$_3$), 0.66 (s, 3H, 18-CH$_3$), 0.04 (s, 6H, —Si(CH$_3$)$_2$).

(e) Synthesis of 17α-tert-butyldimethylsilyloxyestra-1,3,5 (10)-trien-3-ol (51):

To a solution of 3-benzyloxy-17α-tert-butyldimethylsilyloxyestra-1,3,5(10)-triene (50, 1.90 g, 4.0 mmol) in THF (30 mL) was added 10% palladium on carbon (0.500 g). The reaction mixture was stirred for 2 h under a hydrogen atmosphere at room temperature. After the catalyst was filtered, the solvent was evaporated at reduced pressure. The residue was purified by column chromatography (silica gel) using n-hexane:EtOAc (10:1→5:1, v/v) to afford 1.45 g of 51 (94% yield) mp: 161–162° C. (silica gel) using n-hexane:EtOAc (10:1→5:1, v/v) to afford 1.45 g of 51 (94% yield) mp: 161–162° C.

$^1$H NMR: δ 7.16 (d, 1H, aromatic), 6.67–6.48 (m, 2H, aromatic), 4.53 (s, 1H, —OH), 3.71 (d, 1H, 17β-H), 0.90 (s, 9H, —C(CH$_3$)$_3$), 0.66 (s, 3H, 18-CH$_3$), 0.04 (s, 6H, —Si(CH$_3$)$_2$); MS (EI): m/z 386 (M$^+$).

(f) Synthesis of 17α-tert-Butyldimethylsilyloxyestra-1,3,5 (10)-triene-3-O-sulfamate (52):

To a solution of chlorosulfonyl isocyanate (0.22 mL, 2.5 mmol) in CH$_2$Cl$_2$ (1.0 mL) was added formic acid (0.5 mL of a CH$_2$Cl$_2$ solution, 5.0 M, 2.5 mmol) at 0° C. The reaction mixture was warmed to room temperature and stirred for 1 h. To a solution of 17α-tert-butyldimethylsilyloxyestra-1,3, 5(10)-trien-3-ol (51, 0.193 g, 0.5 mmol) in DMF (3.0 mL) and THF (1.0 mL) was added sodium hydride (0.100 g of a mineral oil dispersion, 60%, 2.5 mmol) at 0° C. The reaction mixture was stirred for 1 h, and the chlorosulfonyl isocyanate in formic acid was added, and stirring continued for 2 h. The reaction mixture was quenched with saturated aqueous NH$_4$Cl at 0° C., and extracted with EtOAc. The combined organic layers were washed with $H_2O$, saturated aqueous NaCl, and then dried ($Na_2SO_4$). The desiccant was filtered and the solvent was evaporated at reduced pressure. The residue was purified by column chromatography (silica gel) using n-hexane:EtOAc (5:1→3:1, v/v) to afford 0.216 g of 52 (93% yield) mp: 150–151° C.

$^1$H NMR: δ 7.33 (d, 1H, aromatic), 7.13–6.98 (m, 2H, aromatic), 4.87 (s, 2H, —NH$_2$), 3.72 (d, 1H, 17β-H), 0.90 (s, 9H, —C(CH$_3$)$_3$), 0.66 (s, 3H, 18-CH$_3$), 0.04 (s, 6H, —Si(CH$_3$)$_2$); MS (EI): m/z 465 (M$^+$).

EXAMPLE 18

Preparation of 17α-(2'-N,N-Dimethylaminoethoxy) estra-1,3,5(10)-triene-3-O-sulfamate (55)

(a) Synthesis of 3-Benzyloxyestra-1,3,5(10)-trien-17α-ol 17α-O-p-nitrobenzoate (48):

The procedure described in steps (a) and (b) of Example 15 above was used to obtain 41 from 11.

(b) Synthesis of 3-Benzyloxyestra-1,3,5(10)-trien-17α-ol (49):

The procedure described in steps (b) and (c) of Example 17 above was used to obtain 49 from 41.

(c) Synthesis of 3-Benzyloxy-17α-(2'-N,N-dimethylaminoethoxy)estra-1,3,5(10)-triene (53):

To a solution of 3-benzyloxyestra-1,3,5(10)-trien-17α-ol (49, 1.45 g, 4.0 mmol) in DMF (30 mL) were added sodium hydride (2.40 g of a mineral oil dispersion, 60%, 60 mmol) at 0° C., and stirred for 30 min, added 2-N,N-dimethylaminoethylchloride hydrochloride (1.73 g, 12 mmol) and tetrabutylammonium iodide (0.148 g, 0.40 mmol) and stirred for 2 h at 100° C. After the reaction mixture was cooled to room temperature, saturated aqueous $NaHCO_3$ was added and the mixture extracted with EtOAc. The combined organic layers were washed with $H_2O$, saturated aqueous NaCl, and then dried ($Na_2SO_4$). The desiccant was filtered and the solvent was evaporated at reduced pressure. The residue was purified by column chromatography (silica gel) using $CHCl_3$:MeOH (30:1→15:1, v/v) to afford 1.56 g of 53 (90% yield) mp: 190–191° C.

$^1$H NMR: δ 7.53–7.16 (m, 6H, aromatic), 6.83–6.67 (m, 2H, aromatic), 5.03 (s, 2H, —$OCH_2Ph$), 4.05–3.70 (m, 2H, 17α-$OCH_2$—), 3.42 (d, 1H, 17β-H), 2.88 (s, 6H, —N($CH_3$)$_2$), 0.72 (s, 3H, 18—$CH_3$).

(d) Synthesis of 17α-(2'-N,N-Dimethylaminoethoxy)estra-1,3,5 (10)-trien-3-ol (54):

To a solution of 3-benzyloxy-17α-(2'-N,N-dimethylaminoethoxy)estra-1,3,5(10)-triene (53, 1.52 g, 3.5 mmol) in MeOH (20 mL) was added 10% palladium on carbon (0.500 g). The reaction mixture was stirred for 2 h under a hydrogen atmosphere at room temperature. After the catalyst was filtered, the solvent was evaporated at reduced pressure. The residue was washed with $Et_2O$ to afford 1.02 g of 76 (85% yield) mp: 233–235° C.

$^1$H NMR ($CDCl_3$-DMSO-$d_6$): δ 7.10 (d, 1H, aromatic), 6.72–6.55 (m, 2H, aromatic), 4.05–3.70 (m, 2H, 17α-$OCH_2$—), 3.41 (d, 1H, 17β-H), 2.86 (s, 6H, —N($CH_3$)$_2$), 0.71 (s, 3H, 18-$CH_3$); MS (DCI): m/z 344 ($M^+$+H).

(e) Synthesis of 17α-(2'-N,N-Dimethylaminoethoxy)estra-1,3,5(10)-triene-3-O-sulfamate (55):

To a solution of chlorosulfonyl isocyanate (0.22 mL, 2.5 mmol) in $CH_2Cl_2$ (1.0 mL) was added formic acid (0.5 mL of a $CH_2Cl_2$ solution, 5.0 M, 2.5 mmol) at 0° C. The reaction mixture was warmed to room temperature and stirred for 1 h. To a solution of 17α-(2'-N,N-dimethylaminoethoxy)estra-1,3,5(10)-trien-3-ol (54, 0.172 g, 0.5 mmol) in DMF (3.0 mL) and THF (1.0 mL) was added sodium hydride (0.100 g of a mineral oil dispersion, 60%, 2.5 mmol) at 0° C. The reaction mixture was stirred for 1 h, and the chlorosulfonyl isocyanate in formic acid was added, and stirring continued for 4 h. The reaction mixture was quenched with saturated aqueous $NaHCO_3$ at 0° C., and extracted with EtOAc. The combined organic layers were washed with $H_2O$, saturated aqueous NaCl, and then dried ($Na_2SO_4$). The desiccant was filtered and the solvent was evaporated at reduced pressure. The residue was purified by column chromatography (silica gel) using $CHCl_3$:MeOH (12:1→7:1, v/v) to afford 0.116 g of 55 (55% yield) mp: 136–138° C.

$^1$H NMR: δ 7.27 (d, 1H, aromatic), 7.15–6.98 (m, 2H, aromatic), 6.20–5.65 (m, 2H, —$NH_2$), 3.68–3.37 (m, 2H, 17α-$OCH_2$—), 3.31 (d, 1H, 17β-H), 2.33 (s, 6H, —N($CH_3$)$_2$), 0.67 (s, 3H, 18-$CH_3$); MS (DCI): m/z 423 ($M^+$+H).

The following scheme illustrates the synthetic steps carried out in Examples 19 and 20 to make the estrone sulfatase inhibitory compounds (59) and (65):

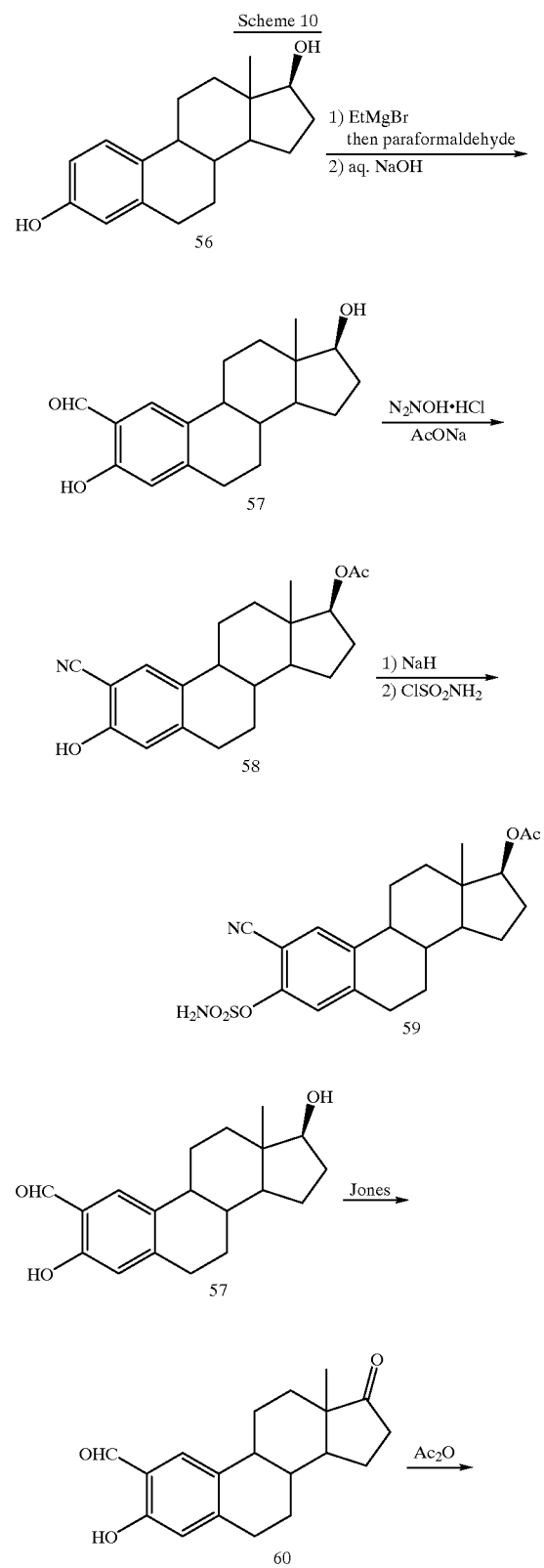

Scheme 10

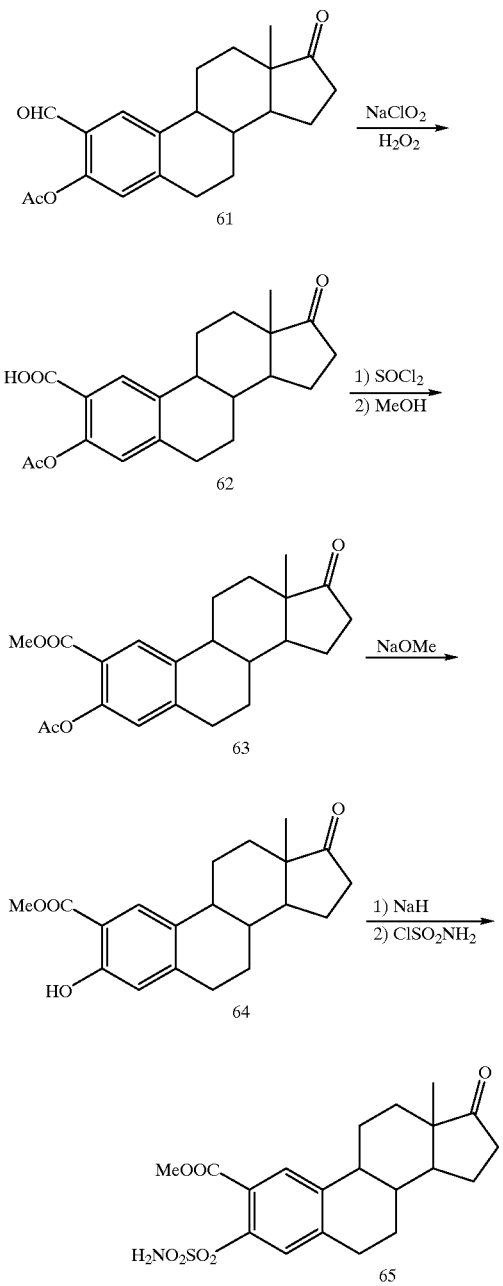

EXAMPLE 19

Preparation of 2-Cyanoestra-1,3,5(10)-trien-17β-ol-3-O-sulfamate 17β-O-acetate (59)

(a) Synthesis of 3,17β-Dihydroxyestra-1,3,5(10)-triene-2-carboxaldehyde (57):

To a suspension of magnesium (2.07 g, 85 mmol) in THF (20 mL) was added bromoethane (8.9 mL, 119 mmol) dissolved in THF (15 mL) at room temperature.

Estradiol (56, 4.63 g, 17 mmol) dissolved in THF (40 mL) was added to the reaction mixture, and stirring continued for 30 min. The solvent was removed at reduced pressure, and to the residue were added benzene (200 mL), hexamethylphosphoric triamide (7.4 mL, 42.5 inmol) and paraformaldehyde (7.00 g). Stirring was continued for 20 h at 80° C. After the reaction mixture was cooled to room temperature, 5 N HCl (150 mL) was added and the mixture extracted with EtOAc. The combined organic layers were washed with $H_2O$, saturated aqueous NaCl, and then dried ($Na_2SO_4$). The desiccant was filtered and the solvent was evaporated at reduced pressure. The residue was dissolved in MeOH (200 ML), 20% aqueous sodium hydroxide (25 mL) added, and the mixture stirred for 30 min at room temperature.

The reaction mixture was acidified with 5 N HCl at 0° C., the solvent evaporated at reduced pressure, and the residue extracted with EtOAc. The combined organic layers were washed with $H_2O$, saturated aqueous NaCl, and then dried ($N_2SO_4$). The desiccant was filtered and the solvent was evaporated at reduced pressure. The residue was purified by column chromatography (silica gel) using n-hexane:THF (5:1→2:1, v/v) to afford 4.81 g of 57 (94% yield) mp: 219–221° C.

$^1$H NMR: δ 10.77 (s, 1H, —OH), 9.81 (s, 1H, —CHO), 7.42 (s, 1H, aromatic), 6.70 (s, 1H, aromatic), 3.74 (t, 1H, 17α-H), 0.79 (s, 3H, 18-$CH_3$); MS (EI): m/z 300 ($M^+$).

(b) Synthesis of 2-Cyanoestra-1,3,5(10)-trien-3,17-β-diol 17β-O-acetate (58):

To a suspension of 3,17β-dihydroxyestra-1,3,5(10)-triene-2-carboxaldehyde (57, 0.300 g, 1.0 mmol) in acetic acid (6.0 mL) was added sodium acetate (1.23 g, 15 mmol), hydroxylamine hydrochloride (0.139 g, 2.0 mmol). The reaction mixture was stirred for 18 h under the reflux condition. After the reaction mixture was cooled to room temperature, diluted with EtOAc, and washed with $H_2O$, saturated aqueous NaCl, and then dried ($MgSO_4$). The desiccant was filtered and the solvent was evaporated at reduced pressure. The residue was purified by column chromatography (silica gel) using n-hexane:EtOAc (3:1→2:1, v/v) to afford 0.259 g of 58 (76% yield) mp: 249–251° C.

$^1$H NMR: δ 7.38 (s, 1H, aromatic), 6.68 (s, 1H, aromatic), 4.69 (t, 1H, 17α-H), 2.07 (s, 3H, —$OCOCH_3$), 0.83 (s, 3H, 18-$CH_3$); MS (EI): m/z 339 ($M^+$); IR (nujol): 2229 $cm^{-1}$, 1733 $cm^{-1}$.

(c) Synthesis of 2-Cyanoestra-1,3,5(10)-trien-17β-ol-3-O-sulfamate 17β-O-acetate (59):

To a solution of chlorosulfonyl isocyanate (3.0 mL, 35 mmol) in $CH_2Cl_2$ (14 mL) was added formic acid (7.0 mL of a $CH_2Cl_2$ solution, 5.0 M, 35 mmol) at 0° C. The reaction mixture was warmed to room temperature and stirred for 1 h. To a solution of 3-cyanoestra-1,3,5(10)-trien-3-ol-17β-O-acetate (58, 2.38 g, 7.0 mmol) in DMF (40 mL) was added sodium hydride (1.40 g of a mineral oil dispersion, 60%, 35 mmol) at 0° C. The reaction mixture was stirred for 1 h, and the chlorosulfonyl isocyanate in formic acid was added, and stirring continued for 5 h. The reaction mixture was quenched with saturated aqueous $NH_4Cl$ at 0° C., and extracted with EtOAc. The combined organic layers were washed with $H_2O$, saturated aqueous NaCl, and then dried ($Na_2SO_4$). The desiccant was filtered and the solvent was evaporated at reduced pressure. The residue was purified by column chromatography (silica gel) using $CHCl_3$:EtOAc (5:1→2:1, v/v) to afford 0.676 g of the starting material 58 (29% yield) and 1.39 g of 59 (47% yield) mp: 182–183° C.

$^1$H NMR: d 7.56 (s, 1H, aromatic), 7.25 (s, 1H, aromatic), 5.43 (s, 2H, —$NH_2$), 4.70 (t, 1H, 17α-H), 2.07 (s, 3H, —OCOCH$_3$), 30.83 (s, 3H, 18-CH$_3$); MS (EI): m/z 418 (M$^+$); HRMS calcd for C$_{21}$H$_{25}$N$_2$O$_5$S$_1$ 417.1484, found 417.1476; IR (nujol): 3319 cm$^{-1}$, 3216 cm$^{-1}$, 2233 cm$^{-1}$, 1703 cm$^{-1}$.

EXAMPLE 20

Preparation of 2-Methoxycarbonylestra-1,3,5(10)-trien-17-one-3-O-sulfamate (65)

(a) Synthesis of 3,17β-Dihydroxyestra-1,3,5(10)-triene-2-carboxaldehyde (57):

The procedure described in step (a) of Example 19 above was used to obtain 57 from 56.

(b) Synthesis of 3-Hydroxyestra-1,3,5(10)-trien-17-one-2-carboxaldehyde (60):

To a solution of 3,17β-dihydroxyestra-1,3,5(10)-triene-2-carboxaldehyde (57, 0.300 g, 1.0 mmol) in acetone (20 mL) was added Jones reagent (0.5 mL) at 0° C. The reaction mixture was stirred for 5 min, and quenched with 2-propanol, and extracted with EtOAc. The combined organic layers were washed with H$_2$O, saturated aqueous NaCl, and then dried (MgSO$_4$). The desiccant was filtered and the solvent was evaporated at reduced pressure. The residue was purified by column chromatography (silica gel) using n-hexane:THF (4:1→3:1, v/v) to afford 0.185 g of 60 (62% yield) mp: 154–157° C.

$^1$H NMR: d 10.83 (s, 1H, —OH), 9.86 (s, 1H, —CHO), 7.47 (s, 1H, aromatic), 6.77 (s, 1H, aromatic), 0.97 (s, 3H, 18-CH$_3$); MS (EI): m/z 298 (M$^+$).

(c) Synthesis of 3-Acetoxyestra-1,3,5(10)-trien-17-one-2-carboxaldehyde (61):

To a solution of 3-hydroxyestra-1,3,5(10)-trien-17-one-2-carboxaldehyde (60, 1.92 g, 6.43 mmol) of CH$_2$Cl$_2$ (30 mL) was added triethylamine (2.3 mL, 16 mmol) and acetic anhydride (0.94 mL, 9.6 mmol) at room temperature. The reaction mixture was stirred for 16 h, H$_2$O was added, and the mixture was extracted with EtOAc. The combined organic layers were washed with H$_2$O, saturated aqueous NaCl, and then dried (Na$_2$SO$_4$). The desiccant was filtered and the solvent was evaporated at reduced pressure. The residue was purified by column chromatography (silica gel) using n-hexane:EtOAc (2:1→3:2, v/v) to afford 2.08 g of 61 (95% yield) mp: 179–181° C.

$^1$H NMR: d 10.06 (s, 1H, —CHO), 7.83 (s, 1H, aromatic), 6.94 (s, 1H, aromatic), 2.42 (s, 3H, —OCOCH$_3$), 0.96 (s, 3H, 18-CH$_3$).

(d) Synthesis of 3-Acetoxyestra-1,3,5(10)-trien-17-one-2-carboxylic acid (62):

To a suspension of 3-acetoxyestra-1,3,5(10)-trien-17-one-2-carboxaldehyde (61, 1.20 g, 3.5 mmol) in acetonitrile (17 mL) and H$_2$O (2.1 mL) were added 30% hydrogen peroxide (0.53 mL) and sodium phosphate monobasic (1.79 g) at room temperature. Sodium chlorite (0.935 g in a H$_2$O (7.0 mL) solution) was added dropwise to the reaction mixture over a 1 h period, and stirring continued for an additional 2 h at room temperature. The reaction mixture was quenched with sodium sulfite, acidified with 10% HCl, and extracted with EtOAc. The combined organic layers were washed with H$_2$O, saturated aqueous NaCl, and then dried (Na$_2$SO$_4$). The desiccant was filtered and the solvent was evaporated at reduced pressure. The residue was washed with Et$_2$O to afford 1.06 g of 62 (85% yield) mp: 180–181° C.

$^1$H NMR: d 8.04 (s, 1H, aromatic), 6.86 (s, 1H, aromatic), 2.33 (s, 3H, —OCOCH$_3$), 0.92 (s, 3H, 18-CH$_3$); MS (EI): m/z 356 (M$^+$).

(e) Synthesis of Methyl 3-Acetoxyestra-1,3,5(10)-trien-17-one-2-carboxylate (63):

To a solution of 3-acetoxyestra-1,3,5(10)-trien-17-one-2-carboxylic acid (62, 1.07 g, 3.0 mmol) in dichloroethane (10 mL) was added thionyl chloride (0.28 mL, 3.9 mmol) and DMF (1 drop) at room temperature. The reaction mixture was stirred for 30 min at 80° C. After the reaction mixture was cooled to 0° C., MeOH (5.0 mL) and triethylamine (1.0 mL) were added, and stirred for 1 h. The reaction mixture was diluted with EtOAc and washed with H$_2$O, saturated aqueous NaCl, and then dried (Na$_2$SO$_4$). The desiccant was filtered and the solvent was evaporated at reduced pressure. The residue was purified by column chromatography (silica gel) using n-hexane:EtOAc (3:1→3:2, v/v) to afford 0.764 g of 63 (69% yield) mp: 182–183° C.

$^1$H NMR: d 7.95 (s, 1H, aromatic), 6.83 (s, 1H, aromatic), 3.85 (s, 3H, —COOCH$_3$), 2.34 (s, 3H, —OCOCH$_3$), 0.92 (s, 3H, 18-CH$_3$).

(f) Synthesis of Methyl 3-Hydroxyestra-1,3,5(10)-trien-17-one-2-carboxylate (64):

To a solution of methyl 3-acetoxyestra-1,3,5(10)-trien-17-one-2-carboxylate (63, 0.746 g, 2.0 mmol) in THF (10 mL) and MeOH (15 mL) was added sodium hydride (0.240 g of a mineral oil dispersion, 60%, 6.0 mmol) at 0° C. The reaction mixture was stirred for 30 min, and quenched with saturated aqueous NH$_4$Cl at 0° C., and extracted with EtOAc. The combined organic layers were washed with H$_2$O, saturated aqueous NaCl, and then dried (Na$_2$SO$_4$). The desiccant was filtered and the solvent was evaporated at reduced pressure. The residue was purified by column chromatography (silica gel) using n-hexane:EtOAc (3:1, v/v) to afford 0.572 g of 64 (87% yield) mp: 178–179° C.

$^1$H NMR: d 10.50 (s, 1H, —OH), 7.73 (s, 1H, aromatic), 6.72 (s, 1H, aromatic), 3.93 (s, 3H, —COOCH$_3$), 0.92 (s, 3H, 18-CH$_3$); MS (EI): m/z 328 (M$^+$).

(g) Synthesis of 2-Methoxycarbonylestra-1,3,5(10)-trien-17-one-3-O-sulfamate (65):

To a solution of chlorosulfonyl isocyanate (0.43 mL, 5.0 mmol) in CH$_2$Cl$_2$ (2.0 mL) was added formic acid (1.0 mL of a CH$_2$Cl$_2$ solution, 5.0 M, 5.0 mmol) at 0° C. The reaction mixture was warmed to room temperature and stirred for 1 h. To a solution of methyl 3-hydroxyestra-1,3,5(10)-trien-17-one-2-carboxylate (64, 0.328 g, 1.0 mmol) in DMF (5.0 mL) and THF (2.0 mL) was added sodium hydride (0.20 g of a mineral oil dispersion, 60%, 5.0 mmol) at 0° C. The reaction mixture was stirred for 1 h, and the chlorosulfonyl isocyanate in formic acid was added, and stirring continued for 2 h at 0° C. and additional 14 h at room temperature. The reaction mixture was quenched with saturated aqueous NH$_4$Cl at 0° C., and extracted with EtOAc. The combined organic layers were washed with H$_2$O, saturated aqueous NaCl, and then dried (Na$_2$SO$_4$). The desiccant was filtered and the solvent was evaporated at reduced pressure. The residue was purified by column chromatography (silica gel) using n-hexane:EtOAc (3:1→1:1, v/v) to afford 0.233 g of the starting material 64 (71% yield) and 0.055 g of 65 (14% yield) mp: 139–140° C.

$^1$H NMR: d 7.85 (s, 1H, aromatic), 7.20 (s, 1H, aromatic), 3.91 (s, 3H, —COOCH$_3$), 0.92 (s, 3H, 18-CH$_3$); MS (DCI): m/z 425 (M$^+$+NH$_4^+$).

The following scheme illustrates the synthetic steps carried out in Examples 21, 22 and 23 to make the estrone sulfatase inhibitory compounds (67), (69) and (71):

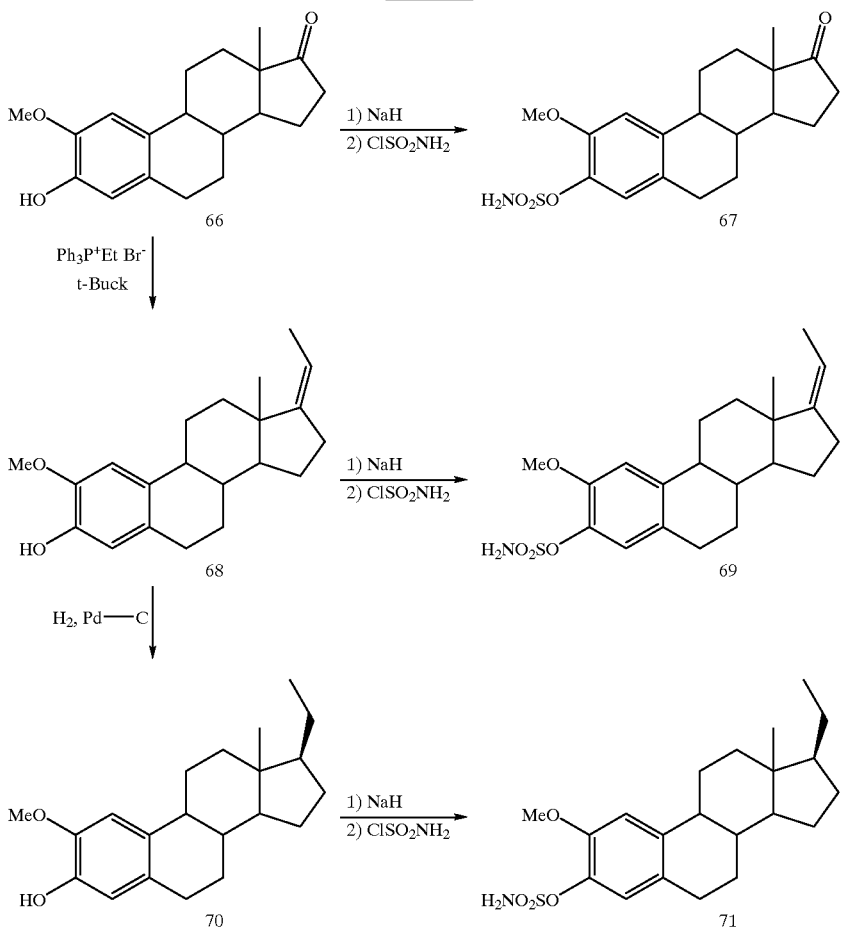

Scheme 11

EXAMPLE 21

Preparation of 2-Methoxyestra-1,3,5(10)-trien-17-one-3-O-sulfamate (67)

To a solution of chlorosulfonyl isocyanate (0.43 mL, 5.0 mmol) in CH$_2$Cl$_2$ (2.0 mL) was added formic acid (1.0 mL of a CH$_2$Cl$_2$ solution, 5.0 M, 5.0 mmol) at 0° C. The reaction mixture was warmed to room temperature and stirred for 1 h. To a solution of 2-methoxyestra-1,3,5(10)-trien-3-ol (66, 0.300 g, 1.0 mmol) in DMF (5.0 mL) was added sodium hydride (0.200 g of a mineral oil dispersion, 60%, 5.0 mmol) at 0° C. The reaction mixture was stirred for 1 h, and the chlorosulfonyl isocyanate in formic acid was added, and stirring continued for 1 h and additional 2 h at room temperature. The reaction mixture was quenched with saturated aqueous NH$_4$Cl at 0° C., and extracted with EtOAc. The combined organic layers were washed with H$_2$O, saturated aqueous NaCl, and then dried (Na$_2$SO$_4$). The desiccant was filtered and the solvent was evaporated at reduced pressure. The residue was purified by column chromatography (silica gel) using n-hexane:EtOAc (2:1→1:1, v/v) to afford 0.210 g of 67 (55% yield) mp: 176–177° C.

$^1$H NMR: d 7.06 (s, 1H, aromatic), 6.93 (s, 1H, aromatic), 5.06 (s, 2H, —NH$_2$), 3.88 (s, 3H, —OCH$_3$), 0.92 (s, 3H, 18-CH$_3$); MS (EI): m/z 379 (M$^+$); HRMS calcd. for C$_{19}$H$_{24}$N$_1$O$_5$S$_1$. 378.1375; found, 378.1368.

EXAMPLE 22

Preparation of 2-Methoxy-[17(20)Z]-19-norpregna-1,3,5(10),17(20)-tetraene-3-O-sulfamate (69)

(a) Synthesis of 2-Methoxy-[17(20)Z]-19-norpregna-1,3,5 (10),17(20)-tetraen-3-ol (68):

To a suspension of ethyltriphenylphosphonium bromide (2.14 g, 6.0 mmol) in THF (15 mL) was added potassium tert-butoxide (0.670 g, 6.0 mmol) and stirred for 30 min at room temperature. The reaction mixture was added 2-methoxyestra-1,3,5(10)-trien-3-ol (66), 0.600 g, 2.0 mmol), stirred for 6 h at reflux condition. The reaction mixture was quenched with saturated aqueous NH$_4$Cl at 0° C. and extracted with EtOAc. The combined organic layers were washed with H$_2$O, saturated aqueous NaCl, and then dried (Na$_2$SO$_4$). The desiccant was filtered and the solvent was evaporated at reduced pressure. The residue was purified by column chromatography (silica gel) using n-hexane:EtOAc (15:1→10:1, v/v) to afford 0.571 g of 68 (91% yield) mp: 126–127° C.

$^1$H NMR: d 6.80 (s, 1H, aromatic), 6.64 (s, 1H, aromatic), 5.42 (s, 1H, —OH), 5.23–5.08 (m, 1H, =CH—CH$_3$), 3.86 (s, 3H, —OCH$_3$), 0.92 (s, 3H, 18-CH$_3$); MS (EI): m/z 312 (M$^+$).

(b) Synthesis of 2-Methoxy-[17(20)Z]-19-norpregna-1,3,5 (10),17(20)-tetraene-3-O-sulfamate (69):

To a solution of chlorosulfonyl isocyanate (0.22 mL, 2.5 mmol) in CH$_2$Cl$_2$ (1.0 mL) was added formic acid (0.5 mL of a CH$_2$Cl$_2$ solution, 5.0 M, 2.5 mmol) at 0° C. The reaction mixture was warmed to room temperature and stirred for 1 h. To a solution of 2-methoxy-[17(20)Z]-19-norpregna-1,3,5(10),17(20)-tetraen-3-ol (68, 0.156 g, 0.5 mmol) in DMF (3.0 mL) was added sodium hydride (0.100 g of a mineral oil dispersion, 60%, 2.5 mmol) at 0° C. The reaction mixture was stirred for 1 h, and the chlorosulfonyl isocyanate in formic acid was added, and stirring continued for 2 h. The reaction mixture was quenched with saturated aqueous NH$_4$Cl at 0° C., and extracted with EtOAc. The combined organic layers were washed with H$_2$O, saturated aqueous NaCl, and then dried (Na$_2$SO$_4$). The desiccant was filtered and the solvent was evaporated at reduced pressure. The residue was purified by column chromatography (silica gel) using n-hexane: EtOAc (5:1→3:1, v/v) to afford 0.191 g of 69 (98% yield) mp: 171–172° C.

$^1$H NMR: d 7.03 (s, 1H, aromatic), 6.94 (s, 1H, aromatic), 5.25–5.10 (m, 1H, =C$\underline{H}$—CH$_3$), 5.00 (s, 2H, —NH$_2$), 3.87 (s, 3H, —OCH$_3$), 0.92 (s, 3H, 18-CH$_3$); MS (DCI): m/z 409 (M$^+$+NH$_4^+$), 392 (M$^+$+H).

EXAMPLE 23

Preparation of 2-Methoxy-19-norpregna-1,3,5(10)-triene-3-O-sulfamate (71)

(a) Synthesis of 2-Methoxy-[17(20)Z]-19-norpregna-1,3,5(10),17(20)-tetraen-3-ol (68):

The procedure described in step (a) of Example 22 above was used to obtain 68 from 66.

(b) Synthesis of 2-Methoxy-19-norpregna-1,3,5(10)-trien-3-ol (70):

To a solution of 2-methoxy-[17(20)Z]-19-norpregna-1,3,5(10),17(20)-tetraen-3-ol (68, 0.312 g, 1.0 mmol) in MeOH (3.0 mL) and THF (3.0 mL) was added 10% palladium on carbon (0.150 g). The reaction mixture was stirred for 2 h under a hydrogen atmosphere at room temperature. After the catalyst was filtered, the solvent was evaporated at reduced pressure. The residue was purified by column chromatography (silica gel) using n-hexane:EtOAc (10:1, v/v) to afford 0.287 g of 70 (91% yield) mp: 124–125° C.

$^1$H NMR: d 6.80 (s, 1H, aromatic), 6.64 (s, 1H, aromatic), 5.41 (s, 1H, —OH), 3.86 (s, 3H, —OCH$_3$), 0.90 (t, 3H, 21-CH$_3$), 0.61 (s, 3H, 18-CH$_3$); MS (EI): (M$^+$).

(c) Synthesis of 2-Methoxy-19-norpregna-1,3,5(10)-triene-3-O-sulfamate (71):

By using the procedure described in step (b) of Example 22 above, beginning with 2-methoxy-19-norpregna-1,3,5(10)-trien-3-ol (70, 0.157 g, 0.5 mmol), 0.191 g of 71 (97% yield; mp: 191–192° C.) was obtained after chromatography (n-hexane:EtOAc 5:1→2:1, v/v).

$^1$H NMR: d 7.03 (s, 1H, aromatic), 6.94 (s, 1H, aromatic), 4.98 (s, 2H, —NH$_2$), 3.87 (s, 3H, —OCH$_3$), 0.91 (s, 3H, 21-CH$_3$), 0.62 (s, 3H, 18-CH$_3$); MS (DCI): m/z 411 (M$^+$+NH$_4^+$), 394 (M$^+$+H).

The following scheme illustrates the synthetic steps carried out in Examples 24 and 25 to make the estrone sulfatase inhibitory compounds (73) and (75):

Scheme 12

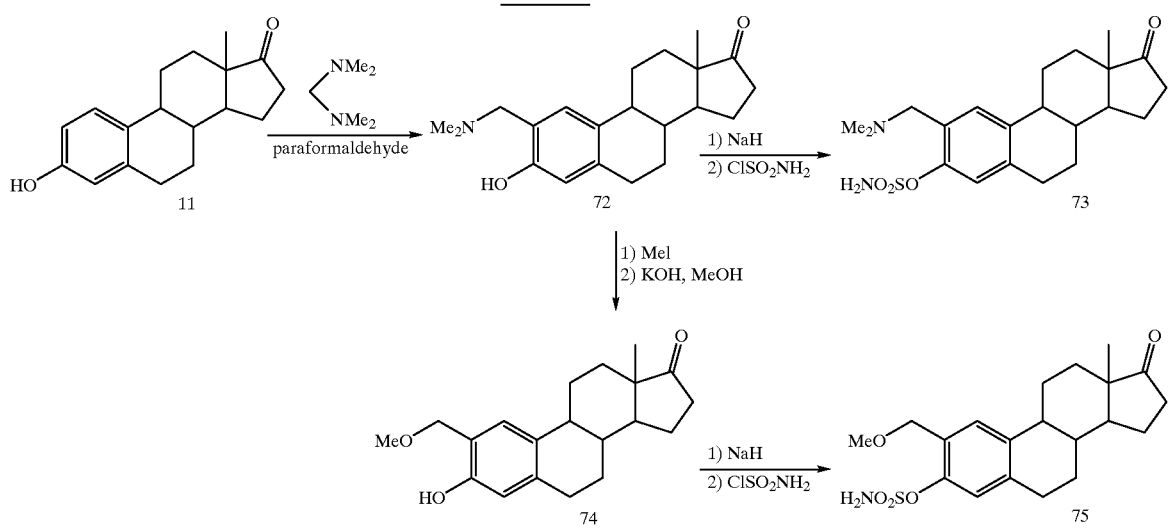

EXAMPLE 24

Preparation of 2-Dimethylaminomethylestra-1,3,5(10)-trien-17-one-3-O-sulfamate (73)

(a) Synthesis of 2-Dimethylaminomethyl-3-hydroxyestra-1,3,5(10)-trien-17-one (72):

To a suspension of estrone (11, 5.40 g, 20 mmol) in EtOH (100 mL) and benzene (60 mL) were added paraformaldehyde (0.600 g, 20 mmol) and N,N,N',N'-tetramethyldiaminomethane (5.5 mL, 40 mmol), and stirred for 20 h at 80° C. After the reaction mixture was cooled to 0° C., 5 N HCl was added. The aqueous layer was washed with Et$_2$O, and basified with aqueous NH$_4$OH. The precipitate was collected by filtration and washed with H$_2$O, and recrystallized from EtOH to afford 4.37 g of 72 (67% yield) mp: 172–173° C.

$^1$H NMR: d 6.86 (s, 1H, aromatic), 6.57 (s, 1H, aromatic), 3.59 (AB type, 2H, —C$\underline{H_2}$—N(CH$_3$)$_2$), 2.31 (s, 6H, —N(CH$_3$)$_2$), 0.91 (s, 3H, 18-CH$_3$); MS (EI): m/z 327 M$^+$).

(b) Synthesis of 2-Dimethylaminomethylestra-1,3,5(10)-trien-17-one-3-O-sulfamate (73):

To a solution of chlorosulfonyl isocyanate (0.46 mL, 5.0 mmol) in CH$_2$Cl$_2$ (2.0 mL) was added formic acid (1.0 mL of a CH$_2$Cl$_2$ solution, 5.0 M, 5.0 mmol) at 0° C. The reaction mixture was warmed to room temperature and stirred for 1 h. To a solution of 2-dimethylaminomethyl-3-hydroxyestra-1,3,5(10)-trien-17-one (72, 0.327 g, 1.0 mmol) in DMF (5.0 mL) was added sodium hydride (0.200 g of a mineral oil dispersion, 60%, 5.0 mmol) at 0° C. The reaction mixture was stirred for 1 h, and the chlorosulfonyl isocyanate in formic acid was added; stirring then continued for 3 h. The reaction mixture was quenched with saturated aqueous NaHCO$_3$ at 0° C., and extracted with EtOAc. The combined organic layers were washed with H$_2$O, saturated aqueous NaCl, and then dried (Na$_2$SO$_4$). The desiccant was filtered and the solvent was evaporated at reduced pressure. The residue was purified by column chromatography (silica gel) using n-hexane:acetone (3:1→3:2, v/v) to afford 0.093 g of the starting material 72 (28% yield) and 0.115 g of 73 (28% yield) mp: 148–149° C.

NMR: d 7.21 (s, 1H, aromatic), 7.14 (s, 1H, aromatic), 3.48 (s, 2H, —C$\underline{H}_2$—N(CH$_3$)2), 2.30 (s, 6H, —N(CH$_3$)$_2$), 0.92 (s, 3H, 18-CH$_3$); MS (DCI): m/z 407 (M$^+$+H).

EXAMPLE 25

Preparation of 2-Methoxymethylestra-1,3,5(10)-trien-17-one-3-O-sulfamate (75)

(a) Synthesis of 2-Dimethylaminomethyl-3-hydroxyestra-1,3,5(10)-trien-17-one (72):

The procedure described in step (a) of Example 24 above was followed to obtain 72.

(b) Synthesis of 3-Hydroxy-2-methoxymethylestra-1,3,5(10)-trien-17-one (74):

To a suspension of 2-dimethylaminomethyl-3-hydroxyestra-1,3,5(10)-trien-17-one (72, 2.0 g, 6.1 mmol) in Et$_2$O (200 mL) was added iodemethane (10 mL, 161 mmol) and stirred for 20 h at room temperature. The precipitate was collected by filtration and washed with Et$_2$O. The solid was dissolved in MeOH (50 mL) and added potassium hydroxide (5.0 g, 85%, 76 mmol), and stirred for 3 h at reflux condition. After the reaction mixture was cooled to room temperature, solvent was evaporated at reduced pressure until half volume. The reaction mixture was acidified with 5 N HCl at 0° C., and extracted with Et$_2$O. The combined organic layers were washed with H$_2$O, saturated aqueous NaCl, and then dried (Na$_2$SO$_4$). The desiccant was filtered and the solvent was evaporated at reduced pressure. The residue was purified by column chromatography (silica gel) using CHCl$_3$:EtOAc (15:1→10:1, v/v) to afford 1.34 g of 74 (88% yield) mp: 149–151° C.

$^1$H NMR: δ 6.93 (s, 1H, aromatic), 6.63 (s, 1H, aromatic), 4.62 (AB type, 2H, —C$\underline{H}_2$—OCH$_3$), 3.43 (s, 3H, —OCH$_3$), 0.91 (s, 3H, 18-CH$_3$); MS (EI): m/z 314 (M$^+$).

(c) Synthesis of 2-Methoxymethylestra-1,3,5(10)-trien-17-one-3-O-sulfamate (75):

To a solution of chlorosulfonyl isocyanate (0.46 mL, 5.0 mmol) in CH$_2$Cl$_2$ (2.0 mL) was added formic acid (1.0 mL of a CH$_2$Cl$_2$ solution, 5.0 M, 5.0 mmol) at 0° C. The reaction mixture was warmed to room temperature and stirred for 1 h. To a solution of 3-hydroxy-2-methoxymethylestra-1,3,5 (10)-trien-17-one (74, 0.314 g, 1.0 mmol) in DMF (5.0 mL) was added sodium hydride (0.200 g of a mineral oil dispersion, 60%, 5.0 mmol) at 0° C. The reaction mixture was stirred for 1 h, and the chlorosulfonyl isocyanate in formic acid was added, and stirring continued for 1 h. The reaction mixture was quenched with saturated aqueous NH$_4$Cl at 0° C., and extracted with EtOAc. The combined organic layers were washed with H$_2$O, saturated aqueous NaCl, and then dried (Na$_2$SO$_4$). The desiccant was filtered and the solvent was evaporated at reduced pressure. The residue was purified by column chromatography (silica gel) using CHCl$_3$:EtOAc (10:1→3:1, v/v) to afford 0.321 g of 75 (82% yield) mp: 173–174° C.

$^1$H NMR: δ 7.30 (s, 1H, aromatic), 7.20 (s, 1H, aromatic), 5.39 (S, 2H, —NH$_2$), 4.47 (S, 2H, —C$\underline{H}_2$—OCH$_3$), 3.44 (s, 3H, —OCH$_3$), 0.92 (s, 3H, 18-CH$_3$); MS (EI): m/z 393 (M$^+$).

The following scheme illustrates the synthetic steps carried out in Examples 26 through 31 to make compounds (77), (78), (83), (88), (93), and (96):

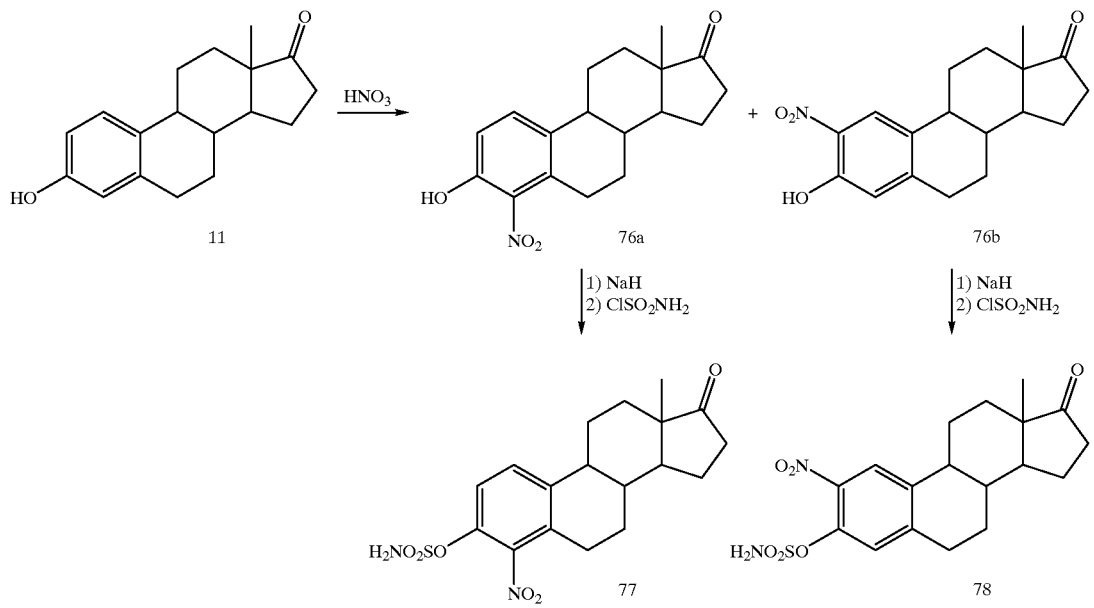

Scheme 13

-continued
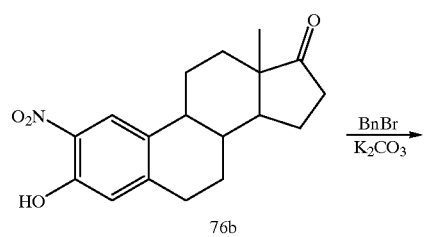 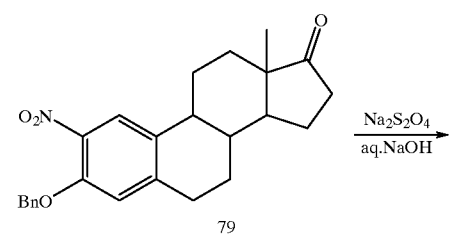
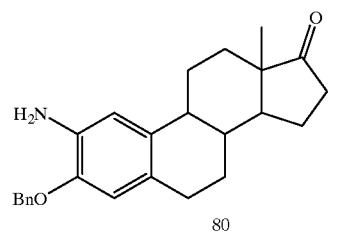 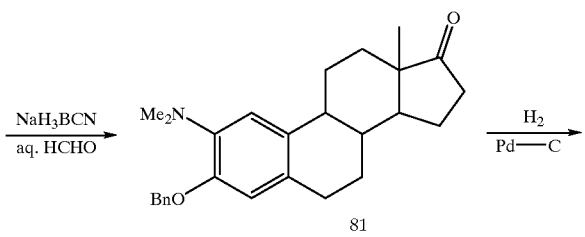
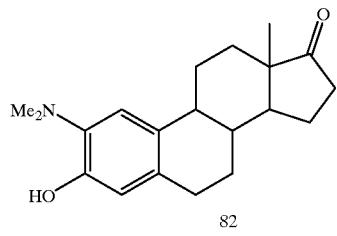 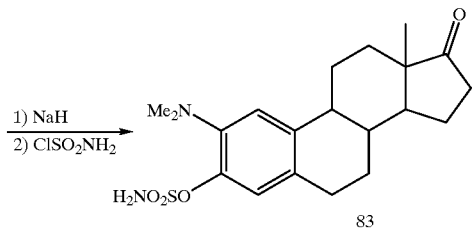
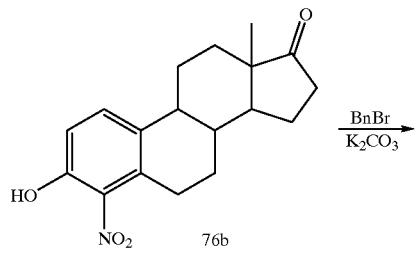 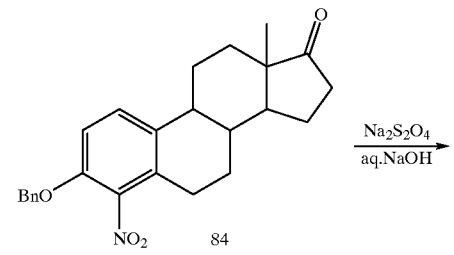
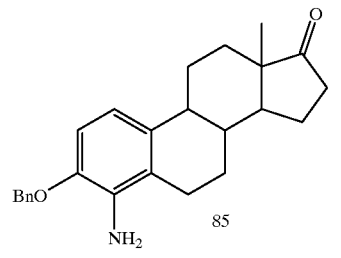 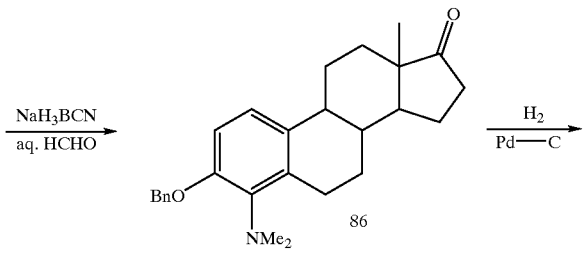
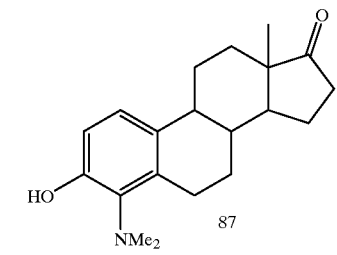 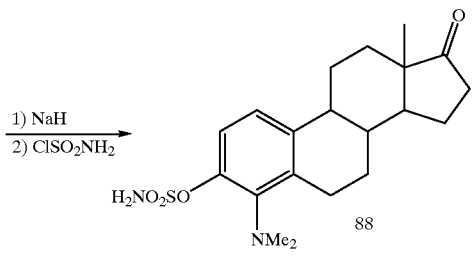

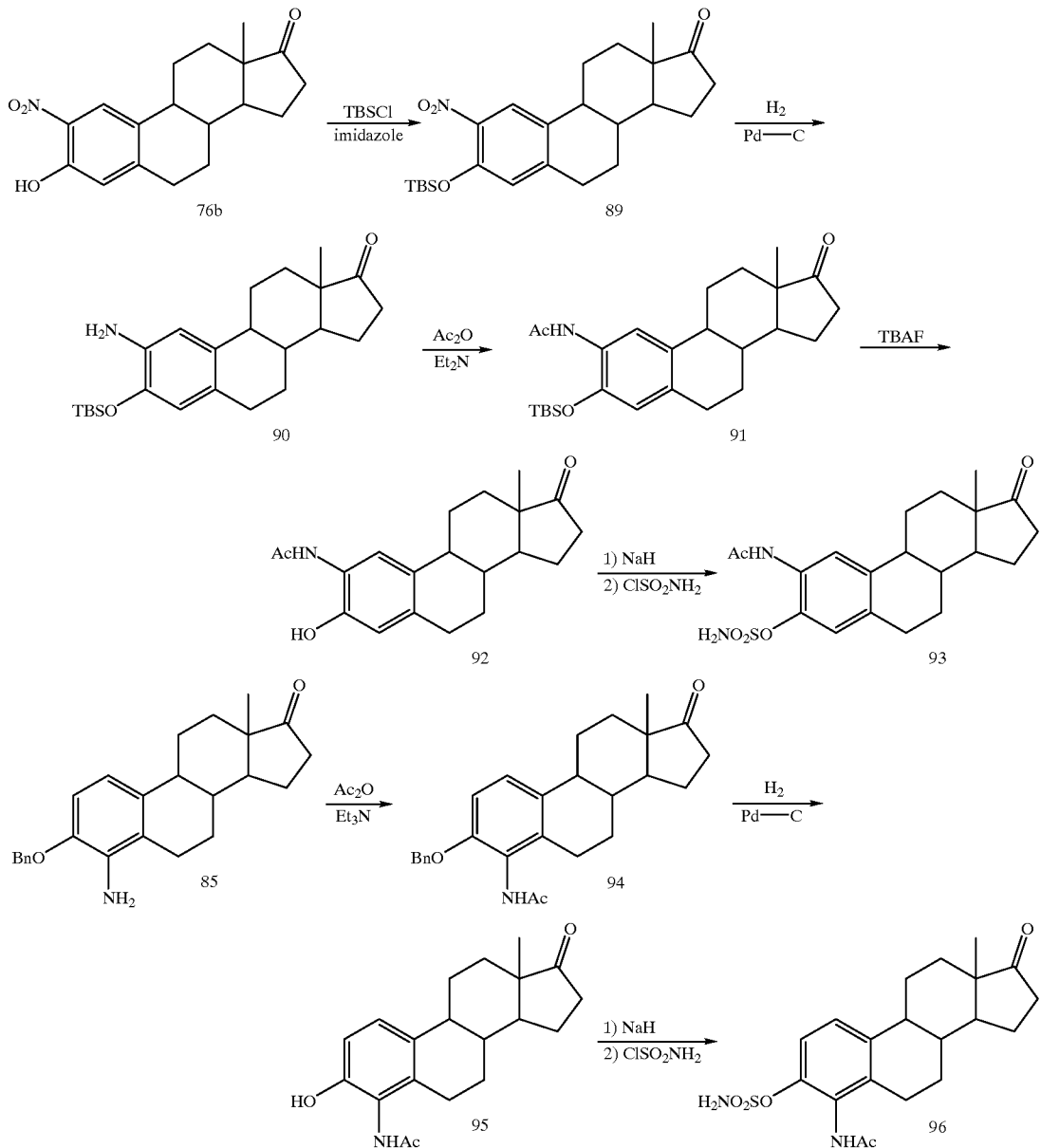

EXAMPLE 26

Preparation of 4-Nitroestra-1,3,5(10)-trien-17-one-3-O-sulfamate (77)

(a) Synthesis of 3-Hydroxy-4-nitroestra-1,3,5(10)-trien-17-one (76a) and 3-Hydroxy-2-nitroestra-1,3,5(10)-trien-17-one (76b):

To a suspension of estrone (11, 8.11 g, 30 mmol) in acetic acid (250 mL) was heated to 120° C. and cooled to 50° C. To the reaction mixture was added 70% nitric acid (2.27 mL, 36 nunol, in an acetic acid (8.0 mL) solution) at 50° C., and stirred for 20 h at room temperature. The precipitate was filtered and washed with acetic acid, $H_2O$, $Et_2O$ to afford 1.18 g of 76a (13% yield) mp: >250° C. To the filtrate was added $H_2O$; it was then extracted with $Et_2O$. The combined organic layers were washed with $H_2O$, saturated aqueous NaCl, and then dried ($Na_2SO_4$). The desiccant was filtered and the solvent was evaporated at reduced pressure. The residue was purified by column chromatography (silica gel) using n-hexane:EtOAc (2:1, v/v) to afford 3.25 g of 76b (34% yield) mp: 178–180° C.

76a: $^1H$ NMR: δ 9.46 (s, 1H, —OH), 7.52 (d, 1H, aromatic), 7.03 (d, 1H, aromatic), 0.98 (s, 3H, 18-$CH_3$); MS (EI): m/z 315 ($M^+$).

76b: $^1H$ NMR: δ 10.44 (s, 1H, —OH), 8.02 (s, 1H, aromatic), 6.90 (s, 1H, aromatic), 0.96 (s, 3H, 18-$CH_3$); MS (EI): m/z 315 ($M^+$).

(b) Synthesis of 4-Nitroestra-1,3,5(10)-trien-17-one-3-O-sulfamate (77):

To a solution of chlorosulfonyl isocyanate (0.43 mL, 5.0 mmol) in $CH_2Cl_2$ (2.0 mL) was added formic acid (1.0 mL of a $CH_2Cl_2$ solution, 5.0 M, 5.0 mmol) at 0° C. The reaction mixture was warmed to room temperature and stirred for 1 h. To a solution of 3-hydroxy-4-nitroestra-1,3,5(10)-trien-17-one (76a, 0.315 g, 1.0 mmol) in DMF (5.0 mL) was added sodium hydride (0.200 g of a mineral oil dispersion, 60%, 5.0 mmol) at 0° C. The reaction mixture was stirred for 1 h, and the chlorosulfonyl isocyanate in formic acid was added, and stirring continued for 4 h at room temperature. The reaction mixture was quenched with saturated aqueous NH$_4$Cl at 0° C., and extracted with EtOAc. The combined organic layers were washed with H$_2$O, saturated aqueous NaCl, and then dried (Na$_2$SO$_4$). The desiccant was filtered and the solvent was evaporated at reduced pressure. The residue was purified by column chromatography (silica gel) using n-hexane:EtOAc (3:1→3:2, v/v) to afford 0.084 g of the starting material 76a (27% yield) and 0.243 g of 77 (62% yield) mp: 178–180° C.

$^1$H NMR: δ 7.49 (d, 1H, aromatic), 7.43 (d, 1H, aromatic), 5.22 (s, 2H, —NH$_2$), 0.92 (s, 3H, 18-CH$_3$); MS (EI): m/z 394 (M$^+$).

EXAMPLE 27

Preparation of 2-Nitroestra-1,3,5(10)-trien-17-one-3-O-sulfamate (78)

(a) Synthesis of 3-Hydroxy-4-nitroestra-1,3,5(10)-trien-17-one (76a) and 3-Hydroxy-2-nitroestra-1,3,5(10)-trien-17-one (76b):

The procedure described in step (a) of Example 26 above was used to obtain 76a and 76b from 11.

(b) Synthesis of 2-Nitroestra-1,3,5(10)-trien-17-one-3-O-sulfamate (78):

The procedure described in step (b) of Example 26 above was used to obtain 0.122 g of the starting material 76b (39% yield) and 0.165 g of 78 (42% yield; mp: 107–109° C.) from 3-hydroxy-2-nitroestra-1,3,5(10)-trien-17-one (76b, 0.315 g, 1.0 mmol) after chromatography (n-hexane:acetone 4:1→3:2, v/v).

$^1$H NMR: δ 7.76 (s, 1H, aromatic), 7.29 (s, 1H, aromatic), 5.43 (s, 2H, —NH$_2$), 0.91 (s, 3H, 18-CH$_3$); MS (DCI): m/z 412 (M$^+$+NH$_4^+$); HRMS calcd for C$_{18}$H$_{21}$N$_2$O$_6$S$_1$ 393.1120, found 393.1127.

EXAMPLE 28

Preparation of 2-Dimethylaminoestra-1,3,5(10)-trien-17-one-3-O-sulfamate (83)

(a) Synthesis of (76b):

The procedure in step (a) of Example 26 above was used to obtain 76b from 11.

(b) Synthesis of 3-Benzyloxy-2-nitroestra-1,3,5(10)-trien-17-one (79):

To a solution of 3-hydroxy-2-nitroestra-1,3,5(10)-trien-17-one (76b, 1.58 g, 5.0 mmol) in DMF (20 mL) were added potassium carbonate (1.38 g, 10 mmol) and benzyl bromide (0.9 mL, 7.5 mmol) and stirred for 19 h at room temperature. To the reaction mixture was added saturated aqueous NH$_4$Cl at 0° C. and extracted with CHCl$_3$. The combined organic layers were washed with H$_2$O, saturated aqueous NaCl, and then dried (Na$_2$SO$_4$). The desiccant was filtered and the solvent was evaporated at reduced pressure. The residue was washed with Et$_2$O to afford 2.01 g of 79 (99% yield) mp: 234–235° C.

$^1$H NMR: δ 7.83 (s, 1H, aromatic), 7.55–7.30 (m, 5H, aromatic), 6.83 (s, 1H, aromatic), 5.19 (s, 2H, —OCH$_2$-Ph), 0.91 (s, 3H, 18-CH$_3$).

(c) Synthesis of 3-Benzyloxy-2-aminoestra-1,3,5(10)-trien-17-one (80):

To a suspension of 3-benzyloxy-2-nitroestra-1,3,5(10)-trien-17-one (79, 1.82 g, 4.5 mmol) in acetone (250 mL) were added 0.5 N aqueous NaOH (60 mL, 30 mmol) and sodium hydrosulfite (85%, 6.0 g) at 80° C., and stirred for 1 h. After the reaction mixture was cooled to room temperature, H$_2$O (150 mL) was added, acetone was removed at reduced pressure, and the remainder allowed to stand for 3 h at 0° C. The precipitate was collected by filtration and washed with H$_2$O to afford 1.15 g of 80 (68% yield) mp: 205–207° C.

$^1$H NMR: δ 7.60–7.30 (m, 5H, aromatic), 6.70 (s, 1H, aromatic), 6.60 (s, 1H, aromatic), 5.05 (s, 2H, —OCH$_2$-Ph), 0.91 (s, 3H, 18-CH$_3$).

(d) Synthesis of 3-Benzyloxy-2-dimethylaminoestra-1,3,5 (10)-trien-17-one (81):

To a suspension of 3-benzyloxy-2-aminoestra-1,3,5(10)-trien-17-one (80, 0.751 g, 2.0 mmol) in THF (2.0 mL) and CH$_3$CN (10 mL) were added 37% aqueous formaldehyde (4.0 mL) and sodium cyanoborohydride (0.377 g, 6.0 mmol) and stirred for 2 h at room temperature. Additional sodium cyanoborohydride (0.377 g, 6.0 mmol) was then added to the reaction mixture, which mixture was then stirred for 20 h. Next, saturated aqueous NH$_4$Cl at 0° C., was added to the reaction mixture, and it was then extracted with EtOAc. The combined organic layers were washed with H$_2$O, saturated aqueous NaCl, and then dried (Na$_2$SO$_4$). The desiccant was filtered and the solvent was evaporated at reduced pressure. The residue was purified by column chromatography (silica gel) using n-hexane:THF (5:1→3:1, v/v) to afford 0.797 g of 81 (99% yield) mp: 165–166° C.

$^1$H NMR: δ 7.55–7.25 (m, 5H, aromatic), 6.89 (s, 1H, aromatic), 6.65 (s, 1H, aromatic), 5.12 (s, 2H, —OCH$_2$-Ph), 2.82 (s, 6H, —N(CH$_3$)$_2$), 0.92 (s, 3H, 18-CH$_3$).

(e) Synthesis of 2-Dimethylamino-3-hydroxyestra-1,3,5 (10)-trien-17-one (82):

To a solution of 3-benzyloxy-2-dimethylaminoestra-1,3, 5(10)-trien-17-one (81, 0.666 g, 1.65 mmol) in THF (30 mL) was added 10% palladium on carbon (0.200 g). The reaction mixture was stirred for 1 h under a hydrogen atmosphere at room temperature. After the catalyst was filtered, the solvent was evaporated at reduced pressure. The residue was purified by column chromatography (silica gel) using n-hexane:EtOAc (3:1→2:1, v/v) to afford 0.462 g of 82 (89% yield) mp: 160–161° C.

$^1$H NMR: δ 7.09 (s, 1H, aromatic), 6.68 (s, 1H, aromatic), 2.64 (s, 6H, —N(CH$_3$)$_2$), 0.92 (s, 3H, 18-CH$_3$); MS (EI): m/z 313 (M$^+$).

(f) Synthesis of 2-Dimethylaminoestra-1,3,5(10)-trien-17-one-3-O-sulfamate (83):

To a solution of chlorosulfonyl isocyanate (0.22 mL, 2.5 mmol) in CH$_2$Cl$_2$ (1.0 mL) was added formic acid (0.5 mL of a CH$_2$Cl$_2$ solution, 5.0 M, 2.5 mmol) at 0° C. The reaction mixture was warmed to room temperature and stirred for 1 h. To a solution of 2-dimethylamino-3-hydroxyestra-1,3,5 (10)-trien-17-one (82, 0.157 g, 0.5 mmol) in DMF (3.0 mL) was added sodium hydride (0.100 g of a mineral oil dispersion, 60%, 2.5 mmol) at 0° C. The reaction mixture was stirred for 1 h, the chlorosulfonyl isocyanate in formic acid was added, and stirring continued for 2 h. The reaction mixture was quenched with saturated aqueous NaHCO$_3$ at 0° C., and extracted with EtOAc. The combined organic layers were washed with H$_2$O, saturated aqueous NaCl, and then dried (Na$_2$SO$_4$). The desiccant was filtered and the solvent was evaporated at reduced pressure. The residue was purified by column chromatography (silica gel) using n-hexane:THF (3:1→2:1, v/v) to afford 0.082 g of the starting material 82 (52% yield) and 0.070 g of 83 (36% yield) mp: 178–179° C.

$^1$H NMR: δ 7.05 (s, 1H, aromatic), 7.02 (s, 1H, aromatic), 2.79 (s, 6H, —N(CH$_3$)$_2$), 0.92 (s, 3H, 18-CH$_3$); MS (EI): m/z 392 (M$^+$).

EXAMPLE 29

Preparation of 4-Dimethylaminoestra-1,3,5(10)-trien-17-one-3-O-sulfamate (88)

(a) Synthesis of (76a):

The procedure described in step (a) of Example 26 above was used to obtain 76a from 11.

(b) Synthesis of 3-Benzyloxy-4-nitroestra-1,3,5(10)-trien-17-one (84):

To a solution of 3-hydroxy4-nitroestra-1,3,5(10)-trien-17-one (76a, 3.15 g, 10 mmol) in DMF (40 mL) were added potassium carbonate (2.76 g, 20 mmol) and benzyl bromide (1.8 mL, 15 mmol); the mixture was then stirred for 1 h at room temperature.

Saturated aqueous $NH_4Cl$ at 0° C. was then added, and the mixture was extracted with $CHCl_3$. The combined organic layers were washed with $H_2O$, saturated aqueous NaCl, and then dried ($Na_2SO_4$). The desiccant was filtered and the solvent was evaporated at reduced pressure. The residue was washed with $Et_2O$ to afford 3.73 g of 84 (92% yield) mp: 198–199° C.

$^1$H NMR: δ 7.45–7.20 (m, 6H, aromatic), 6.87 (d, 1H, aromatic), 5.15 (s, 2H, —$OCH_2$-Ph), 0.92 (s, 3H, 18-$CH_3$).

(c) Synthesis of 3-Benzyloxy-4-aminoestra-1,3,5(10)-trien-17-one (85):

To a suspension of 3-benzyloxy4-nitroestra-1,3,5(10)-trien-17-one (84, 3.24 g, 8.0 mmol) in acetone (400 mL) were added 0.5 N aqueous NaOH (100 mL, 50 mmol) and sodium hydrosulfite (85%, 10 g) at 80° C.; the mixture was then stirred for 1 h. After the reaction mixture was cooled to room temperature, $H_2O$ (300 mL) was added; Acetone was then removed at reduced pressure, and the mixture allowed to stand for 3 h at 0° C. The precipitate was collected by filtration and washed with $H_2O$ to afford 2.29 g of 85 (76% yield) mp: 219–221° C.

$^1$H NMR: δ 7.50–7.30 (m, 5H, aromatic), 6.76 (d, 1H, aromatic), 6.71 (d, 1H, aromatic), 5.08 (s, 2H, —$OCH_2$-Ph), 0.90 (s, 3H, 18-$CH_3$).

(d) Synthesis of 3-Benzyloxy-4-dimethylaminoestra-1,3,5(10)-trien-17-one (86):

To a suspension of 3-benzyloxy-4-aminoestra-1,3,5(10)-trien-17-one (85, 0.188 g, 0.5 mmol) in THF (1.0 mL) and $CH_3CN$ (5.0 mL) were added 37% aqueous formaldehyde (1.0 mL) and sodium cyanoborohydride (0.251 g, 4.0 mmol); the mixture was then stirred for 3 h at room temperature. Additional sodium cyanoborohydride (0.251 g, 4.0 mmol) was then added, and the mixture stirred for 24 h. Saturated aqueous $NH_4Cl$ at 0° C. was added, and the mixture extracted with EtOAc. The combined organic layers were washed with $H_2O$, saturated aqueous NaCl, and then dried ($Na_2SO_4$). The desiccant was filtered and the solvent was evaporated at reduced pressure. The residue was purified by column chromatography (silica gel) using n-hexane:EtOAc (3:1→1:1, v/v) to afford 0.109 g of 86 (54% yield).

$^1$H NMR: δ 7.53–7.26 (m, 5H, aromatic), 7.07 (d, 1H, aromatic), 6.79 (d, 1H, aromatic), 5.07 (s, 2H, —$OCH_2$-Ph), 2.78 (s, 6H, —$N(CH_3)_2$), 0.90 (s, 3H, 18-$CH_3$)

(e) Synthesis of 4-Dimethylamino-3-hydroxyestra-1,3,5(10)-trien-17-one (87):

To a solution of 3-benzyloxy-4-dimethylaminoestra-1,3,5(10)-trien-17-one (86, 0.271 g, 0.67 mmol) in THF (10 mL) was added 10% palladium on carbon (0.200 g). The reaction mixture was stirred for 1 h under a hydrogen atmosphere at room temperature. After the catalyst was filtered, the solvent was evaporated at reduced pressure. The residue was purified by column chromatography (silica gel) using n-hexane:EtOAc (5:1→3:1, v/v) to afford 0.171 g of 87 (81% yield) mp: 155–156° C.

$^1$H NMR: δ 7.06 (d, 1H, aromatic), 6.78 (d, 1H, aromatic), 2.84 and 2.82 (s and s, each 3H, —$N(CH_3)_2$), 0.91 (s, 3H, 18-$CH_3$); MS (EI): m/z 313 (M$^+$).

(f) Synthesis of 4-Dimethylaminoestra-1,3,5(10)-trien-17-one-3-O-sulfamate (88):

To a solution of chlorosulfonyl isocyanate (0.16 mL, 1.8 mmol) in $CH_2Cl_2$ (0.7 mL) was added formic acid (0.36 mL of a $CH_2Cl_2$ solution, 5.0 M, 1.8 mmol) at 0° C. The reaction mixture was warmed to room temperature and stirred for 1 h. To a solution of 4-dimethylamino-3-hydroxyestra-1,3,5(10)-trien-17-one (87, 0.112 g, 0.36 mmol) in DMF (2.0 mL) was added sodium hydride (0.070 g of a mineral oil dispersion, 60%, 1.7 mmol) at 0° C. The reaction mixture was stirred for 1 h, the chlorosulfonyl isocyanate in formic acid was then added, and stirring continued for 2 h. The reaction mixture was quenched with saturated aqueous $NaHCO_3$ at 0° C., and extracted with EtOAc. The combined organic layers were washed with $H_2O$, saturated aqueous NaCl, and then dried ($Na_2SO_4$). The desiccant was filtered and the solvent was evaporated at reduced pressure. The residue was purified by column chromatography (silica gel) using n-hexane:EtOAc (3:1→3:2, v/v) to afford 0.069 g of the starting material 87 (61% yield) and 0.034 g of 88 (24% yield) mp: 151–152° C.

$^1$H NMR: δ 7.20 (d, 1H, aromatic), 7.09 (d, 1H, aromatic), 5.20–4.90 (br s, 2H, —$NH_2$), 2.84 (s, 6H, —$N(CH_3)2$), 0.92 (s, 3H, 18-$CH_3$); MS (EI): m/z 392 (M$^+$)

EXAMPLE 30

Preparation of 2-Acetoamideestra-1,3,5(10)-trien-17-one-3-O-sulfamate (93)

(a) Synthesis of (76b):

The procedure described in step (a) of Example 26 above was used to obtain 76b from 11.

(b) Synthesis of 3-tert-Butyldimethylsilyloxy-2-nitroestra-1,3,5(10)-trien-17-one (89):

To a solution of 3-hydroxy-2-nitroestra-1,3,5(10)-trien-17-one (76b, 1.10 g, 3.5 mmol) in DMF (10 mL) were added imidazole (0.476 g, 7.0 mmol) and tert-butyldimethylchlorosilane (0.690 g, 4.6 mmol) at room temperature. The reaction mixture was stirred for 1 h, and diluted with EtOAc, and washed with $H_2O$, saturated aqueous NaCl, and then dried ($Na_2SO_4$). The desiccant was filtered and the solvent was evaporated at reduced pressure. The residue was purified by column chromatography (silica gel) using n-hexane:EtOAc (5:1→2:1, v/v) to afford 1.45 g of 89 (97% yield) mp: 184–185° C.

$^1$H NMR: δ 7.76 (s, 1H, aromatic), 6.68 (s, 1H, aromatic), 1.01 (s, 9H, —$C(CH_3)_3$), 0.92 (s, 3H, 18-$CH_3$), 0.24 (s, 6H, —$Si(CH_3)_2$).

(c) Synthesis of 2-Amino-3-tert-butyldimethylsilyloxyestra-1,3,5(10)-trien-17-one (90):

To a solution of 3-tert-butyldimethylsilyloxy-2-nitroestra-1,3,5(10)-trien-17-one (89, 1.29 g, 3.0 mmol) in THF (30 mL) was added 10% palladium on carbon (0.200 g). The reaction mixture was stirred for 18 h under a hydrogen atmosphere at room temperature. After the catalyst was filtered, the solvent was evaporated at reduced pressure. The residue was purified by column chromatography (silica gel) using n-hexane:EtOAc (5:1→3:1, v/v) to afford 1.08 g of 90 (87% yield) mp: 173–174° C.

$^1$H NMR: δ 6.66 (s, 1H, aromatic), 6.45 (s, 1H, aromatic), 1.01 (s, 9H, —$C(CH_3)_3$), 0.90 (s, 3H, 18-$CH_3$), 0.24 (s, 6H, —$Si(CH_3)_2$).

(d) Synthesis of 2-Acetoamide-3-tert-butyldimethylsilyloxyestra-1,3,5(10)-trien-17-one (91):

To a solution of 2-amino-3-tert-butyldimethylsilyloxyestra-1,3,5(10)-trien-17-one (90, 0.416 g, 1.0 mmol) in $CH_2Cl_2$ (5.0 mL) were added triethylamine (0.34 ml, 2.5 mmol) and acetic anhydride (0.14 mL, 1.5 mmol), and stirred for 4 h at room temperature. Saturated aqueous $NaHCO_3$ were next added to the reaction mixture, which mixture was then extracted with EtOAc. The combined organic layers were washed with $H_2O$, saturated aqueous NaCl, and then dried ($Na_2SO_4$). The desiccant was filtered and the solvent was evaporated at reduced pressure. The residue was purified by column chromatography (silica gel) using n-hexane:EtOAc (5:1→3:1, v/v) to afford 0.354 g of 91 (80% yield).

$^1$H NMR: δ 8.24 (s, 1H, aromatic), 7.55 (s, 1H, —NHCOCH$_3$), 6.52 (s, 1H, aromatic), 2.15 (s, 3H, —NHCOC$\underline{H}_3$), 1.03 (s, 9H, —C(CH$_3$)$_3$), 0.90 (s, 3H, 18-CH$_3$), 0.25 (s, 6H, —Si(CH$_3$)$_2$).

(e) Synthesis of 2-Acetoamide-3-hydroxyestra-1,3,5(10)-trien-17-one (92):

To a solution of 2-acetoamide-3-tert-butyldimethylsilyloxyestra-1,3,5(10)-trien-17-one (91, 0.339 g, 0.77 mmol) in THF (5.0 mL) was added tetrabutylammonium fluoride (0.80 mL of a THF solution, 1.0 M, 0.80 mmol) at 0° C. The reaction mixture was stirred for 10 min, diluted with EtOAc, washed with H$_2$O, saturated aqueous NaCl, and then dried (Na$_2$SO$_4$). The desiccant was filtered and the solvent was evaporated at reduced pressure. The residue was washed with Et$_2$O to afford 0.228 g of 92 (91% yield) mp: >250° C.

$^1$H NMR: δ 8.62 (s, 1H, aromatic), 7.53 (s, 1H, —N$\underline{H}$COCH$_3$), 6.86 (s, 1H, —OH), 6.76 (s, 1H, aromatic), 2.25 (s, 3H, —NHCOC$\underline{H}_3$), 0.91 (s, 3H, 18-CH$_3$); MS (EI): m/z 327 (M$^+$).

(f) Synthesis of 2-Acetoamideestra-1,3,5(10)-trien-17-one-3-O-sulfamate (93):

To a solution of chlorosulfonyl isocyanate (0.22 mL, 2.5 mmol) in CH$_2$Cl$_2$ (1.0 mL) was added formic acid (0.5 mL of a CH$_2$Cl$_2$ solution, 5.0 M, 2.5 mmol) at 0° C. The reaction mixture was warmed to room temperature and stirred for 1 h. To a solution of 3-hydroxy-2-acetoamideestra-1,3,5(10)-trien-17-one (92, 0.163 g, 0.5-mmol) in DMF (3.0 mL) was added sodium hydride (0.100 g of a mineral oil dispersion, 60%, 2.5 mmol) at 0° C. The reaction mixture was stirred for 1 h, the chlorosulfonyl isocyanate in formic acid was then added, and stirring continued for 3 h. The reaction mixture was quenched with saturated aqueous NH$_4$Cl at 0° C., and extracted with EtOAc. The combined organic layers were washed with H$_2$O, saturated aqueous NaCl, and then dried (Na$_2$SO$_4$). The desiccant was filtered and the solvent was evaporated at reduced pressure. The residue was purified by column chromatography (silica gel) using CHCl$_3$:THF (5:1→2:1, v/v) to afford 0.130 g of 93 (64% yield) mp: 180–182° C.

$^1$H NMR: δ 7.93 (s, 1H, —N$\underline{H}$COCH$_3$), 7.74 (s, 1H, aromatic), 7.12 (s, 1H, aromatic), 5.61 (s, 2H, —NH$_2$), 2.16 (s, 3H, —NHCOC$\underline{H}_3$), 0.89 (s, 3H, 18-CH$_3$); MS (DCI): m/z 407 (M$^+$+H).

EXAMPLE 31

Preparation of 4-Acetoamideestra-1,3,5(10)-trien-17-one-3-O-sulfamate (96)

(a) Synthesis of 4-Amino-3-benzyloxyestra-1,3,5(10)-trien-17-one (85):

The procedure described in step (a) of Example 26 above was used to obtain 76b from 11.

(b) Synthesis of 3-Benzyloxy-4-aminoestra-1,3,5(10)-trien-17-one (85):

The procedure described in steps (b) and (c) of Example 29 above was used to obtain 85 from 76b.

(c) Synthesis of 4-Acetoamide-3-benzyloxyestra-1,3,5(10)-trien-17-one (94): To a suspension of 4-amino-3-benzyloxyestra-1,3,5(10)-trien-17-one (85, 0.376 g, 1.0 mmol) in CH$_2$Cl$_2$ (5.0 mL) and THF (2.0 mL) were added triethylamine (0.34 ml, 2.5 mmol) and acetic anhydride (0.14 mL, 1.5 mmol); the mixture was then stirred for 20 h at room temperature. Saturated aqueous NaHCO$_3$ was then added to the reaction mixture, which mixture was then extracted with EtOAc. The combined organic layers were washed with H$_2$O, saturated aqueous NaCl, and then dried (Na$_2$SO$_4$). The desiccant was filtered and the solvent was evaporated at reduced pressure. The residue was washed with Et$_2$O to afford 0.338 g of 94 (81% yield) mp: 212–213° C.

$^1$H NMR: δ 7.47–7.30 (m, 5H, aromatic), 7.18 (d, 1H, aromatic), 6.82 (d, 1H, aromatic), 6.75 (s, 1H, —N$\underline{H}$COCH$_3$), 5.06 (s, 2H, —OCH$_2$Ph), 2.17 (s, 3H, —NHCOC$\underline{H}_3$), 0.90 (s, 3H, 18-CH$_3$).

(d) Synthesis of 4-Acetoamide-3-hydroxyestra-1,3,5(10)-trien-17-one (95):

To a solution of 4-acetoamide-3-benzyloxyestra-1,3,5 (10)-trien-17-one (94, 0.313 g, 0.75 mmol) in THF (10 mL) was added 10% palladium on carbon (0.100 g). The reaction mixture was stirred for 3 h under a hydrogen atmosphere at room temperature. After the catalyst was filtered, the solvent was evaporated at reduced pressure. The residue was purified by column chromatography (silica gel) using n-hexane:acetone (2:1→3:2, v/v) to afford 0.250 g of 95 (100% yield) mp: 158–159° C.

$^1$H NMR: δ 7.17 (d, 1H, aromatic), 7.08 (s, 1H, —N$\underline{H}$COCH$_3$), 6.91 (d, 1H, aromatic), 2.31 (s, 3H, —NHCOC$\underline{H}_3$), 0.90 (s, 3H, 18-CH$_3$); MS (EI): m/z 327 (M$^+$).

(e) Synthesis of 4-Acetoamideestra-1,3,5(10)-trien-17-one-3-O-sulfamate (96):

To a solution of chlorosulfonyl isocyanate (0.22 mL, 2.5 mmol) in CH$_2$Cl$_2$ (1.0 mL) was added formic acid (0.5 mL of a CH$_2$Cl$_2$ solution, 5.0 M, 2.5 mmol) at 0° C. The reaction mixture was warmed to room temperature and stirred for 1 h. To a solution of 3-hydroxy-4-acetoamideestra-1,3,5(10)-trien-17-one (95, 0.152 g, 0.46 mmol) in DMF (3.0 mL) was added sodium hydride (0.100 g of a mineral oil dispersion, 60%, 2.5 mmol) at 0° C. The reaction mixture was stirred for 1 h, the chlorosulfonyl isocyanate in formic acid was added, and stirring continued for 3 h. The reaction mixture was quenched with saturated aqueous NH$_4$Cl at 0° C., and extracted with EtOAc. The combined organic layers were washed with H$_2$O, saturated aqueous NaCl, and then dried (Na$_2$SO$_4$). The desiccant was filtered and the solvent was evaporated at reduced pressure. The residue was purified by column chromatography (silica gel) using n-hexane:acetone (3:1→3:2, v/v) to afford 0.040 g of the starting material 95 (27% yield) and 0.087 g of 96 (47% yield) mp: 176–178° C.

$^1$H NMR (CDCl$_3$-DMSO-d6): d 8.14 (d, 1H, aromatic), 7.32 (d, 1H, aromatic), 6.59 (s, 2H, —NH$_2$), 2.21 (s, 3H, —NHCOC$\underline{H}_3$), 0.90 (s, 3H, 18-CH$_3$); MS (DCI): m/z 424 (M$^+$+NH$_4^+$), 407 (M$^+$+H).

EXAMPLE 32

Preparation of β-Homo-9-(10→19)-abeoestra-1,3,5 (10),9(19)-tetraen-11,17-dione-3-O-sulfamate (99)

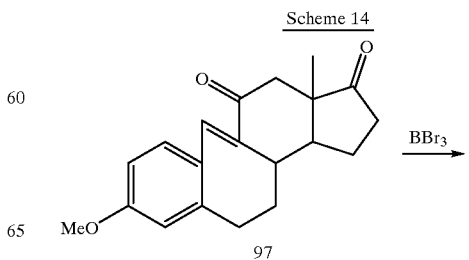

Scheme 14

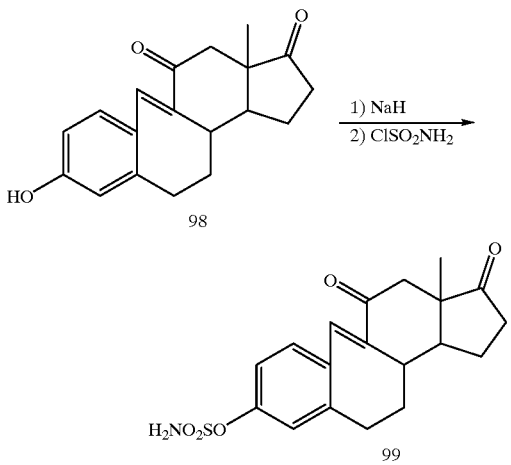

(a) Synthesis of 3-Hydroxy-β-homo-9-(10→19)-abeoestra-1,3,5(10),9(19)-tetraen-11,17-dione (98):

To a solution of 3-methoxy-β-homo-9-(10–19)-abeoestra-1,3,5(10),9(19)-tetraen-11,17-dione (97, 0.931 g, 3.0 mmol) in $CH_2Cl_2$ (35 mL) was added boron tribromide (15 mL of a $CH_2Cl_2$ solution, 1.0 M, 15 mmol) at 0° C. After stirring for 3 h, additional boron tribromide (5.0 mL of a $CH_2Cl_2$ solution, 1.0 M, 5.0 mmol) was added. The reaction mixture was stirred for an additional 1 h, then quenched with $H_2O$, and then extracted with EtOAc. The combined organic layers were washed with $H_2O$, saturated aqueous NaCl, and then dried ($Na_2SO_4$). The desiccant was filtered and the solvent was evaporated at reduced pressure. The residue was purified by column chromatography (silica gel) using $CHCl_3$:EtOAc (5:1, v/v) to afford 0.552 g of 98 (62% yield) mp: 225–226° C.

$^1$H NMR: δ 7.56–7.20 (m, 2H, aromatic), 6.80–6.70 (m, 2H, aromatic), 5.53 (s, 1H, —OH), 0.99 (s, 3H, 18-$CH_3$); MS (EI): m/z 296 ($M^+$).

(b) Synthesis of β-Homo-9-(10-19)-abeoestra-1,3,5(10),9(19)-tetraen-11,17-dione-3-O-sulfamate (99):

To a solution of chlorosulfonyl isocyanate (2.6 mL, 30 mmol) in $CH_2Cl_2$ (15 mL) was added formic acid (6.0 mL of a $CH_2Cl_2$ solution, 5.0 M, 30 mmol) at 0° C. The reaction mixture was warmed to room temperature and stirred for 1 h. To a solution of 3-hydroxy-β-homo-9-(10-19)-abeoestra-1,3,5(10),9(19)-tetraen-11,17-dione (98, 1.78 g, 6.0 mmol) in DMF (40 mL) was added sodium hydride (0.840 g of a mineral oil dispersion, 60%, 21 mmol) at 0° C. The reaction mixture was stirred for 1 h, then the chlorosulfonyl isocyanate in formic acid was added, and stirring continued for 2 h. The reaction mixture was quenched with saturated aqueous $NH_4Cl$ at 0° C., and extracted with EtOAc. The combined organic layers were washed with $H_2O$, saturated aqueous NaCl, and then dried ($MgSO_4$). The desiccant was filtered and the solvent was evaporated at reduced pressure. The residue was purified by column chromatography (silica gel) using $CHCl_3$:MeOH (30:1→15:1, v/v) to afford 1.68 g of 99 (75% yield) mp: 191–192° C.

$^1$H NMR ($CDCl_3$-DMSO-d6): d 7.44–7.12 (m, 4H, aromatic), 6.94 (s, 2H, —$NH_2$), 0.88 (s, 3H, 18-$CH_3$); MS (NES): m/z 374 ($M^+$–H); HRMS calcd. for $C_{19}H_{20}N_1O_5S_1$, 374.1062; found, 374.1049.

EXAMPLE 33

Biological Evaluation: Procedures and Results

A. Effects of Inhibitors on Estrone Sulfatase Activity in MCF-7 Cells

Reagents: MCF-7 human breast cancer cell line was supplied by the American Type Culture Collection, Rockville, MD. Eagle's minimum essential medium (MEM) and fetal calf serum (FCS) were purchased from Sigma Chemical Company, St. Louis, Mo. [4-$^{14}$C]Estrone, [6,7-$^3$H]estradiol and [6,7-$^3$H](N)estrone sulfate were obtained from New England Nuclear Research Products, Boston, Mass.

Procedure: The method of Duncan et al., Cancer Res. 53:298–303 (1993) was employed. MCF-7 cells were seeded in 60 mm×15 mm culture dishes at 1×10$^5$ cells/dish and maintained in 4.0 ml of MEM containing 2 mM glutamine and 5% FCS. The cells were incubated at 37° C. in an atmosphere of 5% $CO_2$/95% air and 100% humidity, with the medium changed every third day. When the cells reached 80% confluency, the intact monolayers were washed once with Earl's balanced salt solution and incubated in 4.0 ml of serum and phenol re-free MEM containing either the substrate ($^3$H-estrone sulfate, 7 pmol, 9×10$^5$ dpm) and inhibitor dissolved in ethanol, or ethanol alone. The fmal ethanol concentration was always below 1%. The incubation continued under the regular conditions for 24 h. At the end of 24 h, 2.0 ml of medium was transferred into separate tubes containing 7×10$^3$ dpm of $^{14}$C-estrone. The mixture was vortexed vigorously for 60 s with 5 ml of toluene. After phase separation, 2.0 ml of the organic phase was transferred into a counting vial for scintillation counting. The amount of estrone sulfate hydrolyzed was calculated on the basis of $^3$H counts obtained, with the added $^{14}$C-estrone counts used to correct for recovery through the extraction procedure.

The cells remaining in each culture dish were washed once with saline and then scraped with 1.0 ml of 0.5 N NaOH into 10×75 mm tubes. The cell pellets in each tube was incubated at 50° C. for 20 min to ensure that digestion was complete and all proteins had became soluble. An aliquot was then taken for protein determination by Lowry's method (Lowry et al., J. Biol. Chem. 193:265–275 (1951)).

The percentage of inhibition was determined by evaluating the quantity of estrone sulfate hydrolyzed with the inhibitor relative to that without the inhibitor.

As a general practice, all available inhibitors were first tested at 100 μM; the ones showing inhibitory effects at that concentration were tested again at various concentrations to obtain the $IC_{50}$ values.

B. Uterotrophic and antiuterotrophic assays

Sprague Dawley rates are obtained from Simmonsen Laboratories, Gilroy, Calif. Estradiol benzoate may be purchased from Sigma Chemical Co., St. Louis, Mo.

The procedure of Wakeling et al., Endocrinology 99:447453 (1983) is followed. Female Sprague Dawley rats weighing 40–50 grams are used for the experiment. In general, animals are quarantined for 3 days after arrival at the experimental site.

Rats are initially weighed and randomly divided into groups with 5 animals in each group. For the uterotrophic assay, animals are dosed once daily with various doses of test compounds in 0.1 or 1.0 ml of sterile saline via subcutaneous injection or oral gavage, respectively. For the antiuterotrophic assay, animals are dosed once daily with the same doses indicated above plus 0.5 μg/rat of estradiol benzoate alone.

The animals are treated for 7 days. On day 8, animals are weighed and then sacrificed. The uterus of each animal is removed immediately after death and weighed; fat materials are trimmed off prior to weighing.

A comparison of uterine weights from the groups receiving test compound alone with those of the vehicle control group gives the estrogenic activity. Antiestrogenic activity is obtained by comparing the uterine weights from the groups receiving test compound plus estradiol with those of the estradiol control group.

The results of the biological testing procedures used to evaluate the compounds of the invention are set forth in the following table:

| Compound Number | Estrone Sulfatase Inhibitory Activity IC$_{50}$ | Estrogenic Activity |
|---|---|---|
| 5 | 250 pM | 0.40 |
| 7 | 21 pM | 0.66 |
| 10 | 2 nM | 0 |
| 13 | 80 pM | 0.05 |
| 15 | 38 pM | 0.30 |
| 17 | 11 pM | 0.55 |
| 19 | 20 pM | 0.54 |
| 21 | 34 pM | 0 |
| 23 | 96 pM | 0.02 |
| 28 | 27 pM | 0.20 |
| 32 | 2.7 nM | 0 |
| 34 | 270 pM | 0 |
| 36 | 90 pM | 0.44 |
| 39 | 34 nM | 0 |
| 44 | 24 nM | 0 |
| 47 | 23 nM | 0.27 |
| 52 | 310 pM | 0 |
| 55 | 26 nM | 0 |
| 59 | 300 pM | 0 |
| 65 | >1 nM | 0 |
| 67 | 16 pM | 0 |
| 69 | 2.5 nM | 0 |
| 71 | 1.5 nM | 0 |
| 73 | >1 μM | 0 |
| 75 | 2 nM | 0 |
| 77 | <10 nM | 0 |
| 78 | 7 nM | 0 |
| 83 | 270 nM | 0 |
| 88 | 515 nM | 0 |
| 93 | 410 nM | 0.02 |
| 96 | 290 nM | 0 |
| 99 | 26 nM | 0 |

We claim:

1. A compound having the structural formula

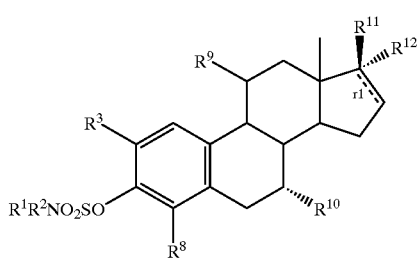

(I)

wherein:
r1 is an optional double bond;
R$^1$ and R$^2$ are selected from the group consisting of hydrogen and lower alkyl, or together form a cyclic substituent (II)

(II)

wherein Q is NH, O or CH$_2$;
R$^3$ is selected from the group consisting of hydrogen, —CN, —NO$_2$, —COOR$^4$ wherein R$^4$ is hydrogen or lower alkyl, —(CH$_2$)$_n$OR$^5$ and —(CH$_2$)$_n$NR$^6$R$^7$ wherein n is 0 to 6, R$^5$ is hydrogen or lower alkyl, and R$^6$ and R$^7$ are selected from the group consisting of hydrogen, lower alkyl and lower acyl, or together form the cyclic substituent (II);

R$^8$ is selected from the group consisting of hydrogen, —NO$_2$, and NR$^6$R$^7$;

R$^9$ and R$^{10}$ are independently selected from the group consisting of hydrogen and lower alkyl;

when r1 is present, one of R$^{11}$ and R$^{12}$ is not present and the other is hydrogen, lower alkyl, lower alkenyl, lower alkynyl, lower alkoxy, lower acyl, lower acyloxy, or —(CH$_2$)$_m$—O—(CH$_2$)$_q$—NR$^6$R$^7$ wherein m and q are integers in the range of 0 to 6 and 1 to 6, respectively; and when r1 is not present, one of R$^{11}$ and R$^{12}$ is hydrogen and the other is lower alkyl, lower alkenyl, lower alkynyl, lower alkoxy, lower acyl, lower acyloxy, or —(CH$_2$)$_m$—O—(CH$_2$)$_q$—NR$^6$R$^7$ wherein m and q are integers in the range of 0 to 6 and 1 to 6, respectively, or R$^{11}$ and R$^{12}$ together form =O or =CR$^{13}$R$^{14}$ in which R$^{13}$ and R$^{14}$ are independently selected from the group consisting of hydrogen, lower alkyl, —CN, —(CH$_2$)$_m$—O—(CH$_2$)$_q$—NR$^6$R$^7$ and —COOR$^4$, with the provisos that
(a) when R$^{11}$ and R$^{12}$ together form =O, then at least one of R$^3$, R$^8$, R$^9$ and R$^{10}$ is other than hydrogen, providing that if R$^3$ is —(CH$_2$)$_n$—OR$^5$ and R$^5$ is lower alkyl, then n is other than 0, and (b) when one of R$^{11}$ and R$^{12}$ is lower acyloxy and the other is hydrogen, then R$^1$ and R$^2$ are other than lower alkyl; and pharmaceutically acceptable salts and esters thereof.

2. The compound of claim 1 wherein R$^1$, R$^2$, R$^9$ and R$^{10}$ are hydrogen, and the optional double bond r1 is not present.

3. The compound of claim 2 wherein R$^{11}$ and R$^{12}$ together form =O.

4. The compound of claim 2 wherein R$^{11}$ and R$^{12}$ together form =CR$^{13}$R$^{14}$ in which one of R$^{13}$ and R$^{14}$ is hydrogen, or R$^{13}$ and R$^{14}$ are both —CN.

5. The compound of claim 2 wherein one of R$^{11}$ and R$^{12}$ is hydrogen and the other is —(CH$_2$)$_m$—O(CH$_2$)$_q$—N(CH$_3$)$_2$, m is 0 or 1, and q is 2, 3 or 4.

6. A method for inhibiting the enzymatic activity of estrone sulfatase comprising contacting the enzyme with an effective estrone sulfatase inhibiting amount of a compound having the structural formula (I)

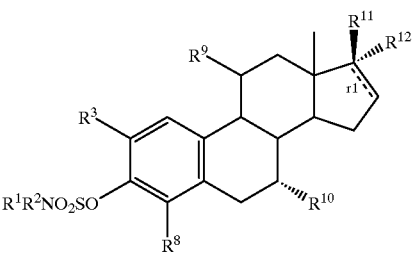

(I)

wherein:
r1 is an optional double bond;
R$^1$ and R$^2$ are selected from the group consisting of hydrogen and lower alkyl, or together form a cyclic substituent (II)

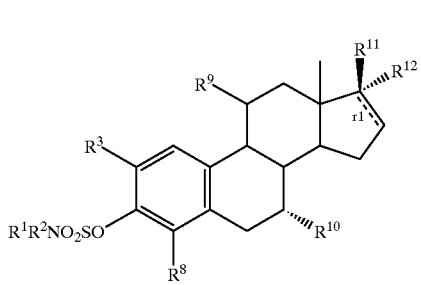
(I)

wherein:
r1 is an optional double bond;
$R^1$ and $R^2$ are selected from the group consisting of hydrogen and lower alkyl, or together form a cyclic substituent (II)

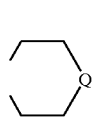
(II)

wherein Q is NH, O or $CH_2$;

$R^3$ is selected from the group consisting of hydrogen, —CN, —$NO_2$, —$COOR^4$ wherein $R^4$ is hydrogen or lower alkyl, —$(CH_2)_nOR^5$ and —$(CH_2)_nNR^6R^7$ wherein n is 0 to 6, $R^5$ is hydrogen or lower alkyl, and $R^6$ and $R^7$ are selected from the group consisting of hydrogen, lower alkyl and lower acyl, or together form the cyclic substituent (II);

$R^8$ is selected from the group consisting of hydrogen, —$NO_2$, and $NR^6R^7$;

$R^9$ and $R^{10}$ are independently selected from the group consisting of hydrogen and lower alkyl;

when r1 is present, one of $R^{11}$ and $R^{12}$ is not present and the other is hydrogen, lower alkyl, lower alkenyl, lower alkynyl, lower alkoxy, lower acyl, lower acyloxy, or —$(CH_2)_m$—O—$(CH_2)_q$—$NR^6R^7$ wherein m and q are integers in the range of 0 to 6 and 1 to 6, respectively; and when r1 is not present, one of $R^{11}$ and $R^{12}$ is hydrogen and the other is lower alkyl, lower alkenyl, lower alkynyl, lower alkoxy, lower acyl, lower acyloxy, or —$(CH_2)_m$—O—$(CH_2)_q$—$NR^6R^7$ wherein m and q are integers in the range of 0 to 6 and 1 to 6, respectively, or $R^{11}$ and $R^{12}$ together form =O or =$CR^{13}R^{14}$ in which $R^{13}$ and $R^{14}$ are independently selected from the group consisting of hydrogen, lower alkyl, —CN, —$(CH_2)_m$—O—$(CH_2)_q$—$NR^6R^7$ and —$COOR^4$, with the provisos that (a) when $R^{11}$ and $R^{12}$ together form =O, then at least one of $R^3$, $R^8$, $R^9$ and $R^{10}$ is other than hydrogen, providing that if $R^3$ is —$(CH_2)_n$—$OR^5$ and $R^5$ is lower alkyl, then n is other than 0, and (b) when one of $R^{11}$ and $R^{12}$ is lower acyloxy and the other is hydrogen, then $R^1$ and $R^2$ are other than lower alkyl; or a pharmaceutically acceptable salt or ester thereof.

7. The method of claim 6 wherein, in the compound of formula (I), $R^1$, $R^2$, $R^9$ and $R^{10}$ are hydrogen, and the optional double bond r1 is not present.

8. The method of claim 7 wherein, in the compound of formula (I), $R^{11}$ and $R^{12}$ together form =O.

9. The method of claim 7 wherein, in the compound of formula (I), $R^{11}$ and $R^{12}$ together form =$CR^{13}R^{14}$ in which one of $R^{13}$ and $R^{14}$ is hydrogen, or $R^{13}$ and $R^{14}$ are both —CN.

10. The method of claim 7 wherein, in the compound of formula I, $R^{11}$ and $R^{12}$ is hydrogen and the other is —$(CH_2)_m$—$O(CH_2)_q$—$N(CH_3)_2$, m is 0 or 1, and q is 2, 3 or 4.

11. A method for treating an individual with an estrogen-dependent disorder, comprising administering to the individual a pharmacologically effective amount of a compound of structural formula (I)

(II)

wherein Q is NH, O or $CH_2$;

$R^3$ is selected from the group consisting of hydrogen, —CN, —$NO_2$, —$COOR^4$ wherein $R^4$ is hydrogen or lower alkyl, —$(CH_2)_nOR^5$ and —$(CH_2)_nNR^6R^7$ wherein n is 0 to 6, $R^5$ is hydrogen or lower alkyl, and $R^6$ and $R^7$ are selected from the group consisting of hydrogen, lower alkyl and lower acyl, or together form the cyclic substituent (II);

$R^8$ is selected from the group consisting of hydrogen, —$NO_2$, and $NR^6R^7$;

$R^9$ and $R^{10}$ are independently selected from the group consisting of hydrogen and lower alkyl;

when r1 is present, one of $R^{11}$ and $R^{12}$ is not present and the other is hydrogen, lower alkyl, lower alkenyl, lower alkynyl, lower alkoxy, lower acyl, lower acyloxy, or —$(CH_2)_m$—O—$(CH_2)_q$—$NR^6R^7$ wherein m and q are integers in the range of 0 to 6 and 1 to 6, respectively; and when r1 is not present, one of $R^{11}$ and $R^{12}$ is hydrogen and the other is lower alkyl, lower alkenyl, lower alkynyl, lower alkoxy, lower acyl, lower acyloxy, or —$(CH_2)_m$—O—$(CH_2)_q$—$NR^6R^7$ wherein m and q are integers in the range of 0 to 6 and 1 to 6, respectively, or $R^{11}$ and $R^{12}$ together form =O or =$CR^{13}R^{14}$ in which $R^{13}$ and $R^{14}$ are independently selected from the group consisting of hydrogen, lower alkyl, —CN, —$(CH_2)_m$—O—$(CH_2)_q$—$NR^6R^7$ and —$COOR^4$, with the provisos that (a) when $R^{11}$ and $R^{12}$ together form =O, then at least one of $R^3$, $R^8$, $R^9$ and $R^{10}$ is other than hydrogen, providing that if $R^3$ is —$(CH_2)_n$—$OR^5$ and $R^5$ is lower alkyl, then n is other than 0, and (b) when one of $R^{11}$ and $R^{12}$ is lower acyloxy and the other is hydrogen, then $R^1$ and $R^2$ are other than lower alkyl; or a pharmaceutically acceptable salt or ester thereof.

12. The method of claim 11 wherein, in the compound of formula (I), $R^1$, $R^2$, $R^9$ and $R^{10}$ are hydrogen, and the optional double bond r1 is not present.

13. The method of claim 12 wherein, in the compound of formula (I), $R^{11}$ and $R^{12}$ together form =O.

14. The method of claim 12 wherein, in the compound of formula (I), one of $R^{13}$ and $R^{14}$ is hydrogen, or $R^{13}$ and $R^{14}$ are both —CN.

15. The method of claim 12 wherein, in the compound of formula (I), one of $R^{11}$ and $R^{12}$ is hydrogen and the other is —(CH$_2$)$_m$—O(CH$_2$)$_q$—N(CH$_3$)$_2$, m is 0 or 1, and q is 2, 3 or 4.

16. A pharmaceutical composition comprising an effective estrone sulfatase inhibiting amount of the compound of claim 1 in combination with a pharmaceutically acceptable carrier.

17. A pharmaceutical composition comprising an effective estrone sulfatase inhibiting amount of the compound of claim 2 in combination with a pharmaceutically acceptable carrier.

18. A pharmaceutical composition comprising an effective estrone sulfatase inhibiting amount of the compound of claim 3 in combination with a pharmaceutically acceptable carrier.

19. A pharmaceutical composition comprising an effective estrone sulfatase inhibiting amount of the compound of claim 4 in combination with a pharmaceutically acceptable carrier.

20. A pharmaceutical composition comprising an effective estrone sulfatase inhibiting amount of the compound of claim 5 in combination with a pharmaceutically acceptable carrier.

21. The compound of claim 1, wherein $R^1$ and $R^2$ together form the cyclic substituent (II).

22. The compound of claim 1, wherein $R^1$ and $R^2$ are both hydrogen.

23. The compound of claim 1, wherein $R^1$ and $R^2$ are both lower alkyl.

24. The compound of claim 1, wherein $R^3$, $R^8$ and $R^9$ are hydrogen and $R^{10}$ is lower alkyl.

25. The compound of claim 1, wherein r1 is present.

26. The compound of claim 1, wherein r1 is absent.

27. The compound of claim 26, wherein one of $R^{11}$ and $R^{12}$ is hydrogen and the other is lower alkyl, lower alkenyl, lower alkynyl, lower alkoxy, lower acyl, lower acyloxy, or —(CH$_2$)$_m$—O—(CH$_2$)$_q$—NR$^6$R$^7$ wherein m and q are integers in the range of 0 to 6 and 1 to 6, respectively.

28. The compound of claim 26, wherein $R^{11}$ and $R^{12}$ together form =O.

29. The compound of claim 26, wherein $R^{11}$ and $R^{12}$ together form =CR$^{13}$R$^{14}$ in which $R^{13}$ and $R^{14}$ are independently selected from the group consisting of hydrogen, lower alkyl, —CN, —(CH$_2$)$_m$—O—(CH$_2$)$_q$—NR$^6$R$^7$ and —COOR$^4$.

30. A compound having the structural formula (III)

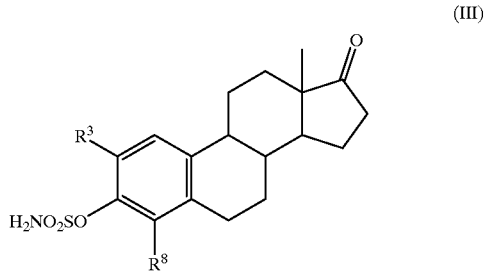

(III)

wherein:
$R^3$ is selected from the group consisting of hydrogen, —CN, —NO$_2$, —COOR$^4$ wherein $R^4$ is hydrogen or lower alkyl, —(CH$_2$)$_n$OR$^5$ and —(CH$_2$)$_n$NR$^6$R$^7$ wherein n is 0 to 6, $R^5$ is hydrogen or lower alkyl, and $R^6$ and $R^7$ are selected from the group consisting of hydrogen, lower alkyl and lower acyl, or together form the cyclic substituent (II)

(II)

wherein Q is NH, O or CH$_2$; and
$R^8$ is selected from the group consisting of hydrogen, —NO$_2$, and NR$^6$R$^7$, with the proviso that $R^3$ and $R^8$ are not both hydrogen, and with the further proviso that if $R^3$ is —(CH$_2$)$_n$—OR$^5$ and $R^5$ is lower alkyl, then n is other than 0.

31. The compound of claim 30, wherein $R^3$ is hydrogen and $R^8$ is —NO$_2$.

32. The compound of claim 30, wherein $R^3$ is hydrogen and $R^8$ is NR$^6$R$^7$.

33. A compound having the structural formula (IV)

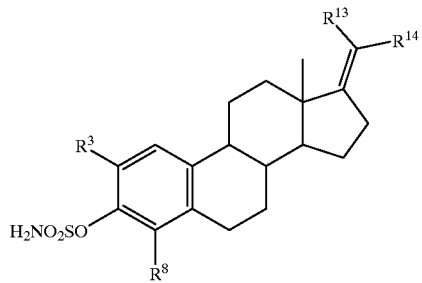

(IV)

wherein:
$R^3$ is selected from the group consisting of hydrogen, —CN, —NO$_2$, —COOR$^4$ wherein $R^4$ is hydrogen or lower alkyl, —(CH$_2$)$_n$OR$^5$ and —(CH$_2$)$_n$NR$^6$R$^7$ wherein n is 0 to 6, $R^5$ is hydrogen or lower alkyl, and $R^6$ and $R^7$ are selected from the group consisting of hydrogen, lower alkyl and lower acyl, or together form the cyclic substituent (II)

(II)

wherein Q is NH, O or CH$_2$; and
$R^8$ is selected from the group consisting of hydrogen, —NO$_2$, and NR$^6$R$^7$; and
$R^{13}$ and $R^{14}$ are independently selected from the group consisting of hydrogen, lower alkyl, —CN, —(CH$_2$)$_m$—O—(CH$_2$)$_q$—NR$^6$R$^7$ and —COOR$^4$ wherein m and q are integers in the range of 0 to 6 and 1 to 6, respectively.

34. The compound of claim 33, wherein one of $R^{13}$ and $R^{14}$ is hydrogen and the other is selected from the group consisting of hydrogen, lower alkyl, —CN, —(CH$_2$)$_m$—O—(CH$_2$)$_q$—NR$^6$R$^7$ and —COOR$^4$, or wherein $R^{13}$ and $R^{14}$ are both —CN.

35. The compound of claim 33, wherein $R^3$ and $R^8$ are both hydrogen.

36. The compound of claim 34, wherein $R^3$ and $R^8$ are both hydrogen.

37. A compound having the structural formula (V)

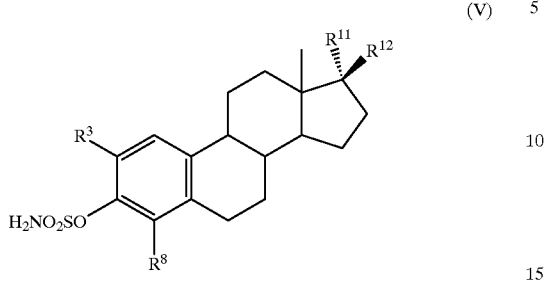

(V)

wherein:

$R^3$ is selected from the group consisting of hydrogen, —CN, —NO$_2$, —COOR$^4$ wherein $R^4$ is hydrogen or lower alkyl, —(CH$_2$)$_n$OR$^5$ and —(CH$_2$)$_n$NR$^6$R$^7$ wherein n is 0 to 6, $R^5$ is hydrogen or lower alkyl, and $R^6$ and $R^7$ are selected from the group consisting of hydrogen, lower alkyl and lower acyl, or together form the cyclic substituent (II)

(II)

wherein Q is NH, O or CH$_2$; and $R^8$ is selected from the group consisting of hydrogen, —NO$_2$, and NR$^6$R$^7$; and one of $R^{11}$ and $R^{12}$ is hydrogen and the other is lower alkyl, lower alkenyl, lower alkynyl, lower alkoxy, lower acyl, lower acyloxy, or —(CH$_2$)$_m$—O—(CH$_2$)$_q$—NR$^6$R$^7$ wherein m and q are integers in the range of 0 to 6 and 1 to 6, respectively.

38. The compound of claim 37, wherein one of $R^{11}$ and $R^{12}$ is hydrogen and the other is —(CH$_2$)$_m$—O—(CH$_2$)$_q$—NR$^6$R$^7$ wherein m is 0 or 1 and q is 2, 3 or 4.

39. The compound of claim 37, wherein $R^3$ and $R^8$ are both hydrogen.

40. The compound of claim 38, wherein $R^3$ and $R^8$ are both hydrogen.

41. A method for inhibiting the enzymatic activity of estrone sulfatase comprising contacting the enzyme with an effective estrone sulfatase inhibiting amount of a compound having the structural formula (III)

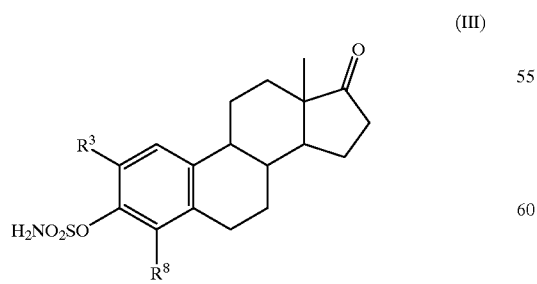

(III)

wherein:

$R^3$ is selected from the group consisting of hydrogen, —CN, —NO$_2$, —COOR$^4$ wherein $R^4$ is hydrogen or lower alkyl, —(CH$_2$)$_n$OR$^5$ and —(CH$_2$)$_n$NR$^6$R$^7$ wherein n is 0 to 6, $R^5$ is hydrogen or lower alkyl, and $R^6$ and $R^7$ are selected from the group consisting of hydrogen, lower alkyl and lower acyl, or together form the cyclic substituent (II)

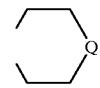

(II)

wherein Q is NH, O or CH$_2$; and $R^8$ is selected from the group consisting of hydrogen, —NO$_2$, and NR$^6$R$^7$, with the proviso that $R^3$ and $R^8$ are not both hydrogen, and with the further proviso that if $R^3$ is —(CH$_2$)$_n$—OR$^5$ and $R^5$ is lower alkyl, then n is other than 0 or with a pharmaceutically acceptable salt or ester thereof.

42. The method of claim 41, wherein $R^3$ is hydrogen and $R^8$ is —NO$_2$.

43. The method of claim 41, wherein $R^3$ is hydrogen and $R^8$ is NR$^6$R$^7$.

44. A method for inhibiting the enzymatic activity of estrone sulfatase comprising contacting the enzyme with an effective estrone sulfatase inhibiting amount of a compound having the structural formula (IV)

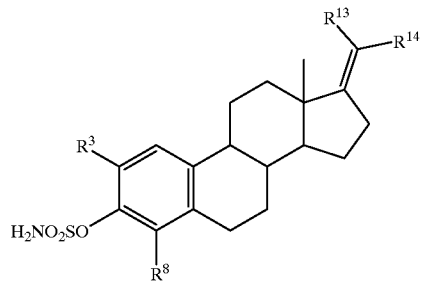

(IV)

wherein:

$R^3$ is selected from the group consisting of hydrogen, —CN, —NO$_2$, —COOR$^4$ wherein $R^4$ is hydrogen or lower alkyl, —(CH$_2$)$_n$OR$^5$ and —(CH$_2$)$_n$NR$^6$R$^7$ wherein n is 0 to 6, $R^5$ is hydrogen or lower alkyl, and $R^6$ and $R^7$ are selected from the group consisting of hydrogen, lower alkyl and lower acyl, or together form the cyclic substituent (II)

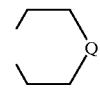

(II)

wherein Q is NH, O or CH$_2$; and $R^8$ is selected from the group consisting of hydrogen, —NO$_2$, and NR$^6$R$^7$; and $R^{13}$ and $R^{14}$ are independently selected from the group consisting of hydrogen, lower alkyl, —CN, —(CH$_2$)$_m$—O—(CH$_2$)$_q$—NR$^6$R$^7$ and —COOR$^4$, wherein m and q are integers in the range of 0 to 6 and 1 to 6, respectively or with a pharmaceutically acceptable salt or ester thereof.

45. The method of claim 44, wherein one of $R^{13}$ and $R^{14}$ is hydrogen and the other is selected from the group consisting of hydrogen, lower alkyl, —CN, —(CH₂)ₙ—O—(CH₂)_{q—NR}⁶R⁷ and —COOR⁴, or wherein R¹³ and R¹⁴ are both —CN.

46. The method of claim 44, wherein R³ and R⁸ are both hydrogen.

47. The method of claim 45, wherein R³ and R⁸ are both hydrogen.

48. A method for inhibiting the enzymatic activity of estrone sulfatase comprising contacting the enzyme with an effective estrone sulfatase inhibiting amount of a compound having the structural formula (V)

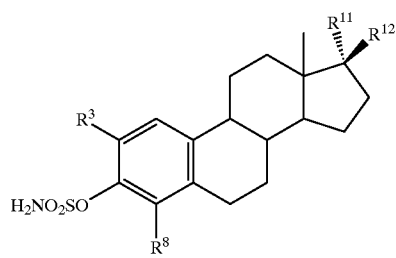
(V)

wherein:

R³ is selected from the group consisting of hydrogen, —CN, —NO₂, —COOR⁴ wherein R⁴ is hydrogen or lower alkyl, —(CH₂)ₙOR⁵ and —(CH₂)ₙNR⁶R⁷ wherein n is 0 to 6, R⁵ is hydrogen or lower alkyl, and R⁶ and R⁷ are selected from the group consisting of hydrogen, lower alkyl and lower acyl, or together form the cyclic substituent (II)

(II)

wherein Q is NH, O or CH₂; and

R⁸ is selected from the group consisting of hydrogen, —NO₂, and NR⁶R⁷; and one of R¹¹ and R¹² is hydrogen and the other is lower alkyl, lower alkenyl, lower alkynyl, lower alkoxy, lower acyl, lower acyloxy, or —(CH₂)ₘ—O—(CH₂)_q—NR⁶R⁷ wherein m and q are integers in the range of 0 to 6 and 1 to 6, respectively, or with a pharmaceutically acceptable salt or ester thereof.

49. The method of claim 48, wherein one of R¹¹ and R¹² is hydrogen and the other is —(CH₂)ₘ—O—(CH₂)_q—NR⁶R⁷ wherein m is 0 or 1 and q is 2, 3 or 4.

50. The method of claim 48, wherein R³ and R⁸ are both hydrogen.

51. The method of claim 49, wherein R³ and R⁸ are both hydrogen.

52. A method for treating an individual with an estrogen-dependent disorder, comprising administering to the individual a pharmacologically effective amount of a compound of structural formula (III)

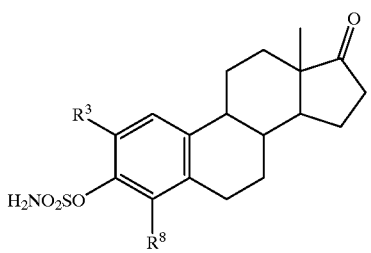
(III)

wherein:

R³ is selected from the group consisting of hydrogen, —CN, —NO₂, —COOR⁴ wherein R⁴ is hydrogen or lower alkyl, —(CH₂)ₙOR⁵ and —(CH₂)ₙNR⁶R⁷ wherein n is 0 to 6, R⁵ is hydrogen or lower alkyl, and R⁶ and R⁷ are selected from the group consisting of hydrogen, lower alkyl and lower acyl, or together form the cyclic substituent (II)

(II)

wherein Q is NH, O or CH₂; and

R⁸ is selected from the group consisting of hydrogen, —NO₂, and NR⁶R⁷, with the proviso that R³ and R⁸ are not both hydrogen, and with the further proviso that if R³ is —(CH₂)ₙ—OR⁵ and R⁵ is lower alkyl, then n is other than 0 or with a pharmaceutically acceptable salt or ester thereof.

53. The method of claim 52, wherein R³ is hydrogen and R⁸ is —NO₂.

54. The method of claim 52, wherein R³ is hydrogen and R⁸ is NR⁶R⁷.

55. A method for treating an individual with an estrogen-dependent disorder, comprising administering to the individual a pharmacologically effective amount of a compound of structural formula (IV)

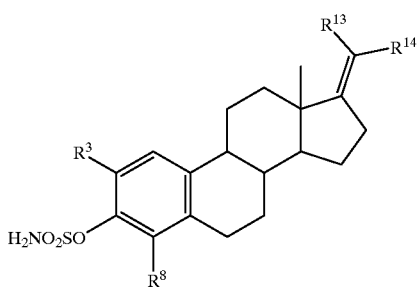
(IV)

wherein:

R³ is selected from the group consisting of hydrogen, —CN, —NO₂, —COOR⁴ wherein R⁴ is hydrogen or lower alkyl, —(CH₂)ₙOR⁵ and —(CH₂)ₙNR⁶R⁷ wherein n is 0 to 6, R⁵ is hydrogen or lower alkyl, and R⁶ and R⁷ are selected from the group consisting of hydrogen, lower alkyl and lower acyl, or together form the cyclic substituent (II)

(II)

wherein Q is NH, O or CH$_2$; and

R$^8$ is selected from the group consisting of hydrogen, —NO$_2$, and NR$^6$R$^7$; and R$^{13}$ and R$^{14}$ are independently selected from the group consisting of hydrogen, lower alkyl, —CN, —(CH$_2$)$_m$—O—(CH$_2$)$_q$—NR$^6$R$^7$ and —COOR$^4$, wherein m and q are integers in the range of 0 to 6 and 1 to 6, respectively or with a pharmaceutically acceptable salt or ester thereof.

56. The method of claim 55, wherein one of R$^{13}$ and R$^{14}$ is hydrogen and the other is selected from the group consisting of hydrogen, lower alkyl, —CN, —(CH$_2$)$_m$—O—(CH$_2$)$_q$—NR$^6$R$^7$ and —COOR$^4$, or wherein R$^{13}$ and R$^{14}$ are both —CN.

57. The method of claim 55, wherein R$^3$ and R$^8$ are both hydrogen.

58. The method of claim 56, wherein R$^3$ and R$^8$ are both hydrogen.

59. A method for treating an individual with an estrogen-dependent disorder, comprising administering to the individual a pharmacologically effective amount of a compound of structural formula (V)

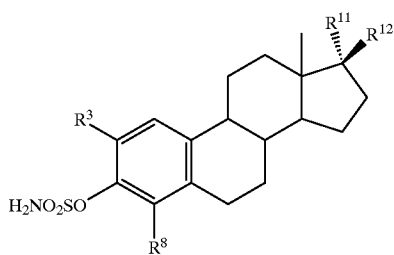

(V)

wherein:

R$^3$ is selected from the group consisting of hydrogen, —CN, —NO$_2$, —COOR$^4$ wherein R$^4$ is hydrogen or lower alkyl, —(CH$_2$)$_n$OR$^5$ and —(CH$_2$)$_n$NR$^6$R$^7$ wherein n is 0 to 6, R$^5$ is hydrogen or lower alkyl, and R$^6$ and R$^7$ are selected from the group consisting of hydrogen, lower alkyl and lower acyl, or together form the cyclic substituent (II)

(II)

wherein Q is NH, O or CH$_2$; and

R$^8$ is selected from the group consisting of hydrogen, —NO$_2$, and NR$^6$R$^7$; and one of R$^{11}$ and R$^{12}$ is hydrogen and the other is lower alkyl, lower alkenyl, lower alkynyl, lower alkoxy, lower acyl, lower acyloxy, or —(CH$_2$)$_m$—O—(CH$_2$)$_q$—NR$^6$R$^7$ wherein m and q are integers in the range of 0 to 6 and 1 to 6, respectively, or with a pharmaceutically acceptable salt or ester thereof.

60. The method of claim 59, wherein one of R$^{11}$ and R$^{12}$ is hydrogen and the other is —(CH$_2$)$_m$—O—(CH$_2$)$_q$—NR$^6$R$^7$ wherein m is 0 or 1 and q is 2, 3 or 4.

61. The method of claim 59, wherein R$^3$ and R$^8$ are both hydrogen.

62. The method of claim 60, wherein R$^3$ and R$^8$ are both hydrogen.

63. A pharmaceutical composition comprising an effective estrone sulfatase inhibiting amount of the compound of claim 30 in combination with a pharmaceutically acceptable carrier.

64. A pharmaceutical composition comprising an effective estrone sulfatase inhibiting amount of the compound of claim 33 in combination with a pharmaceutically acceptable carrier.

65. A pharmaceutical composition comprising an effective estrone sulfatase nhibiting amount of the compound of claim 37 in combination with a pharmaceutically acceptable carrier.

* * * * *